(12) United States Patent
Chen et al.

(10) Patent No.: US 12,286,419 B2
(45) Date of Patent: Apr. 29, 2025

(54) METHODS OF MANUFACTURING A BIFUNCTIONAL COMPOUND

(71) Applicant: Arvinas Operations, Inc., New Haven, CT (US)

(72) Inventors: Chungpin Herman Chen, Madison, CT (US); Hanqing Dong, Madison, CT (US)

(73) Assignee: Arvinas Operations, Inc., New Haven, CT (US)

( * ) Notice: Subject to any disclaimer, the term of this patent is extended or adjusted under 35 U.S.C. 154(b) by 0 days.

(21) Appl. No.: 17/873,748

(22) Filed: Jul. 26, 2022

(65) Prior Publication Data

US 2023/0069491 A1    Mar. 2, 2023

Related U.S. Application Data

(60) Provisional application No. 63/225,858, filed on Jul. 26, 2021.

(51) Int. Cl.

| | | |
|---|---|---|
| *C07D 401/14* | (2006.01) | |
| *B01J 25/02* | (2006.01) | |
| *C07C 231/12* | (2006.01) | |
| *C07C 237/06* | (2006.01) | |
| *C07C 303/32* | (2006.01) | |
| *C07C 309/19* | (2006.01) | |
| *C07D 207/16* | (2006.01) | |
| *C07D 209/46* | (2006.01) | |
| *C07D 211/32* | (2006.01) | |
| *C07D 295/205* | (2006.01) | |
| *C07D 401/04* | (2006.01) | |

(52) U.S. Cl.
CPC ............ *C07D 401/14* (2013.01); *B01J 25/02* (2013.01); *C07C 231/12* (2013.01); *C07C 237/06* (2013.01); *C07C 303/32* (2013.01); *C07C 309/19* (2013.01); *C07D 207/16* (2013.01); *C07D 209/46* (2013.01); *C07D 211/32* (2013.01); *C07D 295/205* (2013.01); *C07D 401/04* (2013.01)

(58) Field of Classification Search
CPC .. C07D 401/14; C07D 207/16; C07D 209/46; C07D 211/32; C07D 295/205; C07D 401/04; B01J 25/02; C07C 231/12; C07C 303/32

See application file for complete search history.

(56) References Cited

U.S. PATENT DOCUMENTS

| | | | |
|---|---|---|---|
| 4,885,363 A | 12/1989 | Tweedle et al. | |
| 5,474,756 A | 12/1995 | Tweedle et al. | |
| 5,608,110 A | 3/1997 | Ramalingam et al. | |
| 5,656,254 A | 8/1997 | Ramalingam et al. | |
| 5,662,885 A | 9/1997 | Pollak et al. | |
| 5,665,329 A | 9/1997 | Ramalingam et al. | |
| 5,688,487 A | 11/1997 | Linder et al. | |
| 5,720,934 A | 2/1998 | Dean et al. | |
| 5,780,006 A | 7/1998 | Pollak et al. | |
| 5,846,519 A | 12/1998 | Tweedle et al. | |
| 5,976,495 A | 11/1999 | Pollak et al. | |
| 6,093,382 A | 7/2000 | Wedeking et al. | |
| 6,143,274 A | 11/2000 | Tweedle et al. | |
| 10,647,698 B2 | 5/2020 | Crew et al. | |
| 10,836,749 B1 * | 11/2020 | Fan ..................... | C07D 403/14 |
| 11,261,178 B2 | 3/2022 | Fan et al. | |
| 2020/0317659 A1 | 10/2020 | Hirano et al. | |

FOREIGN PATENT DOCUMENTS

| | | | | |
|---|---|---|---|---|
| CN | 113816927 A | 12/2021 | | |
| CN | 117126133 A | 11/2023 | | |
| EP | 3412666 A1 * | 12/2018 | .......... | C07D 471/04 |
| WO | WO-9503280 A1 | 2/1995 | | |
| WO | WO-9506633 A1 | 3/1995 | | |
| WO | WO-9603427 A1 | 2/1996 | | |
| WO | WO-2018102725 A1 * | 6/2018 | .......... | A61K 31/454 |

(Continued)

OTHER PUBLICATIONS

Heterocycles Old and New: Carbonylazoles as Chemoselective Acylation Reagents and the Synthesis and Applications of Benzindolizinones, Ph.D. thesis, UC Berkeley, by Stephen T. Heller (Year: 2012).*

(Continued)

*Primary Examiner* — Jeffrey S Lundgren
*Assistant Examiner* — Alexander K. Showalter
(74) *Attorney, Agent, or Firm* — Sheppard Mullin Richter & Hampton LLP

(57) ABSTRACT

This disclosure pertains to the preparation of bifunctional compounds (e.g., Compound 1), intermediates in the preparation of such compounds, and preparation of such intermediates.

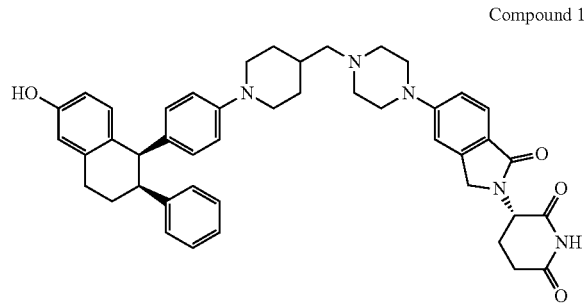

Compound 1

7 Claims, No Drawings

(56) References Cited

FOREIGN PATENT DOCUMENTS

| WO | WO-2019040109 A1 * | 2/2019 | ........... C07C 231/02 |
|---|---|---|---|
| WO | WO-2021061204 A1 | 4/2021 | |
| WO | WO-2023009521 A1 | 2/2023 | |

OTHER PUBLICATIONS

Flanagan et al., ARV-471, an oral estrogen receptor PROTAC™ protein degrader for breast cancer, Arvinas meeting poster, San Antonio Breast Cancer Symposium, 1 pg. (Year: 2018).*

Flanagan et al., Identification of Oral Estrogen Receptor PROTAC Degraders for Breast Cancer, Arvinas meeting poster, San Antonio Breast Cancer Symposium, 1 pg. (Year: 2017).*

Flanagan et al., ARV-471, an oral estrogen receptor PROTACâ¢ protein degrader for breast cancer, Arvinas meeting poster, San Antonio Breast Cancer Symposium, 1 pg. (Year: 2018).*

Hornberger, K R., et al., "Physicochemical Property Determinants of Oral Absorption for Protac Protein Degraders", Journal of Medicinal Chemistry (2023);66(12): 8281-8287.

Mullard, A., "First targeted protein degrader hits the clinic", Nature Reviews, Drug Discovery (Apr. 2019); 18: 237-239.

Scudellari, M., "The protein slayers", Nature (Mar. 21, 2019); 567: 298-300.

Flanagan, J., et al., "ARV-471, an oral estrogen receptor PROTAC ™ protein degrader for breast cancer", Arvinas meeting poster, San Antonio Breast Cancer Symposium (Dec. 4-8, 2018); 1 page.

Flanagan, J., et al., "Identification of Oral Estrogen Receptor PROTAC Degraders for Breast Cancer", Arvinas meeting poster, San Antonio Breast Cancer Symposium (Dec. 5-9, 2017); 1 page.

Hamilton, E., et al., "ARV-471, a new PROTAC® estrogen receptor (ER) degrader, in women with ER-positive/human epidermal growth factor receptor 2-negative (ER+/HER2-) advanced breast cancer", Arvinas meeting poster summary, Arvinas, Inc. (Dec. 2021); 1 page.

Hamilton, E., et al., "Clinical trial of ARV-471, an estrogen receptor (Er) Protac degrader, combined with palbociclib in people with ER-positive/human epidermal growth factor receptor 2-negative (ER+/HER2-) advanced breast cancer", Arvinas meeting poster summary, Arvinas Estrogen Receptor, Inc. (Jun. 2022); 2 pages.

Hamilton, E. P., et al., "ARV-471, an estrogen receptor (Er) Protac degrader, combined with palbociclib in advanced ER+/human epidermal growth factor receptor 2 negative breast cancer: phase 1b cohort (part C) of a phase 1/2 study", Arvinas meeting poster, American Society for Clinical Oncology (ASCO) Annual Meeting, Chicago, IL (Jun. 3-7, 2022); 1 page.

Hamilton, E., et al., "First-in-human safety and activity of ARV-471, a novel PROTAC® estrogen receptor degrader, in ER+/HER2- locally advanced or metastatic breast cancer", Arvinas meeting poster, San Antonio Breast Cancer Symposium, San Antonio, TX (Dec. 7-10, 2021); 1 page.

Snyder, L. B., "The Discovery of ARV-471, an Orally Bioavailable Estrogen Receptor Degrading PROTAC® for the Treatment of Patients with Breast Cancer", Arvinas meeting poster, AACR Annual Meeting 2021 (Apr. 10-15, 2021 and May 17-21, 2021); 16 pages.

* cited by examiner

METHODS OF MANUFACTURING A BIFUNCTIONAL COMPOUND

CROSS-REFERENCE TO RELATED APPLICATIONS

This application claims priority to, and the benefit of, U.S. Application No. 63/225,858, filed Jul. 26, 2021, the entirety of which is incorporated herein by reference.

BACKGROUND

Certain bifunctional compounds can target specific cellular proteins for degradation via the ubiquitin-proteasome system. Examples of such proteolysis targeting chimeric compounds (i.e., "PROTAC® protein degraders") that target the Estrogen Receptor (ER) for ubiquitination and subsequent degradation are disclosed in U.S. Pat. No. 10,647,698, which is incorporated herein by reference in its entirety. Such bifunctional molecules exhibit a range of pharmacological activities consistent with the degradation of the ER including, but not limited to, treatment or amelioration of a disease condition such as cancer (e.g., breast cancer, uterine cancer, ovarian cancer, prostate cancer, endometrial cancer), or endometriosis.

There is a need in the art to provide improved processes for manufacturing such bifunctional compounds.

SUMMARY

A bifunctional molecule of particular interest is referred to herein as Compound 1. The present disclosure is directed to: (i) processes for preparing Compound 1, (ii) intermediates used in the preparation of Compound 1 (i.e., Intermediates I-1, I-2, I-2A, I-3, I-3A, I-4, I-5, I-6, I-6A, I-8, and I-9), and (iii) processes for preparing such intermediates.

In some aspects, disclosed herein are methods for reductively aminating Intermediate I-9:

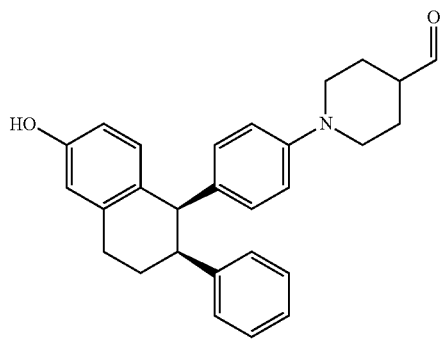

with salt Intermediate I-8:

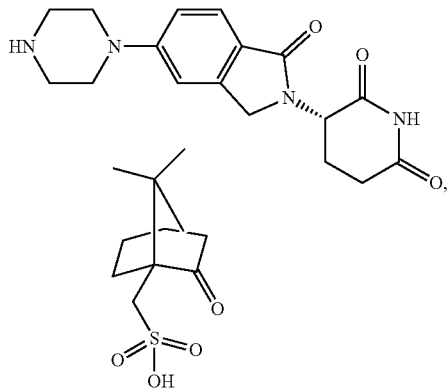

a base, and a reducing agent to provide Compound 1:

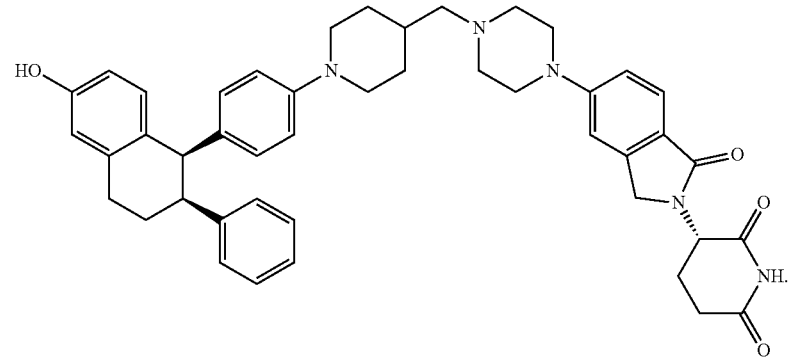

In some embodiments, the base is an amine base or a carbonate salt.

In some embodiments, the base is N-methyl-morpholine, trimethylamine, triethylamine, N,N-diisopropylethylamine, N,N-dimethylaniline, lithium carbonate, sodium carbonate, potassium carbonate, or magnesium carbonate.

In some embodiments, the molar ratio of base to salt Intermediate I-8 is about 1:1 to about 3:1, and preferably is about 1:1 to about 2:1.

In some embodiments, the molar ratio of base to salt Intermediate I-8 is about 1.00:1, about 1.05:1, about 1.10:1, about 1.15:1, about 1.20:1, about 1.25:1, about 1.30:1, about 1.35:1, about 1.40:1, about 1.45:1, about 1.50:1, about 1.55:1, about 1.60:1, about 1.65:1, about 1.70:1, about 1.75:1, about 1.80:1, about 1.85:1, about 1.90:1, about 1.95:1, about 2.00:1, about 2.05:1, about 2.10:1, about 2.15:1, about 2.20:1, about 2.25:1, about 2.30:1, about 2.35:1, about 2.40:1, or about 2.45:1.

In some embodiments, the reducing agent is sodium triacetoxyborohydride, sodium borohydride, sodium cyanoborohydride, or hydrogen in the presence of a catalyst.

In some embodiments, the molar ratio of reducing agent to salt Intermediate I-8 is about 1:1 to about 3:1, and preferably is about 1:1 to about 2:1.

In some embodiments, the molar ratio of reducing agent to salt Intermediate I-8 is about 1.00:1, about 1.05:1, about 1.10:1, about 1.15:1, about 1.20:1, about 1.25:1, about 1.30:1, about 1.35:1, about 1.40:1, about 1.45:1, about 1.50:1, about 1.55:1, about 1.60:1, about 1.65:1, about 1.70:1, about 1.75:1, about 1.80:1, about 1.85:1, about 1.90:1, about 1.95:1, about 2.00:1, about 2.05:1, or about 2.10:1.

In some embodiments, the solvent is a polar solvent.

In some embodiments, the polar solvent is dimethylacetamide, N-methyl-2-pyrrolidone, or 2-methyl tetrahydrofuran.

In some embodiments, the temperature of the reductive amination is about −30° C. to about 30° C., and preferably is about −10° C. to about 10° C.

In some embodiments, the temperature of the reductive amination is about −30° C., about −25° C., about −20° C., about −15° C., about −10° C., about −5° C., about 0° C., about 5° C., about 10° C., about 15° C., about 20° C., about 25° C., or about 30° C.

In some embodiments, further comprising quenching the reducing agent with water, an alcohol, preferably ethanol, or a combination thereof, to form a first solution.

In some embodiments, further comprising forming a precipitate comprising Compound 1, wherein a second solution of an alcohol and water, preferably ethanol and water, is added to the first solution to form a precipitate comprising Compound 1.

In some embodiments, further comprising forming a precipitate comprising Compound 1, wherein a third solution comprising water, an alcohol, preferably ethanol, or a combination thereof, is added to the first solution to quench the reducing agent and thereby forms a precipitate comprising Compound 1.

In some embodiments, the temperature of the second solution of alcohol and water is about 50° C. to about 90° C., preferably about 60° C. to about 80° C., when the solution of alcohol and water is added to the first solution.

In some embodiments, the temperature of second solution is about 70° C. when the second solution is added to the first solution.

In some embodiments, the second solution has an alcohol: water ratio of about 1:1 (v/v).

In some embodiments, after addition of the second solution to the first solution or the third solution, the resulting suspension is cooled to about 50° C., about 40° C., about 30° C., about 25° C., about 20° C., or about 15° C. The resulting suspension is then filtered, and the filtrate is washed with water and an alcohol, preferably water and ethanol.

In some embodiments, the method for preparing Compound 1 comprises purifying Compound 1. In some embodiments, purifying Compound 1 comprises dissolving Compound 1 in a dichloromethane and methanol solution. In some embodiments, the ratio of dichloromethane to methanol in the solution is about 8:1 (v/v) to about 11:1 (v/v). In some embodiments, the ratio of dichloromethane to methanol in the solution is about 9:1 (v/v) to about 11:1 (v/v). In some embodiments, the ratio of dichloromethane to methanol in the solution is about 8:1 (v/v), about 8.5:1 (v/v), about 9:1 (v/v), about 9.1:1 (v/v), about 9.2:1 (v/v), about 9.3:1 (v/v), about 9.4:1 (v/v), about 9.5:1 (v/v), about 9.6:1 (v/v), about 9.7:1 (v/v), about 9.8:1 (v/v), about 9.9:1 (v/v), about 10:1 (v/v), about 10.5:1 (v/v), or about 11:1 (v/v). In some embodiments, the ratio of dichloromethane to methanol in the solution is about 9.4:1 (v/v).

In some embodiments, purifying Compound 1 comprises distillatively exchanging the solution of dichloromethane/methanol for a polar protic solvent. In some embodiments, the polar protic solvent is methanol, ethanol, n-propanol, isopropanol, or n-butanol. In some embodiments, the polar protic solvent is n-butanol.

In some aspects, disclosed herein are methods comprising reacting Intermediate I-6:

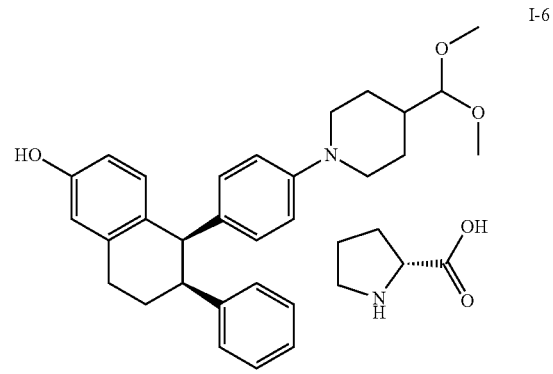

I-6 with an acid in a solvent to provide Intermediate I-9.

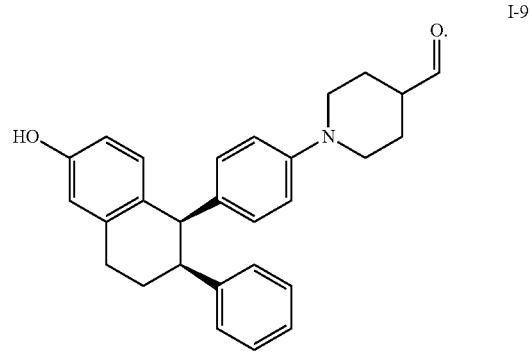 [SMILES: O=CC1CCN(c2ccc([C@@H]3c4ccc(O)cc4CC[C@@H]3c3ccccc3)cc2)CC1]

I-9

In some embodiments, the solvent comprises water and an ethereal solvent. In some embodiments, the ethereal solvent is 2-methyltetrahydrofuran or tetrahydrofuran.

In some embodiments, the acid is hydrochloric acid.

In some embodiments, the additive is an antioxidant, radical scavenger, oxygen scavenger, or metal chelator.

In some embodiments, the additive is dibutylhydroxytoluene, ascorbic acid, alpha-tocopherol, or ethylenediaminetetraacetic acid.

In some embodiments, the method further comprises reacting Intermediate I-6 with the acid and, the optional additive in the solvent at a temperature of about 0° C. to about 40° C., and, preferably, at a temperature of about 10° C. to about 30° C.

In some embodiments, the method further comprises adding an aqueous solution to adjust the pH to about pH 7 to about pH 8 after reacting Intermediate I-6 with the acid and the optional additive in the solvent. In some embodiments, the aqueous solution is an aqueous tripotassium phosphate solution.

In some embodiments, the method further comprises separating an organic layer and an aqueous layer after adjusting of the pH with the aqueous solution. In some embodiments, the aqueous layer is extracted with an ethereal solvent to form an organic extract that is then concentrated. In some embodiments, the ethereal extraction solvent is 2-methyltetrahydrofuran.

In some embodiments, concentration of the organic extract is conducted under vacuum at a temperature of about 20° C. to about 70° C. In some embodiments, concentration of the organic extract is conducted under vacuum at a temperature of about 35° C. to about 55° C.

In some embodiments, the concentrated organic extract is combined with dimethylacetamide and re-concentrated under vacuum.

In some embodiments, after the re-concentration of the organic extract and dimethylacetamide under vacuum, the molar ratio of ethereal solvent relative to Intermediate I-9 in the re-concentrated organic extract is about 0.1:1 or less. In some embodiments, the ethereal solvent is 2-methyltetrahydrofuran.

In some aspects, provided herein are methods comprising:
(a) combining racemic Intermediate I-5:

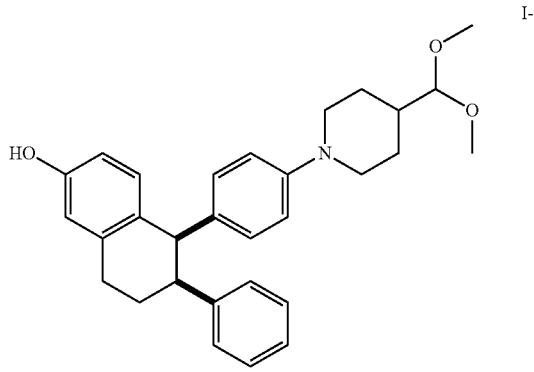

with an additive in a solvent to prepare a first reaction mixture;
(b) heating the first reaction mixture at reflux to prepare a fourth solution, followed by cooling the fourth solution to a temperature of about 50° C. to about 100° C., and preferably the temperature is about 65° C. to about 75° C.;

(c) combining (R)-proline and water to prepare a second solution, wherein the molar ratio of (R)-proline to the total amount of Intermediate I-5 is about 0.40:1 to about 1.00:1;
(d) adding about 1% to less than about 50% by volume, preferably about 5% to about 25% by volume, of the second solution to the first solution to prepare a second reaction mixture;
(e) adding a first amount of an agent that induces nucleation to the second reaction mixture to prepare a third reaction mixture;
(f) adding about 1% to less than about 50% by volume, preferably about 5% to about 25% by volume, of the second solution to the third reaction mixture to prepare a fourth reaction mixture;
(g) adding a second amount of the agent that induces nucleation to the fourth reaction mixture to prepare a fifth reaction mixture; and
(h) adding the remainder of the second solution to the fifth reaction mixture to prepare a sixth reaction mixture comprising Intermediate I-6.

In some embodiments, the first reaction mixture comprises a mixture of alcoholic and ethereal solvents. In some embodiments, the first reaction mixture comprises a mixture of 2-propanol and 2-methyl-tetrahydrofuran.

In some embodiments, the agent that induces nucleation is a crystallization promoter, preferably the crystallization promoter is a seed crystal comprising Intermediate I-6.

In some embodiments, the molar ratio of the total amount of the crystallization promoter compared to Intermediate I-5 is about 0.0001:1 to about 0.01:1, and preferably the molar ratio is about 0.0005:1 to about 0.005:1.

In some embodiments, the molar ratio of the total amount of the crystallization promoter compared to Intermediate I-5 is about 0.0008:1, about 0.0009:1, about 0.0010:1, about 0.0011:1, about 0.0012:1, about 0.0013:1, about 0.0014:1, about 0.0015:1, about 0.0016:1, about 0.0017:1, or about 0.0018:1.

In some embodiments, the first amount of the agent that induces nucleation is approximately equal to the second amount of the agent that induces nucleation. In some embodiments, the first amount of the crystallization promoter is approximately equal to the second amount of the crystallization promoter.

In some embodiments, the molar ratio of the first amount of the crystallization promoter compared to Intermediate I-5 is about 0.0008:1, about 0.0009:1, about 0.0010:1, about 0.0011:1, about 0.0012:1, about 0.0013:1, about 0.0014:1, about 0.0015:1, about 0.0016:1, about 0.0017:1, or about 0.0018:1. In some embodiments, the molar ratio of the second amount of the crystallization promoter compared to Intermediate I-5 is about 0.0008:1, about 0.0009:1, about 0.0010:1, about 0.0011:1, about 0.0012:1, about 0.0013:1, about 0.0014:1, about 0.0015:1, about 0.0016:1, about 0.0017:1, or about 0.0018:1.

In some embodiments, the additive is an antioxidant, radical scavenger, oxygen scavenger, or metal chelator.

In some embodiments, the additive is dibutylhydroxytoluene, ascorbic acid, alpha-tocopherol, or ethylenediaminetetraacetic acid.

In some embodiments, the molar ratio of the total amount of (R)-proline used in the process to the total amount of Intermediate I-5 used in the process is about 0.40:1 to about 0.90:1, preferably about 0.50:1 to about 0.75:1.

In some embodiments, the molar ratio of the total amount of (R)-proline used in the process to the total amount of Intermediate I-5 used in the process is about 0.50:1, about 0.51:1, about 0.52:1, about 0.53:1, about 0.54:1, about 0.55:1, about 0.56:1, about 0.57:1, about 0.58:1, about 0.59:1, about 0.60:1, about 0.61:1, about 0.62:1, about 0.63:1, about 0.64:1, about 0.65:1, about 0.66:1, about 0.67:1, about 0.68:1, about 0.69:1, or about 0.70:1.

In some embodiments, upon completion of the reaction to prepare Intermediate I-6, the completed reaction is cooled from a temperature of about 50° C. to about 100° C., preferably about 65° C. to about 75° C., to a temperature of about 25° C., at a constant rate over a period of at least about 15 minutes, at least about 30 minutes, at least about 60 minutes, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, or at least about 12 hours.

In some embodiments, upon completion of cooling the completed reaction, the Intermediate I-6 is recovered by filtration, washed with solvent, and dried.

In some embodiments, the solvent used to wash the Intermediate I-6 is 2-propanol.

In some embodiments, the Intermediate I-6 is dried under vacuum at a temperature of about 30° C. to about 60° C. In some embodiments, the Intermediate I-6 is dried under vacuum at a temperature of about 40° C. to about 50° C.

In some aspects, disclosed herein are methods comprising providing a mixture comprising Intermediate I-4:

I-4

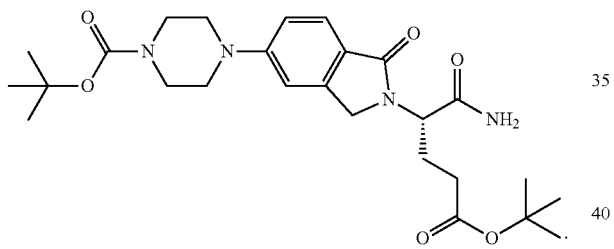

and camphorsulfonic acid in a solvent to provide salt Intermediate I-8:

I-8

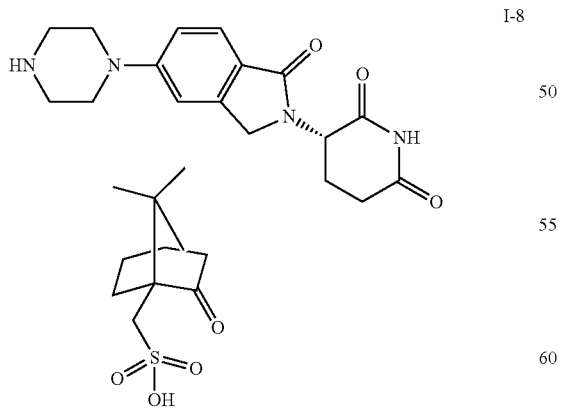

and one or more byproducts.

In some embodiments, the molar ratio of camphorsulfonic acid to Intermediate I-4 in the reaction mixture is about 1:1 to about 3:1, preferably about 1.5:1 to about 2.5:1.

In some embodiments, the molar ratio of camphorsulfonic acid to Intermediate I-4 in the reaction mixture is about 1.90:1, about 1.95:1, about 2.00:1, about 2.05:1, about 2.10:1, about 2.15:1, about 2.20:1, about 2.25:1, about 2.30:1, or about 2.35:1.

In some embodiments, the camphorsulfonic acid is (+)-camphorsulfonic acid.

In some embodiments, the solvent comprises acetonitrile, dimethylformamide, or a mixture thereof.

In some embodiments, the solvent comprises acetonitrile and dimethylformamide in a ratio of about 1:1 (v/v) to about 8:1 (v/v), preferably in a ratio of about 2:1 (v/v) to about 6:1 (v/v).

In some embodiments, the method further comprises heating Intermediate I-4 and camphorsulfonic acid in a solvent at a temperature of about 70° C. to about 100° C., preferably the temperature is about 85° C. to about 100° C.

In some embodiments, the method further comprises heating Intermediate I-4 and camphorsulfonic acid in a solvent at a temperature of about 90° C., about 95° C., or about 100° C.

In some embodiments, the solvent and one or more byproducts of the reaction are azeotropically removed.

In some embodiments, the one or more byproducts of the reaction that are azeotropically removed from the reaction mixture comprise water and tert-butanol.

In some aspects, disclosed herein are methods comprising reacting Intermediate I-3:

I-3

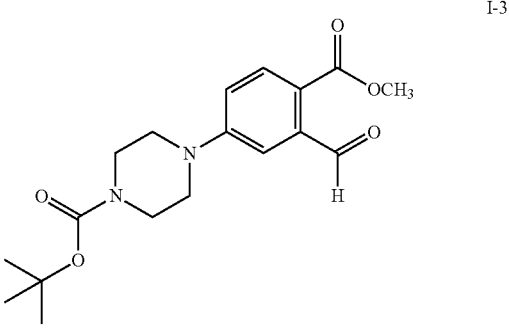 [SMILES: COC(=O)c1ccc(N2CCN(C(=O)OC(C)(C)C)CC2)cc1C=O]

with Intermediate I-3A:

I-3A $H_2N$ ... $NH_2$ in a solvent in the presence of a reducing agent to provide Intermediate I-4:

I-4

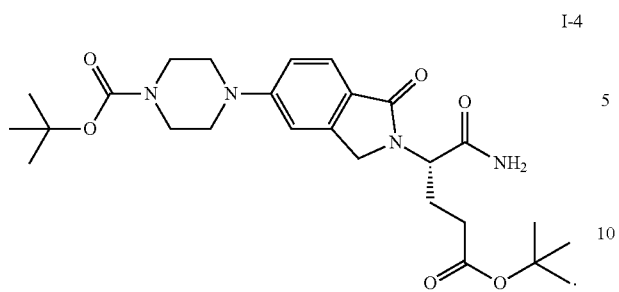

I-3

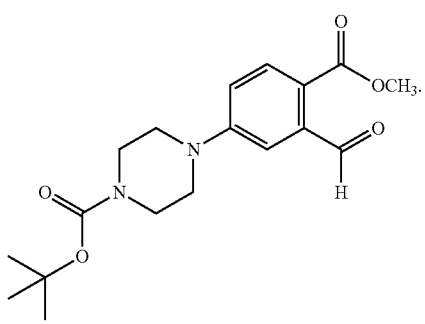

In some embodiments, the solvent comprises an alcohol, preferably the solvent comprises methanol.

In some embodiments, the solvent further comprises an acid, preferably the acid is acetic acid.

In some embodiments, the method further comprises adding the reducing agent as a solution in methanol.

In some embodiments, before starting adding the reducing agent solution, the method comprises cooling Intermediate I-3, Intermediate 3A, and the solvent to a temperature of about 0° C. to about 30° C., preferably the method comprises cooling Intermediate I-3, Intermediate 3A, and the solvent to about 0° C. to about 10° C. In some embodiments the reaction mixture temperature is preferably maintained at said temperature throughout the addition of the reducing agent solution.

In some embodiments, after adding the reducing agent solution, the method further comprises warming the temperature of Intermediate I-3, Intermediate 3A, the reducing agent to 15° C. to about 35° C. In some embodiments, the method further comprises warming the temperature of Intermediate I-3, Intermediate 3A, the reducing agent preferably to about 20° C. to about 30° C.

In some embodiments, the reducing agent is sodium triacetoxyborohydride, sodium borohydride, sodium cyanoborohydride, or hydrogen in the presence of a catalyst.

In some embodiments, the reducing agent is sodium cyanoborohydride.

In some aspects, provided herein are methods comprising reacting Intermediate I-2.

I-2

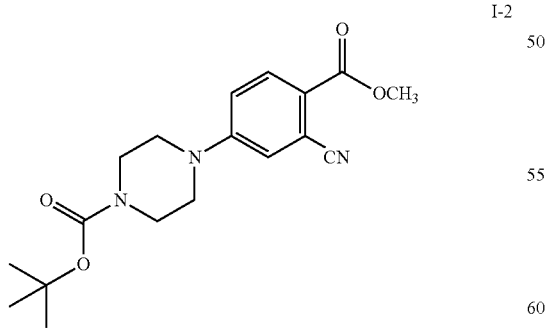

with a reducing agent in a solvent, followed by heating the reaction mixture to provide Intermediate I-3:

In some embodiments, the solvent comprises water, an acid, pyridine, or a combination thereof. In some embodiments, the solvent comprises water, an acid, 2,6-lutidine, or a combination thereof.

In some embodiments, the acid is propionic acid or acetic acid. In some embodiments, the acid is propionic acid. In some embodiments, the acid is acetic acid.

In some embodiments, the reducing agent is Raney nickel.

In some embodiments, method further comprises maintaining the temperature of Intermediate-2, the reducing agent, and the solvent the temperature of Intermediate-2, the reducing agent, and the solvent at about 15° C. to about 30° C., preferably the temperature is maintained at about 20° C. to about 30° C.

In some embodiments, the method further comprises heating Intermediate-2, the reducing agent, and the solvent to a temperature of about 40° C. to about 70° C. In some embodiments, the method further comprises heating Intermediate-2, the reducing agent, and the solvent to a temperature of about 50° C. to about 60° C.

In some aspects, disclosed herein are methods comprising reacting Intermediate I-2A:

I-2A

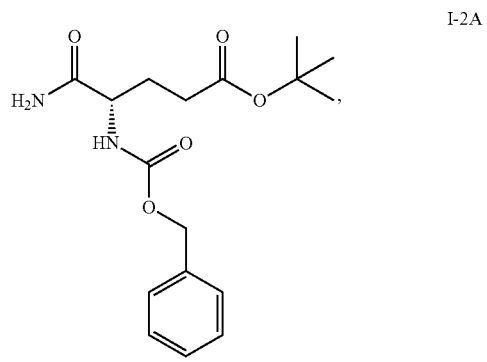 [SMILES: CC(C)(C)OC(=O)CC[C@H](NC(=O)OCc1ccccc1)C(N)=O]

a hydrogen source, and, optionally, a catalyst, in a solvent, to provide Intermediate I-3A:

I-3A

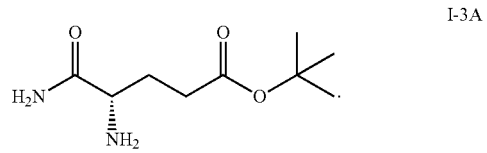

In some embodiments, the catalyst comprises a transition metal. In some embodiments, the transition metal is palladium, rhodium, ruthenium, iridium, or copper.

In some embodiments, the catalyst is Pd(OH)$_2$.

In some embodiments, the hydrogen source is hydrogen gas.

In some embodiments, the pressure of the hydrogen gas is maintained at about 0.5 MPa to about 1.5 MPa, preferably the pressure of the hydrogen gas is maintained at about 0.75 MPa to about 1.25 MPa.

In some embodiments, Intermediate I-9 is prepared a method comprising mixing Intermediate I-6:

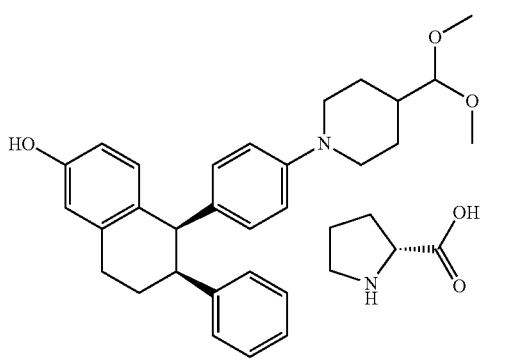

and an acid in a solvent to provide Intermediate I-9:

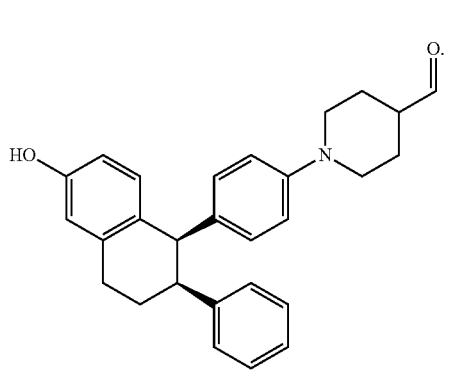

In some embodiments, Intermediate I-6 is prepared by a method comprising:

(a) combining racemic Intermediate I-5:

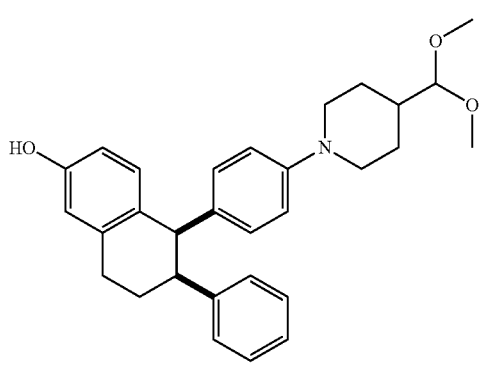

with an additive in a solvent to prepare a first reaction mixture;

(b) heating the first reaction mixture at reflux to prepare a first solution, followed by cooling the first solution to a temperature of about 50° C. to about 100° C., preferably about 65° C. to about 75° C.;

(c) combining (R)-proline and water to prepare a second solution, wherein the molar ratio of (R)-proline to the total amount of Intermediate I-5 is about 0.40:1 to about 1.00:1;

(d) adding about 1% to less than about 50% by volume, preferably about 5% to about 25% by volume, of the second solution to the first solution to prepare a second reaction mixture;

(e) adding a first amount of an agent that induces nucleation to the second reaction mixture to prepare a third reaction mixture;

(f) adding about 1% to less than about 50% by volume, preferably about 5% to about 25% by volume, of the second solution to the third reaction mixture to prepare a fourth reaction mixture;

(g) adding a second amount of the agent that induces nucleation to the fourth reaction mixture to prepare a fifth reaction mixture; and (h) adding the remainder of the second solution to the fifth reaction mixture to prepare a sixth reaction mixture to provide Intermediate I-6:

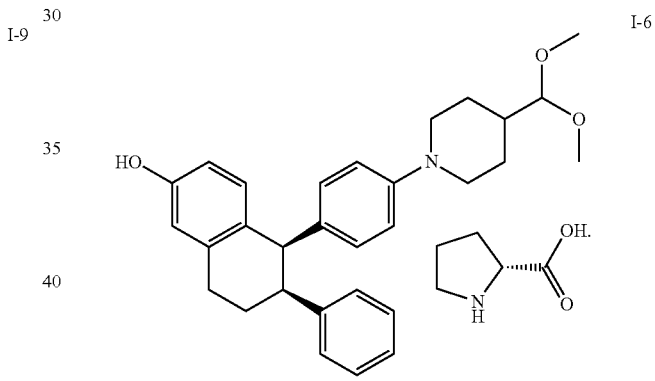

In some embodiments, Intermediate I-8 is prepared by a method comprising reacting Intermediate I-4:

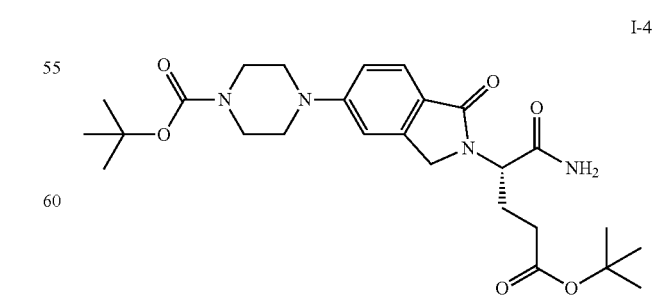

and camphorsulfonic acid in a solvent to provide Intermediate I-8:

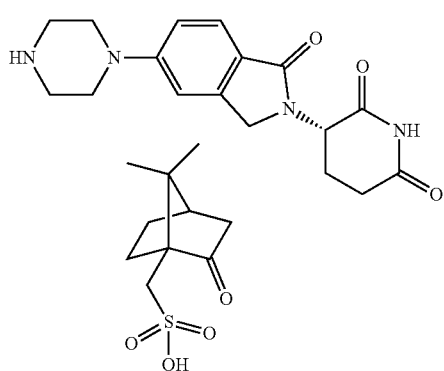

I-8

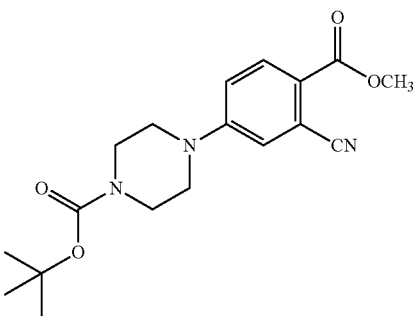

I-2 and a reducing agent in a solvent to provide Intermediate I-3:

and one or more byproducts.

In some embodiments, Intermediate I-4 is prepared by a method comprising reacting Intermediate I-3:

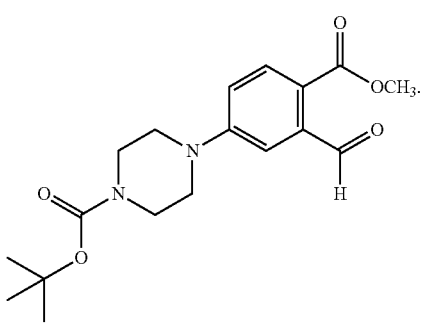

I-3

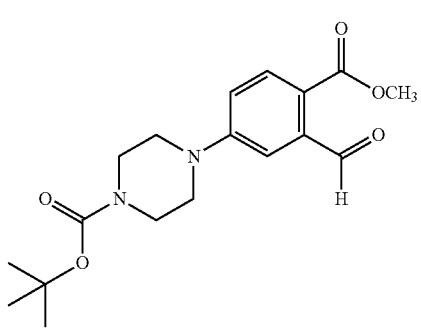

I-3

In some embodiments, Intermediate I-3A is prepared by a method comprising reacting Intermediate I-2A:

with Intermediate I-3A:

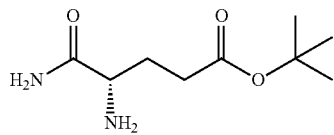

I-3A

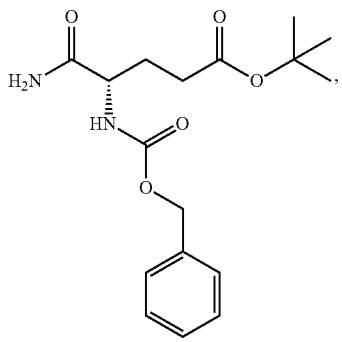

I-2A in a solvent in the presence of a reducing agent to provide Intermediate I-4:

a hydrogen source, and, optionally, a catalyst, in a solvent to provide Intermediate I-3A:

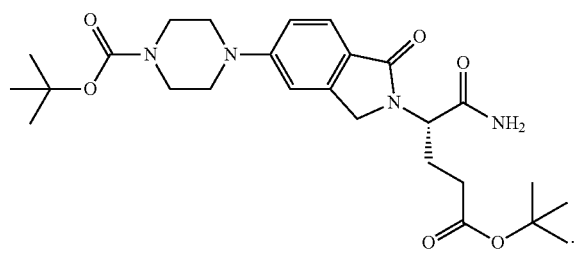

I-4

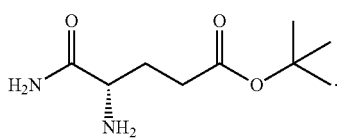

I-3A

In some embodiments, Intermediate I-3 is prepared by a method comprising reacting Intermediate I-2:

In some aspects, provided herein are methods comprising:

(a) reacting Intermediate I-2A:

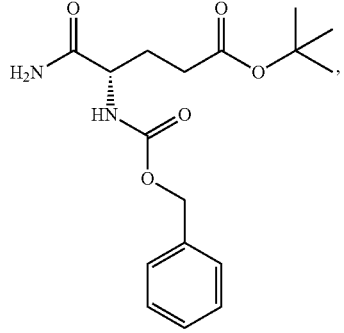

a hydrogen source, and, optionally, a catalyst, in a solvent to provide Intermediate I-3A:

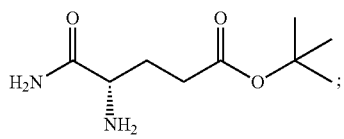

(b) reducing Intermediate I-2:

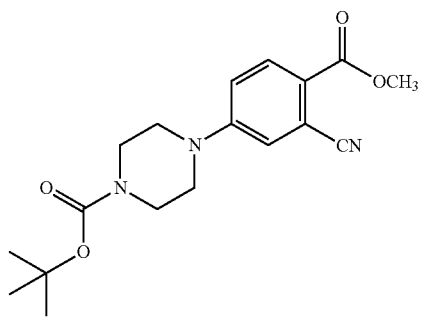

in a solvent in the presence of a reducing agent to provide Intermediate I-3:

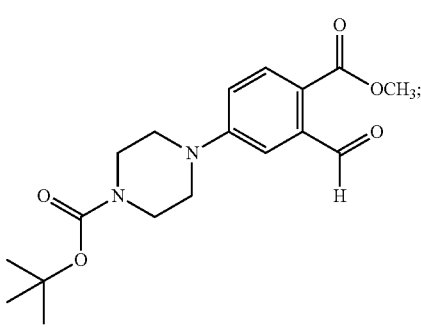

(c) reacting Intermediate I-3:

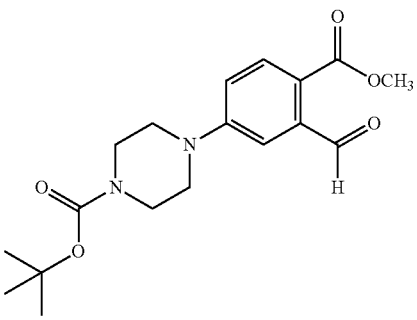

with Intermediate I-3A:

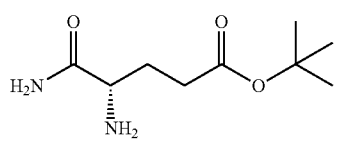

in a solvent in the presence of a reducing agent to provide Intermediate I-4:

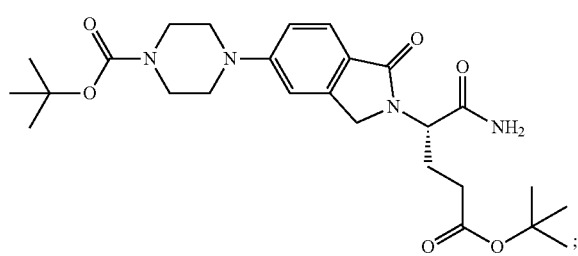

(d) reacting a Intermediate I-4:

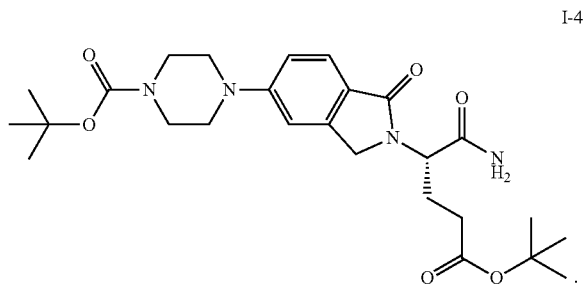 [SMILES: CC(C)(C)OC(=O)CC[C@@H](C(N)=O)N1Cc2cc(N3CCN(C(=O)OC(C)(C)C)CC3)ccc2C1=O]

and camphorsulfonic acid in a solvent to provide salt Intermediate I-8:

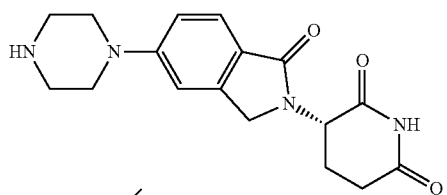

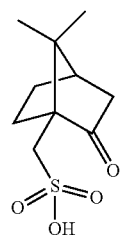

and one or more byproducts;

(e1) combining racemic Intermediate I-5:

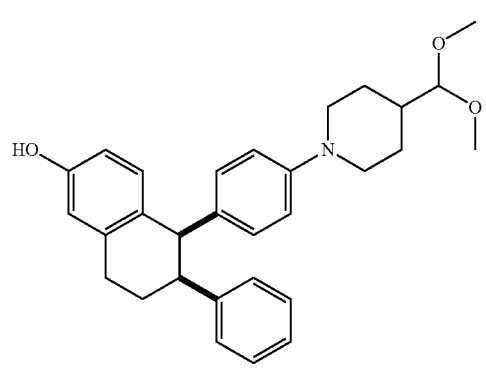

with an additive in a solvent to prepare a first reaction mixture;

(e2) heating the first reaction mixture at reflux to prepare a first solution, followed by cooling the first solution to a temperature of about 50° C. to about 100° C.;

(e3) combining (R)-proline and water to prepare a second solution, wherein the molar ratio of (R)-proline to the total amount of Intermediate I-5 is about 0.40:1 to about 1.00:1;

(e4) adding about 1% to less than about 50% by volume of the second solution to the first solution to prepare a second reaction mixture;

(e5) adding a first amount of an agent that induces nucleation to the second reaction mixture to prepare a third reaction mixture;

(e6) adding about 1% to less than about 50% by volume of the second solution to the third reaction mixture to prepare a fourth reaction mixture;

(e7) adding a second amount of the agent that induces nucleation to the fourth reaction mixture to prepare a fifth reaction mixture; and (e8) adding the remainder of the second solution to the fifth reaction mixture to prepare a sixth reaction mixture to provide Intermediate I-6:

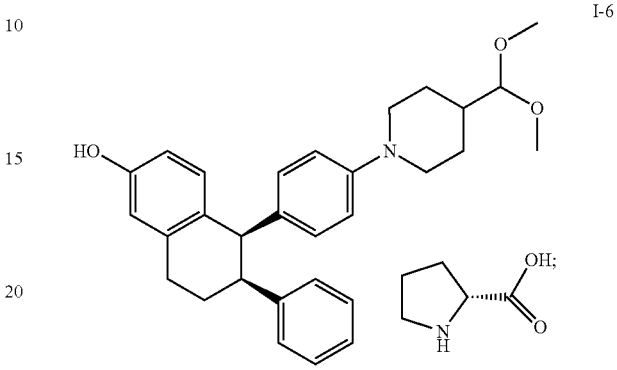

(h) reacting Intermediate I-6:

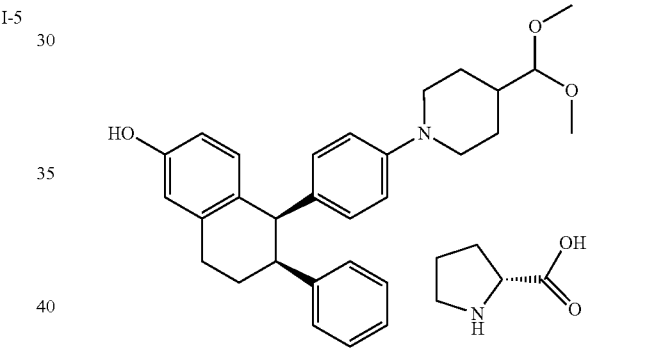

with an acid to provide Intermediate I-9:

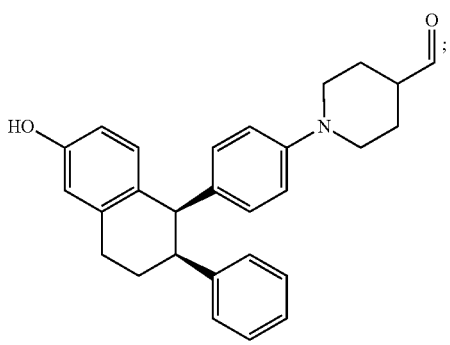

(i) reductively aminating Intermediate I-9:

with salt Intermediate I-8:

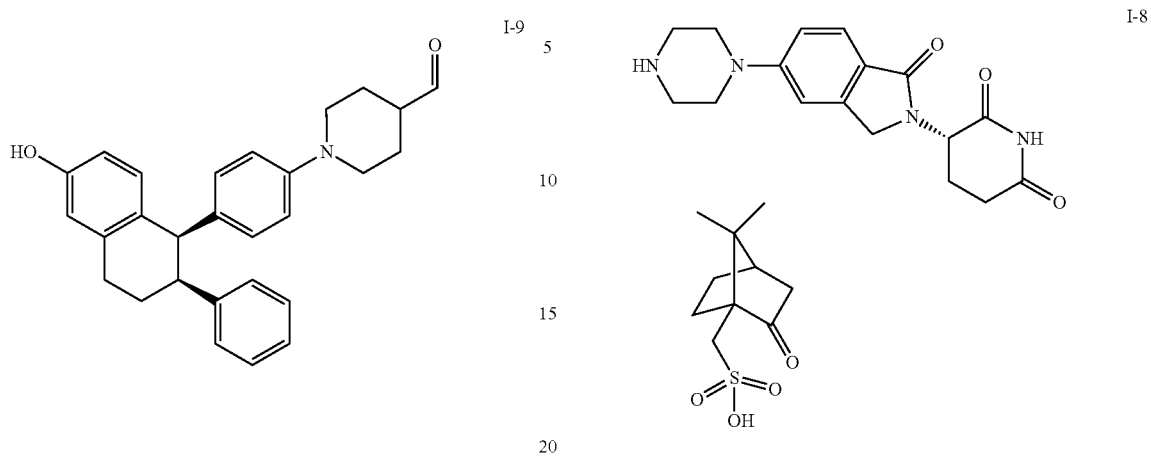

in the presence of a base and a reducing agent to provide Compound 1:

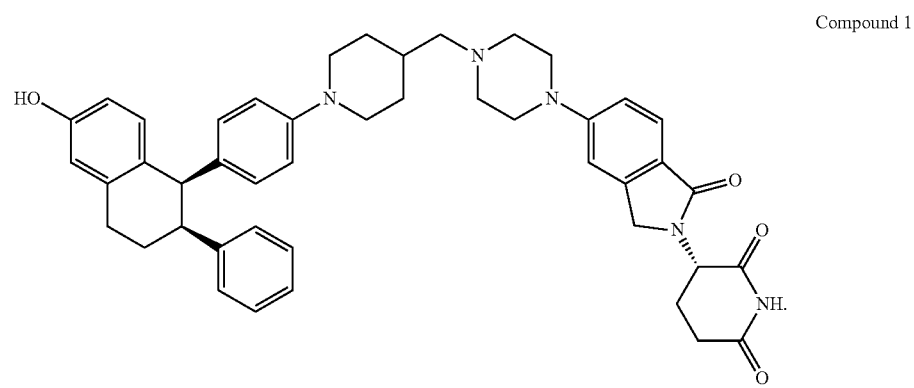 [SMILES: O=C1CC[C@H](N2Cc3cc(N4CCN(CC5CCN(c6ccc([C@@H]7c8ccc(O)cc8CC[C@@H]7c7ccccc7)cc6)CC5)CC4)ccc3C2=O)C(=O)N1]

DETAILED DESCRIPTION

In one aspect, the present disclosure is directed to methods for preparing Compound 1.

In some embodiments, the methods for preparing Compound 1 comprises providing a mixture comprising Intermediate I-9, salt Intermediate I-8, a base, and a reducing agent to reductively aminate Intermediate I-9 with salt Intermediate I-8 to provide Compound 1:

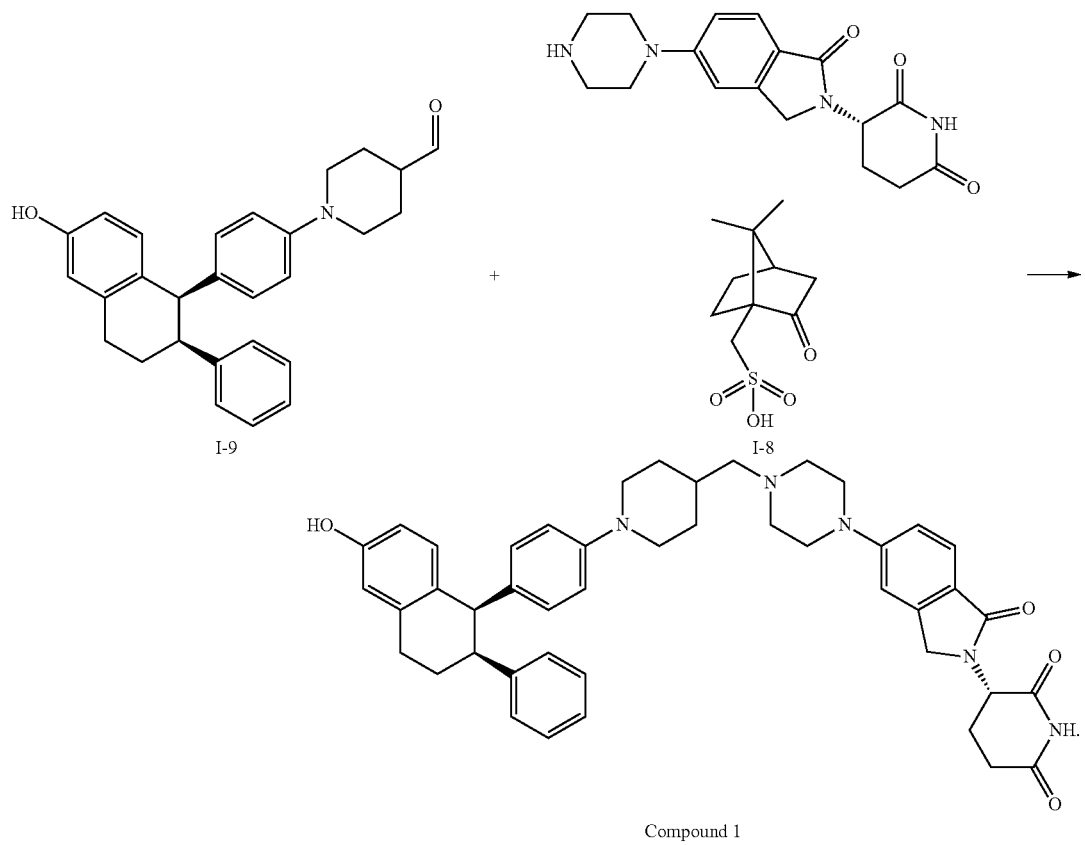

Compound 1

In some embodiments, the base used in the methods for preparing Compound 1 is an amine base or a carbonate salt.

In some embodiments, the base used in the methods for preparing Compound 1 is an amine base.

In some embodiments, the base used in the methods for preparing Compound 1 is N-methyl-morpholine.

In some embodiments, the base used in the methods for preparing Compound 1 is trimethylamine.

In some embodiments, the base used in the methods for preparing Compound 1 is triethylamine.

In some embodiments, the base used in the methods for preparing Compound 1 is, N,N-diisopropylethylamine.

In some embodiments, the base used in the methods for preparing Compound 1 is N,N-dimethylaniline.

In some embodiments, the base used in the methods for preparing Compound 1 is a carbonate salt.

In some embodiments, the base used in the methods for preparing Compound 1 is lithium carbonate, sodium carbonate, potassium carbonate, or magnesium carbonate.

In some embodiments, the base used in the methods for preparing Compound 1 lithium carbonate.

In some embodiments, the base used in the methods for preparing Compound 1 sodium carbonate.

In some embodiments, the base used in the methods for preparing Compound 1 is potassium carbonate.

In some embodiments, the base used in the methods for preparing Compound 1 is magnesium carbonate.

In some embodiments, the base used in the methods for preparing Compound 1 is N-methyl-morpholine, trimethylamine, triethylamine, N,N-diisopropylethylamine, N,N-dimethylaniline, lithium carbonate, sodium carbonate, potassium carbonate, or magnesium carbonate.

In some embodiments, the base used in the methods for preparing Compound 1 is present in a ratio of base to salt Intermediate I-8 in the reaction mixture of about 1:1 to about 3:1, preferably about 1:1 to about 2:1.

In some embodiments, the base used in the methods for preparing Compound 1 is present in a molar ratio of base to salt Intermediate I-8 in the reaction mixture of about 1.00:1, about 1.05:1, about 1.10:1, about 1.15:1, about 1.20:1, about 1.25:1, about 1.30:1, about 1.35:1, about 1.40:1, about 1.45:1, about 1.50:1, about 1.55:1, about 1.60:1, about 1.65:1, about 1.70:1, about 1.75:1, about 1.80:1, about 1.85:1, about 1.90:1, about 1.95:1, about 2.00:1, about 2.05:1, about 2.10:1, about 2.15:1, about 2.20:1, about 2.25:1, about 2.30:1, about 2.35:1, about 2.40:1, or about 2.45:1.

In some embodiments, the process for methods Compound 1 comprises providing a mixture comprising a reducing agent.

In some embodiments, the process for methods Compound 1 comprises providing a mixture comprising a reducing agent, wherein the reducing agent is sodium triacetoxyborohydride, sodium borohydride, sodium cyanoborohydride, or hydrogen in the presence of a catalyst.

In some embodiments, the process for methods Compound 1, comprises providing a mixture comprising a reducing agent, wherein the reducing agent is sodium triacetoxyborohydride.

In some embodiments, the methods for preparing Compound 1, comprises providing a mixture comprising a reducing agent, wherein the reducing agent is sodium borohydride.

In some embodiments, the methods for preparing Compound 1, comprises providing a mixture comprising a reducing agent, wherein the reducing agent is sodium cyanoborohydride.

In some embodiments, the methods for preparing Compound 1, comprises providing a mixture comprising a reducing agent, wherein the reducing agent is hydrogen in the presence of a catalyst.

In some embodiments, the reaction mixture used for preparing Compound 1 comprises a molar ratio of reducing agent to salt Intermediate I-8, wherein the reducing agent is present in a molar ratio of reducing agent to salt Intermediate I-8 in the reaction mixture of about 1:1 to about 3:1, preferably about 1:1 to about 2:1.

In some embodiments, the molar ratio of reducing agent to salt Intermediate I-8 in the reaction mixture is about 1.00:1, about 1.05:1, about 1.10:1, about 1.15:1, about 1.20:1, about 1.25:1, about 1.30:1, about 1.35:1, about 1.40:1, about 1.45:1, about 1.50:1, about 1.55:1, about 1.60:1, about 1.65:1, about 1.70:1, about 1.75:1, about 1.80:1, about 1.85:1, about 1.90:1, about 1.95:1, about 2.00:1, about 2.05:1, or about 2.10:1.

In some embodiments, the reaction for preparing Compound 1 is conducted in a polar solvent.

In some embodiments, the reaction for preparing Compound 1 is conducted in a polar solvent, wherein the polar solvent is dimethylacetamide, N-methyl-2-pyrrolidone, or 2-methyl tetrahydrofuran.

In some embodiments, the reaction for preparing Compound 1 is conducted in a polar solvent, wherein the polar solvent is dimethylacetamide.

In some embodiments, the reaction for preparing Compound 1 is conducted in a polar solvent, wherein the polar solvent is N-methyl-2-pyrrolidone.

In some embodiments, the reaction for preparing Compound 1 is conducted in a polar solvent, wherein the polar solvent is 2-methyl tetrahydrofuran.

In some embodiments, the reaction for preparing Compound 1 is conducted at a temperature of about −30° C. to about 30° C., preferably about −10° C. to about 10° C.

In some embodiments, the reaction for preparing Compound 1 is conducted at a temperature of about −30° C., about −25° C., about −20° C., about −15° C., about −10° C., about −5° C., about 0° C., about 5° C., about 10° C., about 15° C., about 20° C., about 25° C., or about 30° C.

In some embodiments, the reaction for preparing Compound 1 is quenched upon completion of the reductive amination reaction, wherein the reaction mixture is quenched by combining the reaction mixture with water.

In some embodiments, the reaction for preparing Compound 1 is quenched upon completion of the reductive amination reaction, wherein the reaction mixture is quenched by combining the reaction mixture with an alcohol.

In some embodiments, the reaction for preparing Compound 1 is quenched upon completion of the reductive amination reaction, wherein the reaction mixture is quenched by combining the reaction mixture with water and an alcohol.

In some embodiments, the reaction for preparing Compound 1 is quenched upon completion of the reductive amination reaction, wherein the reaction mixture is quenched by combining the reaction mixture with a $C_1$-$C_6$ alcohol.

In some embodiments, the reaction for preparing Compound 1 is quenched upon completion of the reductive amination reaction, wherein the reaction mixture is quenched by combining the reaction mixture with ethanol.

In some embodiments, the reaction for preparing Compound 1 is quenched and the quenched reaction mixture is then combined with a solution of an alcohol and water to form a precipitate comprising Compound 1.

In some embodiments, the reaction for preparing Compound 1 is quenched and the quenched reaction mixture is then combined with a solution of ethanol and water, to form a precipitate comprising Compound 1.

In some embodiments, the reaction for preparing Compound 1 is quenched and the quenched reaction mixture is then combined with a solution of alcohol and water, to form a precipitate comprising Compound 1, wherein the temperature of the solution of alcohol and water is about 50° C. to about 90° C., preferably about 60° C. to about 80° C., when the solution of alcohol and water is combined with the quenched reaction mixture. In some embodiments, the alcohol is ethanol.

In some embodiments, the reaction for preparing Compound 1 is quenched and the quenched reaction mixture is then combined with a solution of alcohol and water, to form a precipitate comprising Compound 1, wherein the temperature of the solution of alcohol and water is about 50° C., about 55° C., about 60° C., about 70° C., about 75° C., or about 80° C. when the solution of alcohol and water is combined with the quenched reaction mixture. In some embodiments, the alcohol is ethanol.

In some embodiments, the reaction mixture affording Compound 1 is quenched and the quenched reaction mixture is then combined with a solution of alcohol and water, wherein the solution of alcohol and water added to the quenched reaction mixture has an alcohol:water ratio of about 1:100, about 1:50, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 50:1, or about 100:1 (v:v).

In some embodiments, the process for preparing Compound 1 is quenched and the quenched reaction mixture is then combined with a solution of alcohol and water having an alcohol:water ratio of about 1:1 (v/v).

In some embodiments, the process for preparing Compound 1 comprises cooling the precipitate that forms after the quenched reaction mixture is combined with the solution of alcohol and water.

In some embodiments, the resulting precipitate in the process for preparing Compound 1 is cooled to about 50° C., about 45° C., about 40° C., about 35° C., about 30° C., about 25° C., about 20° C., or about 15° C.

In some embodiments, the resulting precipitate in the process for preparing Compound 1 is filtered.

In some embodiments, the resulting precipitate in the process for preparing Compound 1 is filtered and the filtrate is washed with water and alcohol. In some embodiments, the alcohol used to wash the filtrate is ethanol.

In some embodiments, the alcohol:water ratio used for washing the filtrate is the same as the alcohol:water ratio added to the quenched reaction mixture.

In some embodiments, the alcohol:water ratio used for washing the filtrate is different than the alcohol:water ratio added to the quenched reaction mixture.

In some embodiments, the alcohol:water ratio used for washing the filtrate is about 1:100, about 1:50, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 50:1, or about 100:1 (v:v).

Intermediate I-9

In some aspects, disclosed herein are methods for preparing Intermediate I-9.

In some embodiments, the methods for preparing Intermediate I-9, comprise providing a mixture comprising Intermediate I-6, a solvent, and an acid to provide Intermediate I-9:

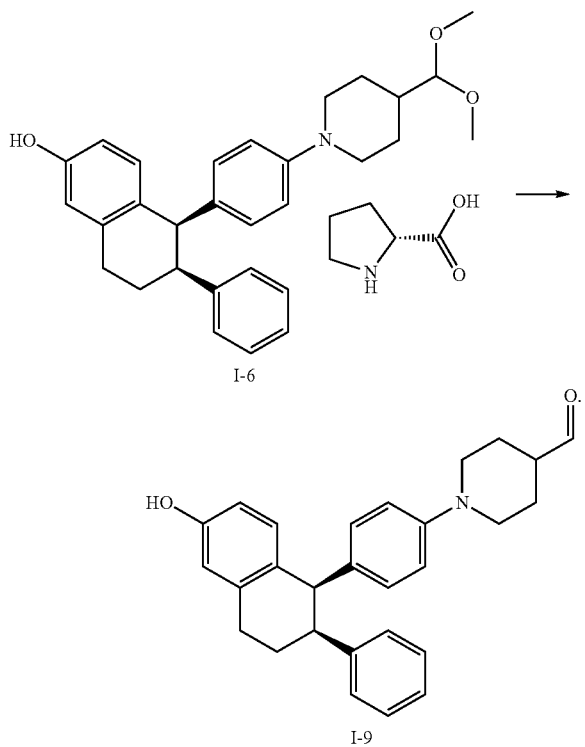

In some embodiments, the reaction mixture in the methods for preparing Intermediate I-9, comprises a solvent, wherein the solvent in the reaction mixture comprises water and an ethereal solvent.

In some embodiments, the reaction mixture in the methods for preparing Intermediate I-9, comprises a solvent, wherein the solvent in the reaction mixture comprises water and 2-methyltetrahydrofuran.

In some embodiments, the reaction mixture in the methods for preparing Intermediate I-9, comprises a solvent, wherein the solvent in the reaction mixture comprises water and tetrahydrofuran.

In some embodiments, the acid used in the methods for preparing Intermediate I-9, is a strong acid.

In some embodiments, the acid used in the methods for preparing Intermediate I-9, is a weak acid.

In some embodiments, the acid used in the methods for preparing Intermediate I-9 is HCL.

In some embodiments, the reaction mixture in the process for preparing Intermediate I-9 further comprises an additive that is an antioxidant, radical scavenger, oxygen scavenger, or metal chelator.

In some embodiments, the reaction mixture in the process for preparing Intermediate I-9 further comprises an additive that is an antioxidant.

In some embodiments, the reaction mixture in the process for preparing Intermediate I-9 further comprises an additive that is a radical scavenger.

In some embodiments, the reaction mixture in the process for preparing Intermediate I-9 further comprises an additive that is an oxygen scavenger.

In some embodiments, the reaction mixture in the process for preparing Intermediate I-9 further comprises an additive that is a metal chelator.

In some embodiments, the reaction mixture in the process for preparing Intermediate I-9 further comprises an additive that is dibutylhydroxytoluene, ascorbic acid, alpha-tocopherol, or ethylenediaminetetraacetic acid.

In some embodiments, the reaction mixture in the process for preparing Intermediate I-9 further comprises an additive that is dibutylhydroxytoluene.

In some embodiments, the reaction mixture in the process for preparing Intermediate I-9 further comprises an additive that is ascorbic acid.

In some embodiments, the reaction mixture in the process for preparing Intermediate I-9 further comprises an additive that is alpha-tocopherol.

In some embodiments, the reaction mixture in the process for preparing Intermediate I-9 further comprises an additive that is ethylenediaminetetraacetic acid.

In some embodiments, the reaction mixture in the process for preparing Intermediate I-9 is at a temperature of about 0° C. to about 40° C., preferably about 10° C. to about 30° C.

In some embodiments, the reaction mixture in the process for preparing Intermediate I-9 is at a temperature of about 0° C., about 5° C., about 10° C., about 15° C., about 20° C., about 25° C., about 30° C., about 35° C., or about 40, or any ranges between any two of the aforementioned temperatures.

In some embodiments, the pH of the reaction mixture in the process for preparing Intermediate I-9 is adjusted, after the reaction is complete.

In some embodiments, the pH of the reaction mixture in the process for preparing Intermediate I-9 is adjusted, after the reaction is complete, to about 7 to about 8.

In some embodiments, the pH of the reaction mixture in the process for preparing Intermediate I-9 is adjusted, after the reaction is complete, to about 7 to about 8 with an aqueous tripotassium phosphate solution.

In some embodiments, the pH of the reaction mixture in the process for preparing Intermediate I-9 is adjusted, after the reaction is complete, to about 7, about 7.1, about 7.2, about 7.3, about 7.4, about 7.5, about 7.6, about 7.7, about 7.8, about 7.9, or about 8.

In some embodiments, to adjust the reaction mixture to an acceptable pH (typically a pH range of about 5.0 to about 9.0, about 5.5 to about 8.5, particularly about 6.0 to about 8.5, about 7.0 to about 8.5, about 7.2 to about 7.7, about 7.1 to about 7.9, or about 7.5 to about 8.0), a pH modifying agent may be used. The pH modifying agent may be a mineral acid or metal hydroxide base selected from the group of potassium hydroxide, sodium hydroxide, and hydrochloric acid, and mixtures thereof, and preferably sodium hydroxide and/or hydrochloric acid. Acidic and/or basic pH modifying agents may be added to adjust the mixture to the target acceptable pH value or range. A buffering agent may be used to stabilize the pH. When used, the buffer can be any appropriate buffer. The buffer may be selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), F-aminocaproic acid, and mixtures thereof.

In some embodiments, the pH of the completed reaction in the process for preparing Intermediate I-9 is adjusted, wherein after adjustment of the pH of the completed reaction, an organic layer and an aqueous layer are formed that are then separated from each other. The aqueous layer is extracted with an ethereal solvent, preferably 2-methyltetrahydrofuran, to form an organic extract that is then concentrated.

In some embodiments, the organic extract comprising Intermediate I-9 is concentrated under vacuum at a temperature of about 20° C. to about 70° C., preferably at about 35° C. to about 55° C.

In some embodiments, the organic extract comprising Intermediate I-9 is concentrated under vacuum at a temperature of about 20° C., about 25° C., about 30° C., about 35° C., about 40° C., about 45° C., about 50° C., about 55° C., about 60° C., about 65° C., about 70° C., or any ranges between any two of the preceding values.

In some embodiments, the organic extract comprising Intermediate I-9 is concentrated and the concentrated organic extract is combined with dimethylacetamide and re-concentrated under vacuum.

In some embodiments, after the re-concentration of the organic extract and dimethylacetamide under vacuum, the molar ratio of ethereal solvent relative to Intermediate I-9 in the re-concentrated organic extract is about 0.1:1 or less, about 0.09:1 or less, about 0.08:1 or less, about 0.07:1 or less, about 0.06:1 or less, about 0.05:1 or less, about 0.04:1 or less, about 0.03:1 or less, about 0.02:1 or less, about 0.01:1 or less.

In some embodiments, after the re-concentration of the organic extract and dimethylacetamide under vacuum, the molar ratio of ethereal solvent relative to Intermediate I-9 in the re-concentrated organic extract is about 0.1:1 or less.

In some embodiments, after the re-concentration of the organic extract and dimethylacetamide under vacuum, the molar ratio of ethereal solvent, preferably 2-methyltetrahydrofuran, relative to Intermediate I-9 in the re-concentrated organic extract is about 0.1:1 or less.

Intermediate I-6

In some aspects, disclosed herein are methods for preparing Intermediate I-6, wherein the methods comprise:

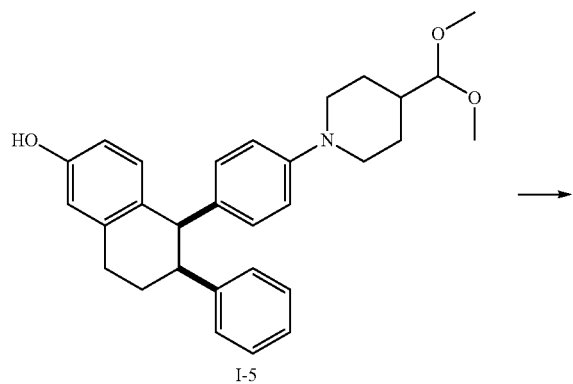

I-5

-continued

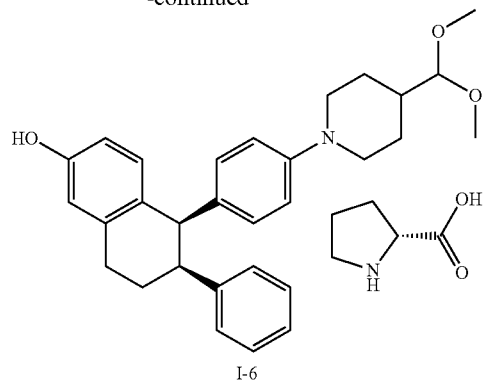

I-6

(a) combining racemic Intermediate I-5 and an additive with solvent to prepare a first reaction mixture;
(b) heating the first reaction mixture at reflux to prepare a first solution, followed by cooling the first solution to a temperature of about 50° C. to about 100° C., preferably about 65° C. to about 75° C.;
(c) combining (R)-proline and water to prepare a second solution, wherein the molar ratio of (R)-proline to the total amount of Intermediate I-5 is about 0.40:1 to about 1.00:1;
(d) adding about 1% to less than about 50% by volume, preferably about 5% to about 25% by volume, of the second solution to the first solution to prepare a second reaction mixture;
(e) adding a first amount of an agent that induces nucleation to the second reaction mixture to prepare a third reaction mixture;
(f) adding about 1% to less than about 50% by volume, preferably about 5% to about 25% by volume, of the second solution to the third reaction mixture to prepare a fourth reaction mixture;
(g) adding a second amount of the agent that induces nucleation to the fourth reaction mixture to prepare a fifth reaction mixture; and
(h) adding the remainder of the second solution to the fifth reaction mixture to prepare a sixth reaction mixture comprising Intermediate I-6.

In some embodiments, the first reaction mixture is heated to prepare a first solution. In some embodiments, the first solution is cooled to a temperature of about 50° C. to about 55° C., about 55° C. to about 60° C., about 60° C. to about 65° C., about 65° C. to about 70° C., about 70° C. to about 75° C., about 75° C. to about 80° C., about 80° C. to about 85° C., about 85° C. to about 90° C., about 90° C. to about 95° C., about 95° C. to about 100° C., or is selected from any range between any two of the preceding values.

In some embodiments, the first reaction mixture is heated to prepare a first solution. In some embodiments, the first solution is cooled to a temperature of about 65° C. to about 75° C.

In some embodiments, step (c) comprises combining (R)-proline and water to prepare a second solution, wherein the molar ratio of (R)-proline to the total amount of Intermediate I-5 is about 0.4:1, about 0.5:1, about 0.6:1, about 0.7:1, about 0.8:1, about 0.9:1 or about 1.0:1.

In some embodiments, step (c) comprises combining (R)-proline and water to prepare a second solution wherein the ratio of (R)-proline:water in the second solution is about 1:10 (w/v), about 1:9 (w/v), about 1:8 (w/v), about 1:7 (w/v), about 1:6 (w/v), about 1:5 (w/v), about 1:4 (w/v), about 1:3

(w/v), about 1:2 (w/v), about 1:1 (w/v), about 2:1 (w/v), about 3:1 (w/v), about 4:1 (w/v), about 5:1 (w/v), about 6:1 (w/v), about 7:1 (w/v), about 8:1 (w/v), about 9:1 (w/v), or about 10:1 (w/v).

In some embodiments, step (d) comprises adding about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45% or less than about 50% by volume of the second solution to the first solution to prepare a second reaction mixture.

In some embodiments, step (d) comprises adding about 5% to about 25% by volume of the second solution to the first solution to prepare a second reaction mixture.

In some embodiments, step (e) comprises adding a first amount of an agent that induces nucleation to the second reaction mixture to prepare a third reaction mixture.

In some embodiments, step (f) comprises adding about 1% to less than about 50% by volume, preferably about 5% to about 25% by volume, of the second solution to the third reaction mixture to prepare a fourth reaction mixture;

In some embodiments, step (g) comprises adding a second amount of the agent that induces nucleation to the fourth reaction mixture to prepare a fifth reaction mixture.

In some embodiments, step (h) comprises adding the remainder of the second solution to the fifth reaction mixture to prepare a sixth reaction mixture comprising Intermediate I-6.

In some embodiments, the solvent in the first reaction mixture for the process for preparing Intermediate I-6 comprises a mixture of alcoholic and ethereal solvents.

In some embodiments, the solvent in the first reaction mixture for the process for preparing Intermediate I-6 comprises a mixture of alcoholic and ethereal solvents, wherein the alcoholic solvents comprise one or more of methanol, ethanol, 1-propanol, 2-propanol, 1-butanol, 2-butanol, 2-methyl-1-propanol and/or 2-methyl-2-butanol.

In some embodiments, the solvent in the first reaction mixture for the process for preparing Intermediate I-6 comprises a mixture of 2-propanol and 2-methyl-tetrahydrofuran.

In some embodiments, the process for preparing Intermediate I-6 comprises adding an agent that induces nucleation. In some embodiments, the agent that induces nucleation is a crystallization promoter. In some embodiments, the crystallization promoter is a seed crystal comprising Intermediate I-6.

In some embodiments, the crystallization promoter is added in one or more portions. In some embodiments, the crystallization promoter is added in one, two, three, four, or five portions. In some embodiments, the crystallization promoter is added in equal amounts across all portions. In some embodiments, the crystallization promoter is added in different amounts across all portions. In some embodiments, the crystallization promoter is added in 2 portions with about 50% added followed by about 50% added. In some embodiments, the crystallization promoter is added in 2 portions with about 25% added followed by about 75%. In some embodiments, the crystallization promoter is added in 2 portions with about 75% added followed by about 25%. In some embodiments, the crystallization promoter is added in 3 portions with about 33% added followed by about 33%, and further followed by about 33%. In some embodiments, the crystallization promoter is added in 3 portions with about 1-25% added followed by about 1-33%, further followed by about 1-65%. In some embodiments, the crystallization promoter is added in 3 portions with about 1-65% added followed by about 1-33%, further followed by about 1-25%. In some embodiments, the crystallization promoter is added in 4 portions with about 25% added in each portion. In some embodiments, the crystallization promoter is added in 4 unequal portions. In some embodiments, the crystallization promoter is added in 5 portions with about 20% added in each portion. In some embodiments, the crystallization promoter is added in 5 unequal portions.

In some embodiments, crystallization is achieved using any technique known in the art.

In some embodiments, the methods for preparing Intermediate I-6 comprise adding a crystallization promoter, wherein the molar ratio of the total amount of the crystallization promoter compared to Intermediate I-6 is about 0.0001:1 to about 0.01:1, and preferably the molar ratio is about 0.0005:1 to about 0.005:1.

In some embodiments, the methods for preparing Intermediate I-6 comprise adding a crystallization promoter, wherein the molar ratio of the total amount of the crystallization promoter compared to Intermediate I-6 is about 0.0001:1, about 0.0002:1, about 0.0003:1, about 0.0004:1, about 0.0005:1, about 0.0006:1, about 0.0007:1, about 0.0008:1, about 0.0009:1, about 0.0010:1, about 0.0011:1, about 0.0012:1, about 0.0013:1, about 0.0014:1, about 0.0015:1, about 0.0016:1, about 0.0017:1, about 0.0018:1, about 0.0019:1, about 0.0020:1, about 0.0021:1, about 0.0022:1, about 0.0023:1, about 0.0024:1, about 0.0025:1, about 0.0030:1, about 0.0035:1, about 0.0040:1, about 0.0045:1, about 0.0050:1, about 0.0055:1, or about 0.0060:1, or is selected from any range between any two of the preceding values.

In some embodiments, the methods for preparing Intermediate I-6 comprise including an additive in the reaction mixture, wherein the additive is an antioxidant, radical scavenger, oxygen scavenger, or metal chelator.

In some embodiments, the methods for preparing Intermediate I-6 comprise including an additive in the reaction mixture, wherein the additive is dibutylhydroxytoluene, ascorbic acid, alpha-tocopherol, or ethylenediaminetetraacetic acid.

In some embodiments, the methods for preparing Intermediate I-6 comprise including an additive in the reaction mixture, wherein the additive is dibutylhydroxytoluene.

In some embodiments, the methods for preparing Intermediate I-6 comprise including an additive in the reaction mixture, wherein the additive is ascorbic acid.

In some embodiments, the methods for preparing Intermediate I-6 comprise including an additive in the reaction mixture, wherein the additive is alpha-tocopherol.

In some embodiments, the methods for preparing Intermediate I-6 comprise including an additive in the reaction mixture, wherein the additive is ethylenediaminetetraacetic acid.

In some embodiments, in the methods for preparing Intermediate I-6 the molar ratio of the total amount of (R)-proline used in the methods to the total amount of Intermediate I-5 used in the process is about 0.40:1 to about 0.90:1, preferably about 0.50:1 to about 0.75:1.

In some embodiments, in the methods for preparing Intermediate I-6 the molar ratio of the total amount of (R)-proline used in the methods to the total amount of Intermediate I-5 used in the process is about 0.50:1, about 0.51:1, about 0.52:1, about 0.53:1, about 0.54:1, about 0.55:1, about 0.56:1, about 0.57:1, about 0.58:1, about 0.59:1, about 0.60:1, about 0.61:1, about 0.62:1, about 0.63:1, about 0.64:1, about 0.65:1, about 0.66:1, about 0.67:1, about 0.68:1, about 0.69:1, or about 0.70:1.

In some embodiments, in the methods for preparing Intermediate I-6 the molar ratio of the total amount of (R)-proline used in the process to the total amount of Intermediate I-5 used in the process is about 0.50:1, about 0.51:1, about 0.52:1, about 0.53:1, about 0.54:1, about 0.55:1, about 0.56:1, about 0.57:1, about 0.58:1, about 0.59:1, about 0.60:1, about 0.61:1, about 0.62:1, about 0.63:1, about 0.64:1, about 0.65:1, about 0.66:1, about 0.67:1, about 0.68:1, about 0.69:1, about 0.70:1, about 0.71:1, about 0.72:1, about 0.73:1, about 0.74:1, about 0.75:1, about 0.76:1, about 0.77:1, about 0.78:1, about 0.79:1, about 0.80:1, about 0.81:1, about 0.82:1, about 0.83:1, about 0.84:1, about 0.85:1, about 0.86:1, about 0.87:1, about 0.88:1, about 0.89:1, about 0.90:1, about 0.91:1, about 0.92:1, about 0.93:1, about 0.94:1, about 0.95:1, about 0.96:1, about 0.97:1, about 0.98:1, about 0.99:1, about 1.00:1, about 1.1:1, about 1.2:1, about 1.3:1, about 1.4:1, or about 1.5:1.

In some embodiments in the methods for preparing Intermediate I-6, upon completion of the reaction, the completed reaction is cooled from a temperature of between about 50° C. and about 100° C., between about 50° C. and about 60° C., between about 60° C. and about 70° C., between about 70° C. and about 80° C., between about 80° C. and about 90° C. or between about 90° C. and about 100° C. or any ranges between any two of the preceding values.

In some embodiments in the methods for preparing Intermediate I-6, upon completion of the reaction, the completed reaction is cooled from a temperature of about 50° C. to about 100° C. to a temperature of about 25° C. at a constant rate of temperature change over a period of at least about 15 minutes, at least about 30 minutes, at least about 60 minutes, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, or at least about 12 hours.

In some embodiments, in the methods for preparing Intermediate I-6, upon completion of cooling the completed reaction, the Intermediate I-6 is recovered by filtration, washed with solvent, and dried.

In some embodiments, in the methods for preparing Intermediate I-6, upon completion of cooling the completed reaction, the Intermediate I-6 is recovered by filtration and washed with an alcohol.

In some embodiments, in the methods for preparing Intermediate I-6, upon completion of cooling the completed reaction, the Intermediate I-6 is recovered by filtration, washed with 2-propanol and dried.

In some embodiments, the Intermediate I-6 is dried under vacuum.

In some embodiments, the Intermediate I-6 is dried under vacuum at a temperature of about 30° C., about 35° C., about 40° C., about 45° C., about 50° C., about 55° C., about 60° C. or is selected from any range between any two of the preceding values.

In some embodiments, the Intermediate I-6 is dried under vacuum at a temperature of about 40° C. to about 50° C.

Intermediate I-6A

In some aspects, provided herein are methods Intermediate I-6A, wherein the methods comprise providing Intermediate I-5 and performing chiral supercritical chromatography to obtain Intermediate I-6A.

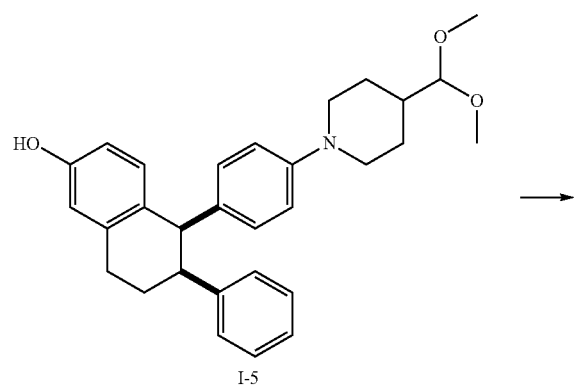

I-5

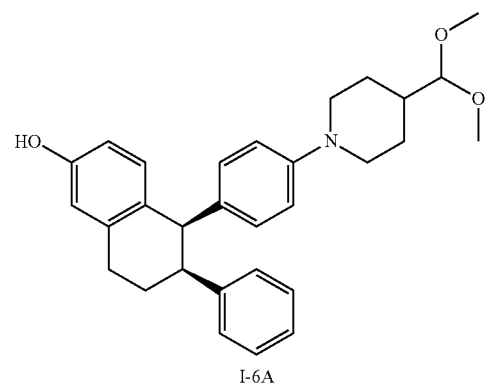

I-6A

In some embodiments, Intermediate I-6A can be substituted for Intermediate I-6 in the preparation of Intermediate I-9 in the methods to prepare Compound 1.

In some embodiments, the methods for preparing Intermediate I-9, comprise providing a mixture comprising Intermediate I-6A, solvent, and an acid to provide Intermediate I-9:

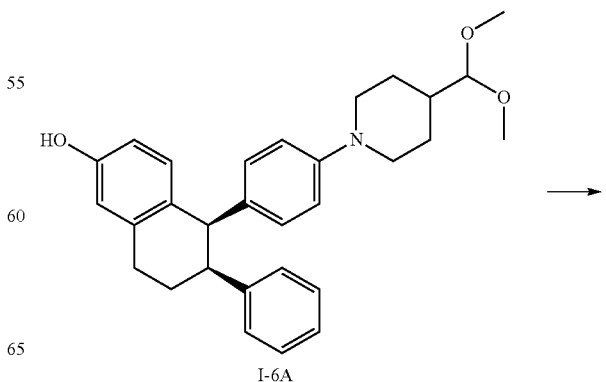

I-6A

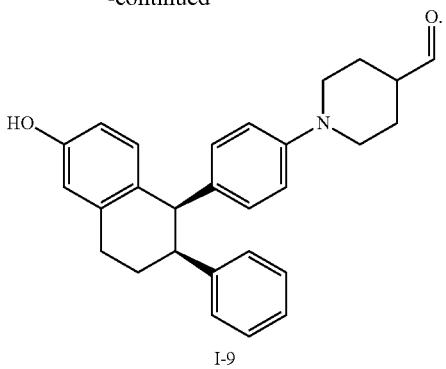

I-9

Intermediate I-8

In some aspects, disclosed herein are methods for preparing salt Intermediate I-8, comprising providing a mixture comprising Intermediate I-4, camphorsulfonic acid, and a solvent to provide salt Intermediate I-8

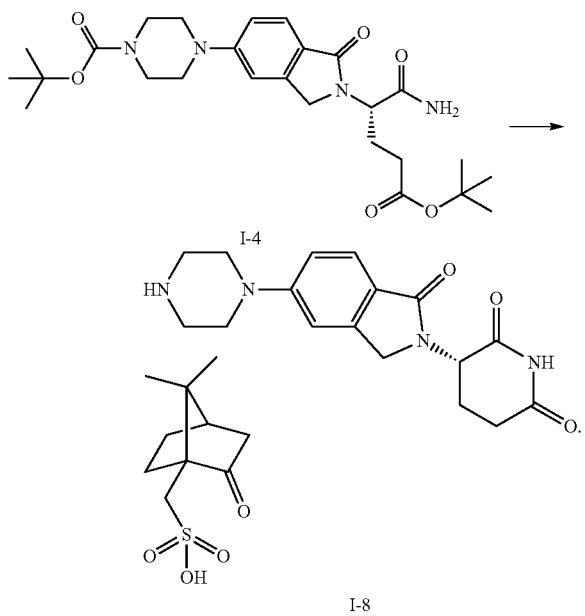

In some embodiments, the molar ratio of camphorsulfonic acid to Intermediate I-4 in the reaction mixture is about 1:1 to about 5:1, about 1:1 to about 4:1, about 1:1 to about 3:1, or about 1:1 to about 2:1.

In some embodiments, the molar ratio of camphorsulfonic acid to Intermediate I-4 in the reaction mixture is about 1.5:1 to about 2.5:1.

In some embodiments, the molar ratio of camphorsulfonic acid to Intermediate I-4 in the reaction mixture is about 1:1 to about 3:1, preferably about 1.5:1 to about 2.5:1.

In some embodiments, the molar ratio of camphorsulfonic acid to Intermediate I-4 in the reaction mixture is about 1.50:1, about 1.55:1, about 1.60:1, about 1.65:1, about 1.70:1, about 1.75:1, about 1.80:1, about 1.85:1, about 1.90:1, about 1.95:1, about 2.00:1, about 2.05:1, about 2.10:1, about 2.15:1, about 2.20:1, about 2.25:1, about 2.30:1, about 2.35:1, about 2.40:1, about 2.45:1, about 2.50:1 or any range between any two of the preceding values.

In some embodiments, the camphorsulfonic acid in the reaction mixture is (+)-camphorsulfonic acid.

In some embodiments, the solvent comprises acetonitrile.

In some embodiments, the solvent comprises dimethylformamide.

In some embodiments, the solvent comprises a mixture of acetonitrile and dimethylformamide.

In some embodiments, the solvent comprises acetonitrile, dimethylformamide, or a mixture thereof.

In some embodiments, the solvent comprises acetonitrile and dimethylformamide in a ratio of about 10:1 (v/v), about 9:1 (v/v), about 8:1 (v/v), about 7:1 (v/v), about 6:1 (v/v), about 5:1 (v/v), about 4:1 (v/v), about 3:1 (v/v), about 2:1 (v/v), about 1:1 (v/v), about 1:2 (v/v), about 1:3 (v/v), about 1:4 (v/v), about 1:5 (v/v), about 1:6 (v/v), about 1:7 (v/v), about 1:8 (v/v), about 1:9 (v/v), about 1:10 (v/v).

In some embodiments, the solvent comprises acetonitrile and dimethylformamide in a ratio of about 1:1 (v/v) to about 8:1 (v/v), preferably about 2:1 (v/v) to about 6:1 (v/v).

In some embodiments, the reaction to prepare Intermediate I-8 is conducted at a temperature of about 70° C. to about 100° C., preferably about 85° C. to about 100° C.

In some embodiments, the reaction to prepare Intermediate I-8 is conducted at a temperature of about 70° C., about 75° C., about 80° C., about 85° C., about 90° C., about 95° C., or about 100° C.

In some embodiments, the reaction to prepare Intermediate I-8 is conducted at a temperature of about 85° C. to about 100° C.

In some embodiments, the reaction to prepare Intermediate I-8 is conducted at a temperature of about 90° C., about 95° C., or about 100° C.

In some embodiments, the reaction to prepare Intermediate I-8 is conducted under conditions to promote the azeotropic removal of the solvent and one or more byproducts of the reaction from the reaction mixture. In some embodiments, the one or more byproducts of the reaction that are azeotropically removed from the reaction mixture comprise water and tert-butanol.

Intermediate I-4

In some aspects, disclosed herein are methods for preparing Intermediate I-4 comprising providing a mixture comprising Intermediate I-3, Intermediate I-3A, and a solvent, to which is added a reducing agent under reaction conditions, to provide Intermediate I-4:

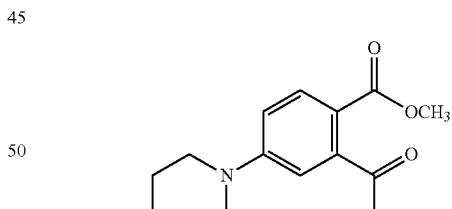

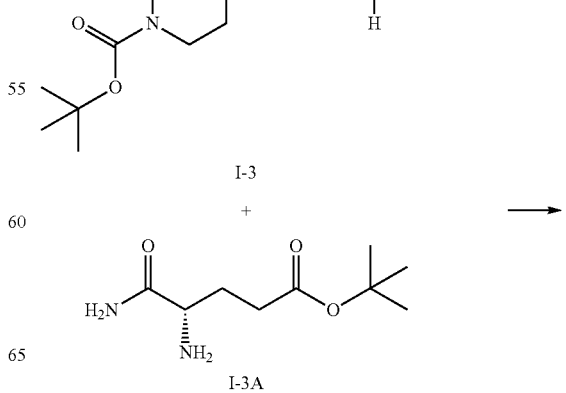

-continued

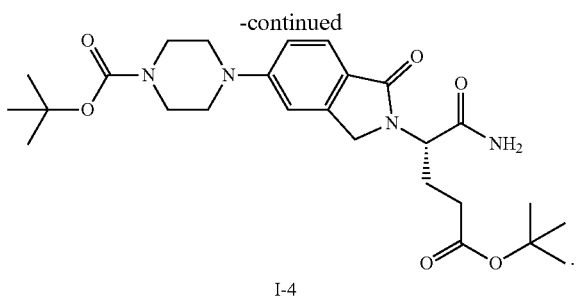

I-4

In some embodiments, the solvent in the methods for preparing Intermediate I-4 comprises a protic solvent.

In some embodiments, the solvent in the methods for preparing Intermediate I-4 comprises a $C_1$-$C_6$ alcohol.

In some embodiments, the solvent in the methods for preparing Intermediate I-4 comprises one or more of methanol, ethanol, 1-propanol, 2-propanol, 1-butanol, 2-butanol, 2-methyl-1-propanol and 2-methyl-2-propanol.

In some embodiments, the solvent in the methods for preparing Intermediate I-4 comprises methanol.

In some embodiments, the solvent in the methods for preparing Intermediate I-4 further comprises an acid, preferably acetic acid.

In some embodiments, the solvent in the methods for preparing Intermediate I-4 further comprises acetic acid.

In some embodiments, the solvent in the methods for preparing Intermediate I-4 comprises one or more of methanol, ethanol, 1-propanol, 2-propanol, 1-butanol, 2-butanol, 2-methyl-1-propanol and/or 2-methyl-2-propanol, wherein the solvent further comprises an acid.

In some embodiments, the solvent in the methods for preparing Intermediate I-4 comprises one or more of methanol, ethanol, 1-propanol, 2-propanol, 1-butanol, 2-butanol, 2-methyl-1-propanol and/or 2-methyl-2-propanol, wherein the solvent further comprises acetic acid.

In some embodiments, the solvent in the methods for preparing Intermediate I-4 comprises methanol, wherein the solvent further comprises acetic acid.

In some embodiments, the reducing agent in the methods for preparing Intermediate I-4 is added to the reaction mixture as a solution in methanol.

In some embodiments, the reducing agent in the methods for preparing Intermediate I-4 is added to the reaction mixture as a solution in an alcohol solvent, wherein the reducing agent is present in about 1% w/w in the alcohol solvent, about 2% w/w in the alcohol solvent, about 3% w/w in the alcohol solvent, about 4% w/w in the alcohol solvent, about 5% w/w in the alcohol solvent, about 6% w/w in the alcohol solvent, about 7% w/w in the alcohol solvent, about 8% w/w in the alcohol solvent, about 9% w/w in the alcohol solvent, about 10% w/w in the alcohol solvent, about 11% w/w in the alcohol solvent, about 12% w/w in the alcohol solvent, about 13% w/w in the alcohol solvent, about 14% w/w in the alcohol solvent, about 15% w/w in the alcohol solvent, about 16% w/w in the alcohol solvent, about 16.1% w/w in the alcohol solvent, about 16.2% w/w in the alcohol solvent, about 16.3% w/w in the alcohol solvent, about 16.4% w/w in the alcohol solvent, about 16.5% w/w in the alcohol solvent, about 16.6% w/w in the alcohol solvent, about 16.7% w/w in the alcohol solvent, about 16.8% w/w in the alcohol solvent, about 16.9% w/w in the alcohol solvent, about 17% w/w in the alcohol solvent, about 18% w/w in the alcohol solvent, about 19% w/w in the alcohol solvent, about 20% w/w in the alcohol solvent, about 21% w/w in the alcohol solvent, about 22% w/w in the alcohol solvent, about 23% w/w in the alcohol solvent, about 24% w/w in the alcohol solvent, or about 25% w/w in the alcohol solvent.

In some embodiments, the reducing agent in the methods for preparing Intermediate I-4 is added to the reaction mixture as a solution in an alcohol solvent, wherein the reducing agent is sodium cyanoborohydride and is present in about 1% w/w in the alcohol solvent, about 2% w/w in the alcohol solvent, about 3% w/w in the alcohol solvent, about 4% w/w in the alcohol solvent, about 5% w/w in the alcohol solvent, about 6% w/w in the alcohol solvent, about 7% w/w in the alcohol solvent, about 8% w/w in the alcohol solvent, about 9% w/w in the alcohol solvent, about 10% w/w in the alcohol solvent, about 11% w/w in the alcohol solvent, about 12% w/w in the alcohol solvent, about 13% w/w in the alcohol solvent, about 14% w/w in the alcohol solvent, about 15% w/w in the alcohol solvent, about 16% w/w in the alcohol solvent, about 16.1% w/w in the alcohol solvent, about 16.2% w/w in the alcohol solvent, about 16.3% w/w in the alcohol solvent, about 16.4% w/w in the alcohol solvent, about 16.5% w/w in the alcohol solvent, about 16.6% w/w in the alcohol solvent, about 16.7% w/w in the alcohol solvent, about 16.8% w/w in the alcohol solvent, about 16.9% w/w in the alcohol solvent, about 17% w/w in the alcohol solvent, about 18% w/w in the alcohol solvent, about 19% w/w in the alcohol solvent, about 20% w/w in the alcohol solvent, about 21% w/w in the alcohol solvent, about 22% w/w in the alcohol solvent, about 23% w/w in the alcohol solvent, about 24% w/w in the alcohol solvent, or about 25% w/w in the alcohol solvent.

In some embodiments, the reducing agent in the methods for preparing Intermediate I-4 is added to the reaction mixture as a solution in methanol, wherein the reducing agent is present in about 1% w/w in methanol, about 2% w/w methanol, about 3% w/w methanol, about 4% w/w in methanol, about 5% w/w in methanol, about 6% w/w in methanol, about 7% w/w in methanol, about 8% w/w in methanol, about 9% w/w in methanol, about 10% w/w in methanol, about 11% w/w in methanol, about 12% w/w in methanol, about 13% w/w in methanol, about 14% w/w in methanol, about 15% w/w methanol, about 16% w/w in methanol, about 17% w/w in methanol, about 18% w/w in methanol, about 19% w/w in methanol, or about 20% w/w in methanol.

In some embodiments, the reducing agent in the methods for preparing Intermediate I-4 is added to the reaction mixture as a solution in methanol, wherein the reducing agent is sodium cyanoborohydride and is present in about 1% w/w in methanol, about 2% w/w methanol, about 3% w/w methanol, about 4% w/w in methanol, about 5% w/w in methanol, about 6% w/w in methanol, about 7% w/w in methanol, about 8% w/w in methanol, about 9% w/w in methanol, about 10% w/win methanol, about 11% w/w in methanol, about 12% w/win methanol, about 13% w/w in methanol, about 14% w/w in methanol, about 15% w/w methanol, about 16% w/w in methanol, about 17% w/w in methanol, about 18% w/w in methanol, about 19% w/w in methanol, or about 20% w/w in methanol.

In some embodiments, the reducing agent in the methods for preparing Intermediate I-4 is added to the reaction mixture as a solution in methanol, wherein the reducing agent is sodium cyanoborohydride and is present from about 1% w/w to about 5% w/w in methanol, from about 5% w/w to about 10% w/w in methanol, from about 10% w/w to about 15% w/w in methanol, or from about 15% w/w to about 20% w/w in methanol.

In some embodiments, the reducing agent used in the methods for preparing Intermediate I-4 is added to the reaction mixture as a solution in methanol, wherein the reducing agent is sodium cyanoborohydride and is present from about 1% w/w to about 10% w/w in methanol, or from about 5% w/w to about 15% w/w in methanol, or from about 10% w/w to about 20% w/w in methanol.

In some embodiments, in the methods for preparing Intermediate I-4, before starting the addition of the reducing agent solution to the reaction mixture, the reaction mixture is cooled to a temperature of about 0° C. to about 30° C., In some embodiments, in the methods for preparing Intermediate I-4, before starting the addition of the reducing agent solution to the reaction mixture, the reaction mixture is cooled to a temperature of about 0° C., about 5° C., about 10° C., about 15° C., about 20° C., about 25° C., or about 30° C.

In some embodiments, in the methods for preparing Intermediate I-4, before starting the addition of the reducing agent solution to the reaction mixture, the reaction mixture is cooled to a temperature of about 0° C. to about 10° C., In some embodiments, in the methods for preparing Intermediate I-4, before starting the addition of the reducing agent solution to the reaction mixture, the reaction mixture is cooled to a temperature of about 0° C. to about 30° C., and the reaction mixture temperature is maintained at said temperature throughout the addition of the reducing agent solution.

In some embodiments, in the methods for preparing Intermediate I-4, before starting the addition of the reducing agent solution to the reaction mixture, the reaction mixture is cooled to a temperature of about 0° C., about 5° C., about 10° C., about 15° C., about 20° C., about 25° C., or about 30° C., and the reaction mixture temperature is maintained at said temperature throughout the addition of the reducing agent solution.

In some embodiments, in the methods for preparing Intermediate I-4, before starting the addition of the reducing agent solution to the reaction mixture, the reaction mixture is cooled to a temperature of about 0° C. to about 10° C., and the reaction mixture temperature is maintained at said temperature throughout the addition of the reducing agent solution.

In some embodiments, in the methods for preparing Intermediate I-4, upon completion of the addition of the reducing agent solution to the reaction mixture, the reaction mixture is heated to a temperature of about 15° C., about 20° C., about 25° C., about 30° C., about 35° C., or about 40° C.

In some embodiments, in the methods for preparing Intermediate I-4, upon completion of the addition of the reducing agent solution to the reaction mixture, the reaction mixture is heated to a temperature of about 20° C. to about 30° C.

In some embodiments, the reducing agent used in the methods for preparing Intermediate I-4 is sodium triacetoxyborohydride, sodium borohydride, sodium cyanoborohydride, or hydrogen in the presence of a catalyst.

In some embodiments, the reducing agent used in the methods for preparing Intermediate I-4 is sodium triacetoxyborohydride.

In some embodiments, the reducing agent used in the methods for preparing Intermediate I-4 is sodium borohydride.

In some embodiments, the reducing agent used in the methods for preparing Intermediate I-4 is sodium cyanoborohydride.

In some embodiments, the reducing agent used in the methods for preparing Intermediate I-4 is hydrogen in the presence of a catalyst.

Intermediate I-3

In some aspects, disclosed herein are methods for preparing Intermediate I-3, comprising providing a mixture comprising Intermediate I-2, a reducing agent, and a solvent, followed by heating the mixture to provide Intermediate I-3

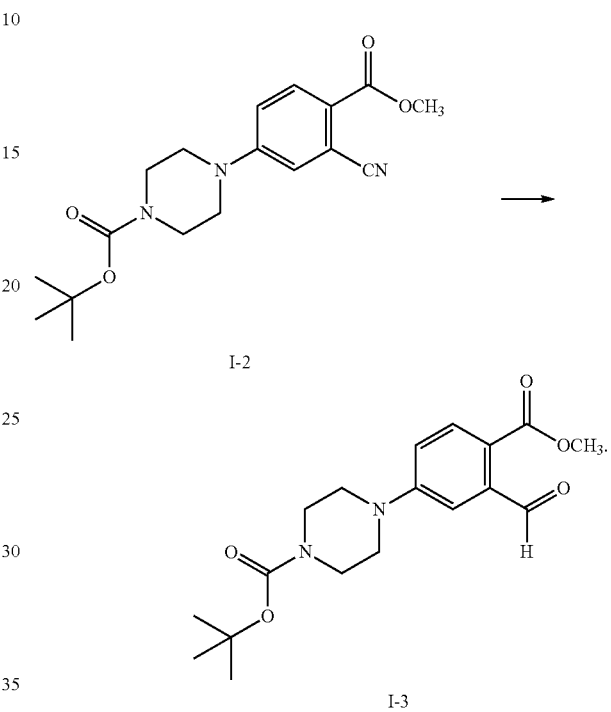

In some embodiments, the solvent for preparing Intermediate I-3 comprises water, an acid, pyridine, or a combination thereof.

In some embodiments, the solvent for preparing Intermediate I-3 comprises water.

In some embodiments, the solvent for preparing Intermediate I-3 comprises water and an acid.

In some embodiments, the solvent for preparing Intermediate I-3 comprises pyridine.

In some embodiments, the solvent for preparing Intermediate I-3 comprises water and pyridine.

In some embodiments, the solvent for preparing Intermediate I-3 comprises an acid.

In some embodiments, the solvent for preparing Intermediate I-3 comprises acetic acid.

In some embodiments, the solvent for preparing Intermediate I-3 comprises water and acetic acid.

In some embodiments, the reducing agent for preparing Intermediate I-3 comprises is Raney nickel.

In some embodiments, the reaction mixture for preparing Intermediate I-3 before heating is at a temperature of about 15° C. to about 30° C.

In some embodiments, the reaction mixture for preparing Intermediate I-3 before heating is at a temperature of about 20° C. to about 30° C.

In some embodiments, the reaction mixture for preparing Intermediate I-3 before heating is at a temperature of about 15° C., about 20° C., about 25° C., about 30° C., about 35° C., or is selected from any range between any two of the preceding values.

In some embodiments, the reaction mixture for preparing Intermediate I-3 before heating is at a temperature of about 25° C.

In some embodiments, the reaction mixture for preparing Intermediate I-3 is heated to a temperature of about 40° C. to about 70° C.

In some embodiments, the reaction mixture for preparing Intermediate I-3 is heated to a temperature of about 50° C. to about 60° C.

In some embodiments, the reaction mixture for preparing Intermediate I-3 is heated to a temperature of about 40° C., about 45° C., about 50° C., about 55° C., about 60° C., about 65° C., about 70° C. or is selected from any range between any two of the preceding values.

Intermediate I-3A

In some aspects, disclosed herein are methods for preparing Intermediate I-3A, comprising providing a mixture comprising Intermediate I-2A, a solvent, and a hydrogen source, under conditions which provide for the hydrogenolysis of Intermediate I-2A to provide Intermediate I-3A

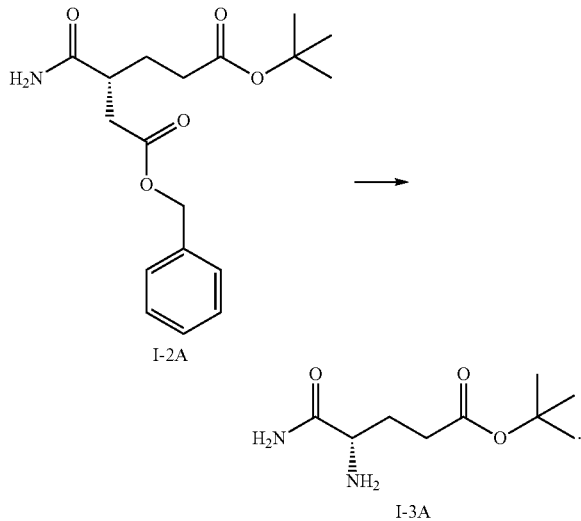

In some embodiments, the reaction mixture in the methods for preparing Intermediate I-3A further comprises a catalyst.

In some embodiments, the reaction mixture in the methods for preparing Intermediate I-3A further comprises a transition metal catalyst.

In some embodiments, the reaction mixture in the methods for preparing Intermediate I-3A further comprises a transition metal catalyst, wherein the transition metal is palladium, rhodium, ruthenium, iridium, or copper.

In some embodiments, the reaction mixture in the methods for preparing Intermediate I-3A further comprises a transition metal catalyst, wherein the transition metal is palladium.

In some embodiments, the reaction mixture in the methods for preparing Intermediate I-3 further comprises a transition metal catalyst, wherein the transition metal is rhodium.

In some embodiments, the reaction mixture in the methods for preparing Intermediate I-3A further comprises a transition metal catalyst, wherein the transition metal is ruthenium.

In some embodiments, the reaction mixture in the methods for preparing Intermediate I-3A further comprises a transition metal catalyst, wherein the transition metal is iridium.

In some embodiments, the reaction mixture in the methods for preparing Intermediate I-3A further comprises a transition metal catalyst, wherein the transition metal is copper.

In some embodiments, the reaction mixture in the methods for preparing Intermediate I-3A further comprises a transition metal catalyst, wherein the catalyst is $Pd(OH)_2$.

In some embodiments, the reaction mixture in the methods for preparing Intermediate I-3A further comprises a hydrogen source, wherein the hydrogen source in the reaction mixture is hydrogen gas.

In some embodiments, the reaction mixture in the methods for preparing Intermediate I-3A further comprises a hydrogen source, wherein the hydrogen source is catalytic transfer hydrogenation.

In some embodiments, the reaction mixture in the methods for preparing Intermediate I-3A further comprises a hydrogen gas, wherein the hydrogen gas in the reaction mixture is maintained at about 0.5 MPa to about 1.5 Mpa.

In some embodiments, the reaction mixture in the methods for preparing Intermediate I-3A further comprises a hydrogen gas, wherein the hydrogen gas in the reaction mixture is maintained at about 0.5 Mpa, about 0.6 Mpa, about 0.7 Mpa, about 0.8 Mpa, about 0.9 Mpa, about 1.0 Mpa, about 1.1 Mpa, about 1.2 Mpa, about 1.3 Mpa, about 1.4 Mpa, or about 1.5 Mpa or is selected from any range between any two of the preceding values.

In some embodiments, the reaction mixture in the methods for preparing Intermediate I-3A further comprises hydrogen gas, wherein the hydrogen gas in the reaction mixture is maintained at about 0.75 Mpa to about 1.25 Mpa.

In some aspects, the methods of preparing Compound 1 comprise preparing Intermediate I-9 by providing a mixture comprising Intermediate I-6, solvent and an acid to provide Intermediate I-9:

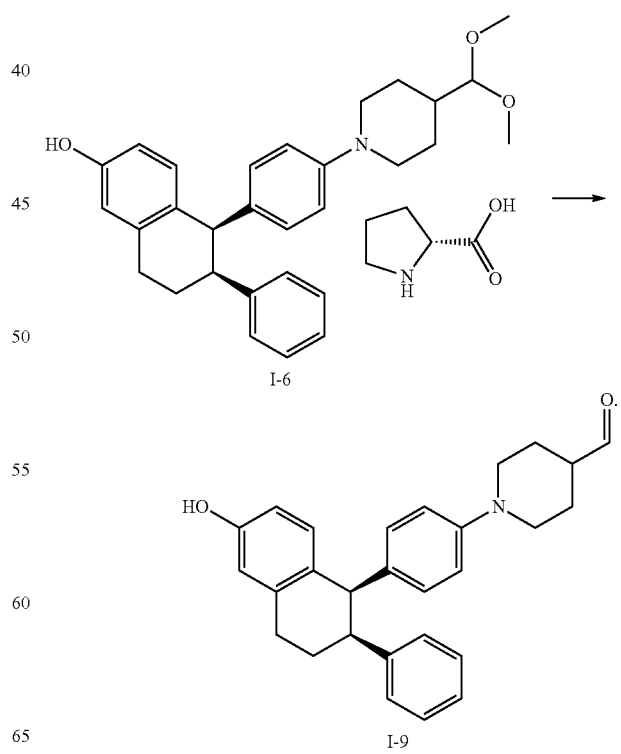

In some aspects, the methods of preparing Compound 1 comprise preparing Intermediate I-6 by:

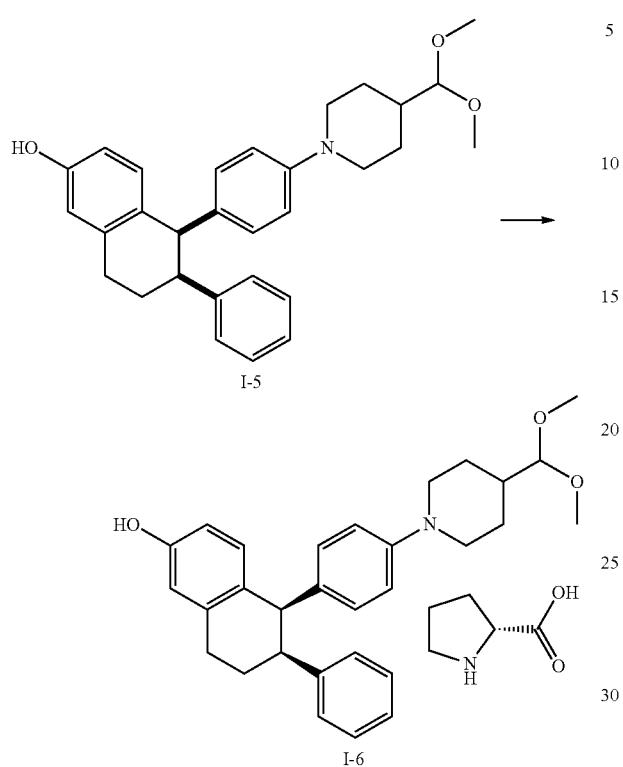

I-5

I-6

(a) combining racemic Intermediate I-5 and an additive with solvent to prepare a first reaction mixture;
(b) heating the first reaction mixture at reflux to prepare a first solution, followed by cooling the first solution to a temperature of about 50° C. to about 100° C., preferably about 65° C. to about 75° C.;
(c) combining (R)-proline and water to prepare a second solution, wherein the molar ratio of the total amount of (R)-proline used in the process to the total amount of Intermediate I-5 used in the process is about 0.40:1 to about 1.00:1;
(d) adding from about 1% to less than about 50% by volume, preferably from about 5% to about 25% by volume, of the second solution to the first solution to prepare a second reaction mixture;
(e) adding a first amount of an agent that induces nucleation to the second reaction mixture to prepare a third reaction mixture;
(f) adding from about 1% to less than about 50% by volume, preferably about 5% to about 25% by volume, of the second solution to the third reaction mixture to prepare a fourth reaction mixture;
(g) adding a second amount of the agent that induces nucleation to the fourth reaction mixture to prepare a fifth reaction mixture; and
(h) adding the remainder of the second solution to the fifth reaction mixture to prepare a sixth reaction mixture comprising Intermediate I-6.

In some aspects, the methods of preparing Compound 1 comprise preparing Intermediate I-8 by providing a mixture comprising Intermediate I-4, camphorsulfonic acid, and a solvent to provide Intermediate I-8

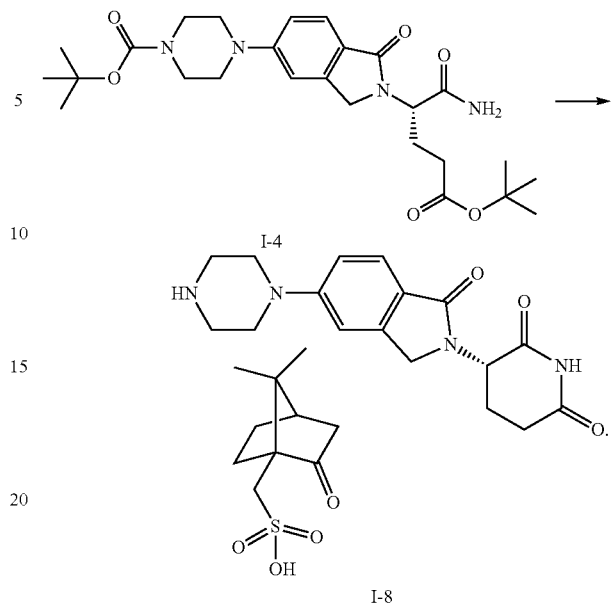

I-4

I-8

In some embodiments, the camphorsulfonic acid is racemic camphorsulfonic acid.
In some embodiments, camphor sulfonic acid is (+)-camphorsulfonic acid.
In some embodiments, the camphorsulfonic acid is (−)-camphorsulfonic acid.
In some embodiments, the methods of preparing Intermediate I-8 comprise adding camphorsulfonic acid which is in a ratio of (+)-camphorsulphonic acid: (−)-camphorsulphonic acid of about 0:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, or about 10:0.

In some aspects, the methods of preparing Compound 1 comprise preparing Intermediate I-4 by providing a mixture comprising Intermediate I-3, Intermediate I-3A, and a solvent, to which is added a reducing agent under reaction conditions to provide Intermediate I-4:

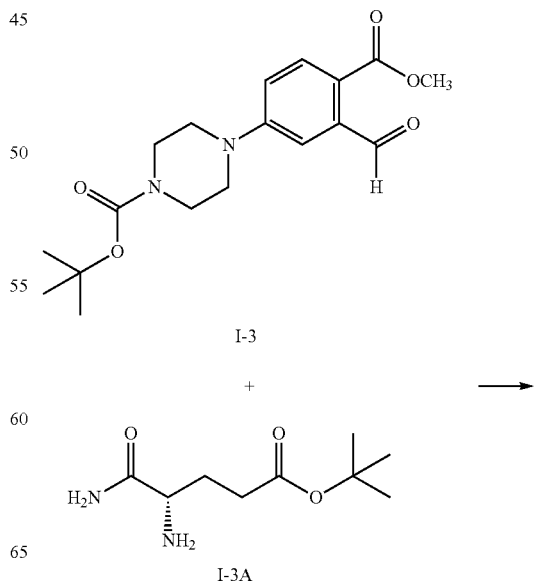

I-3

+

I-3A

-continued

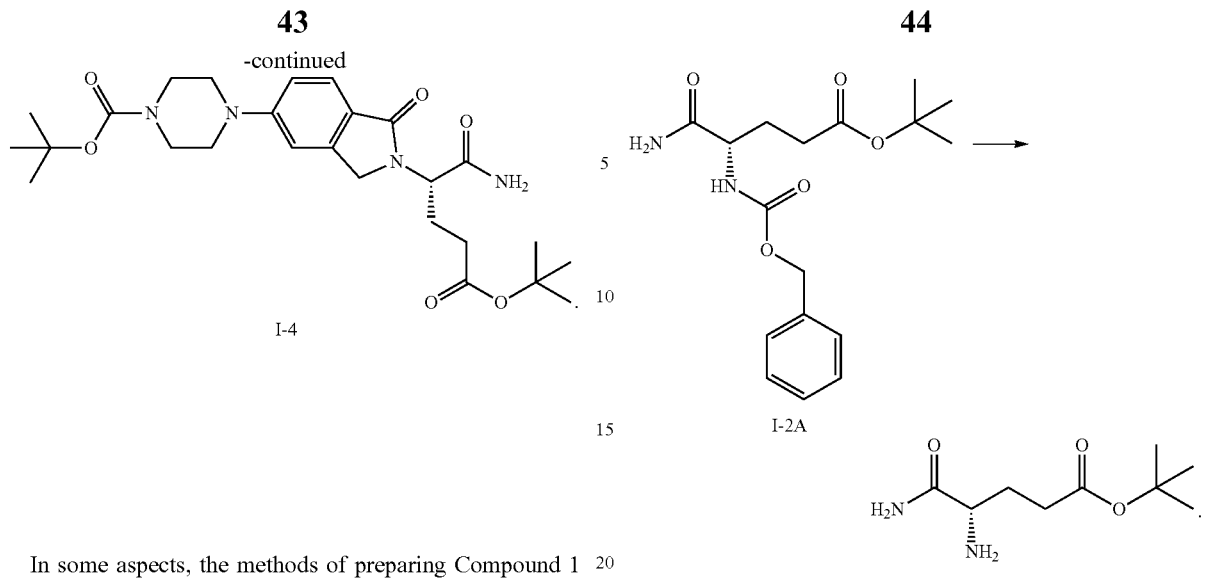

I-4

I-2A

I-3A

In some aspects, the methods of preparing Compound 1 comprise preparing Intermediate I-3 by heating a mixture of Intermediate I-2, a reducing agent, and a solvent, to provide Intermediate I-3

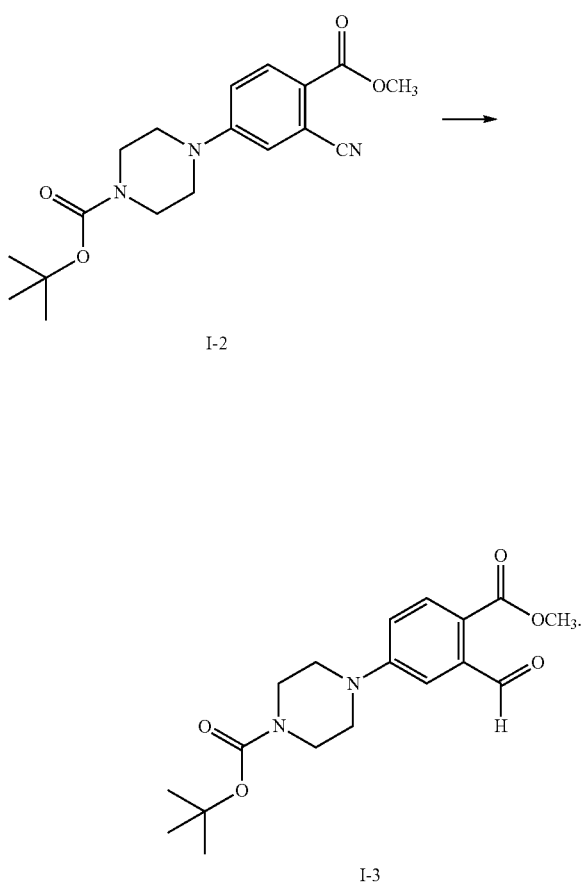

I-2

I-3

In some aspects, the methods of preparing Compound 1 comprise preparing Intermediate I-3A by providing a mixture of Intermediate I-2A, a solvent, and a hydrogen source, under conditions which result in the hydrogenolysis of Intermediate I-2A to provide Intermediate I-3A Definitions Unless otherwise defined, all technical and scientific terms used herein have the same meaning as commonly understood by one of ordinary skill in the art to which this disclosure belongs. The terminology used in this description is intended to describe particular embodiments only and is not intended to limit the disclosure.

Where a range of values is disclosed herein, it is understood that the present disclosure encompasses each intervening value, to the tenth of the unit of the lower limit unless the context clearly dictates otherwise (such as in the case of a group containing a number of carbon atoms; in such cases, each integer falling within the range is provided), from the upper to the lower limit of that range, and any other stated or intervening value in that stated range. As a non-limiting example, the range of 1-10 encompasses each of 1.0, 1.1, 1.2, 1.3, etc. The upper and lower limits of these smaller ranges may independently be included in the smaller ranges, and these are also encompassed within the present disclosure, subject to any specifically excluded limit in the stated range. Where the stated range includes one or both limits, ranges excluding either or both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "both or either" of the elements so conjoined, i.e., elements that are conjunctively present in some cases and disjunctively present in other cases Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also optionally including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "Involving," "holding," "composed of," and the like are to be understood to be open-ended, i.e., to include but not be limited to. Only the transitional phrases "consisting of" and "consisting essentially of" shall be closed or semi-closed transitional phrases, respectively, as set forth in the United States Patent Office Manual of Patent Examining Procedures, Ninth Edition, Revision 10.2019, Section 2111.03.

As used herein in the specification and in the claims, the phrase "at least one," in reference to a list of one or more elements, means at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise As used herein, the term "hydrogenolysis" refers to a chemical reaction whereby a carbon-carbon or carbon-heteroatom single bond is cleaved or undergoes lysis (breakdown) by hydrogen. The heteroatom may vary, but it usually is oxygen, nitrogen, or sulfur. A related reaction is hydrogenation, where hydrogen is added to the molecule, without cleaving bonds. Hydrogenation is a chemical reaction between molecular hydrogen and an element or compound, ordinarily in the presence of a catalyst. The reaction may be one in which hydrogen simply adds to a double or triple bond connecting two atoms in the structure of the molecule or one in which the addition of hydrogen results in dissociation (breaking up) of the molecule (called hydrogenolysis, or destructive hydrogenation). The catalysts most commonly used for hydrogenation reactions are the metals nickel, platinum and palladium and their oxides. For high-pressure hydrogenations, copper chromite and nickel supported on kieselguhr (loose or porous diatomite) may be used.

As used herein, the term "mixture" or "reaction mixture" means a combination of more than one compound, usually within a solvent, that is about to undergo a chemical reaction, is in the process of undergoing a chemical reaction, or has undergone a chemical reaction.

As used herein, the term "reaction" means a process that leads to the chemical transformation of one set of chemical substances to another. As used herein, the term "to react" means to introduce chemical substances together to result in a chemical reaction.

As used herein, the term "cool" or "cooled" or "to cool" means to either passively allow by means of heat dissipation or act by using water or a heat sink (ice, dry ice, etc.) to actively decrease the temperature of an object, mixture, reaction mixture, concentrate, etc.

As used herein, the term "reducing agent" means a compound that loses (or "donates") an electron to an electron recipient (oxidizing agent) in a redox chemical reaction. Reducing agents include those generally known in the art including, for example, sodium hypophosphite ($NaH_2PO_2$), formaldehyde ($CH_2O$) and other aldehydes, formic acid (HCOOH), salts of formic acid, salts of borohydride (e.g., sodium borohydride ($NaBH_4$)), salts of substituted borohydrides (e.g., sodium triacetoxyborohydride ($Na(CH_3CO_2)_3BH$)), sodium alkoxides, lithium aluminum hydride ($LiAlH_4$), diisobutyl aluminum hydride (DIBAH), hydrazine ($H_2NNH_2$), and ammonia. Also used for reduction is catalytic hydrogenation.

As used herein, the term "camphorsulphonic acid" refers to a racemic mixture of camphorsulphonic acid, the pure (+)-camphorsulphonic acid, the pure (−)-camphorsulphonic acid or various ratios of (+)-camphorsulphonic acid: (−)-camphorsulphonic acid, depending on the context.

As used herein, the term "agent that induces nucleation" refers to any object, material or action that results in primary or secondary nucleation. Primary nucleation is the initial formation of a crystal where there are no other crystals present or where, if there are crystals present in the system, they do not have any influence on the crystallization process. This can occur in two conditions. The first is homogeneous nucleation, which is nucleation that is not influenced in any way by solids. These solids include the walls of the crystallizer vessel and particles of any foreign substance. The second category is heterogeneous nucleation, which occurs when solid particles of foreign substances (e.g., any substance that is physically or chemically distinct from the crystals to be formed) cause an increase in the rate of nucleation that would otherwise not occur without the presence of these foreign substances. Homogeneous nucleation rarely occurs in practice due to the high energy necessary to begin nucleation without a solid surface on which to catalyze the nucleation Secondary nucleation is when crystal growth is initiated with contact of other existing crystals or "seeds". The first type of known secondary crystallization is attributable to fluid shear. The second type is due to collisions between already existing crystals with either a solid surface of the crystallizer or with other crystals themselves. Other agents that induce nucleation include devices, such as a DTB crystallizer, an evaporative crystallizer, or cooling crystallizers (e.g., a Swenson-Walker crystallizer).

As used herein, the term "crystallization promoter" means an action or material that can promote the solidification of a compound from solution. In some embodiments, "crystallization promoter" refers to a seed crystal. In some embodiments, the crystallization promoter could obtained by scratching against a glass surface to provide surface area for crystallization. In some embodiments, sonication can promote the crystallization of a compound in solution. In some embodiments, evaporative or solvent transfer crystallization can be used. Solvent layering can promote the crystallization at the interface which in turn promotes crystallization of a compound of interest. Vapor diffusion (such as, e.g., hanging drop and sitting drop methods), and batch methods of crystallization, for example, can be used. A seed crystal can be a small piece of single crystal or polycrystal material from which a large crystal of typically the same material is to be grown. Used to replicate material, the use of a seed crystal to promote crystal growth avoids the otherwise slow randomness of natural crystal growth and allows manufacture on a scale suitable for industry. Other agents that promote crystallization include devices, such as a DTB crystallizer, an evaporative crystallizer, or cooling crystallizers (e.g., a Swenson-Walker crystallizer).

As used herein, the term "hydrogen source" refers to catalysts that can directly perform hydrogenation reactions with the needed input of $H_2$ gas. Specifically, transfer hydrogenation is the addition of hydrogen ($H_2$; dihydrogen in inorganic and organometallic chemistry) to a molecule from a source other than gaseous $H_2$. It is applied in industry and in organic synthesis, in part because of the inconvenience and expense of using gaseous $H_2$. Hydrogen-transfer catalysts have been developed based on ruthenium and rhodium complexes, often with diamine and phosphine ligands. A representative catalyst precursor is derived from (cymene)ruthenium dichloride dimer and the tosylated diphenylethylenediamine. These catalysts are mainly employed for the reduction of ketones and imines to alcohols and amines, respectively. The hydrogen-donor (transfer agent) can be isopropanol, which converts to acetone upon donation of hydrogen. Transfer hydrogenations can proceed with high enantioselectivities when the starting material is prochiral.

As used herein, the term "antioxidant" refers to compounds that can neutralize free radicals by accepting or donating electron(s) to eliminate unpaired radicals that may form during a chemical reaction. The antioxidant molecules may directly react with the reactive radicals and destroy them, while they may become new free radicals which are less active, longer-lived and less dangerous than those radicals they have neutralized. They may be neutralized by other antioxidants or other mechanisms to terminate their radical status. For example, many antioxidants have aromatic ring structures and are able to delocalize the unpaired electron. Many antioxidants may directly react with any free reactive oxygen species (ROS) and/or free radical intermediates induced by ROS and terminate the chain reaction, thereby stopping the ROS-induced damage that may occur in a chemical reaction.

As used herein, the term "radical scavenger" refers to compounds that react with free radicals. Free radicals can cause autoxidation in a reaction mixture. Radical scavengers overlap with antioxidants and include the naturally occurring tocopherols (vitamin E derivatives) but also synthetic compounds such as butylated hydroxyanisole (BHA), butylated hydroxytoluene (BHT), and tertiary butylhydroquinone (TBHQ), among others. Radical scavengers also include one or more of 1,2,2,6,6-pentamethylpiperidinyl methacrylate, 2,2,6,6-tetramethylpiperidinyl methacrylate, bis(2,2,6,6-tetramethyl-4-piperidine)sebacate, a polymer of dimethyl succinate and 4-hydroxy-2,2,6,6,-tetramethyl-1-piperidineethanol, N,N',N'',N'''-tetrakis-(4,6-bis-(butyl-(N-methyl-2,2,6,6-tetramethylpiperidine-4-yl) amino)-triazine-2-yl)-4,7-diazadecane-1,10-diamine, decanedioic acid bis(2,2,6,6-tetramethyl-1-(octyloxy)-4-piperidinyl)ester, bis(1,2,2,6,6-pentamethyl-4-piperidinyl) [[3,5-bis(1,1-dimethylethyl)-4-hydroxyphenyl]methyl]butylmalonate, a reaction product between a reaction product of cyclohexane and a peroxide N-butyl-2,2,6,6-tetramethyl-4-piperidineamine-2,4,6-trichloro-1,3,5-triazine and 2-aminoethanol (for example, TINUVIN 152 manufactured by BASF Japan Ltd.), bis(1,2,2,6,6-pentamethyl-4-piperidinyl)sebacate, methyl-1,2,2,6,6-pentamethyl-4-piperidylsebacate, tetrakis (1,2,2,6,6-pentamethyl-4-piperidine)-1,2,3,4-butanetetracarboxylate, 2-t-butyl-4-methoxyphenol, 3-t-butyl-4-methoxyphenol, 2,6-di-t-butyl-4-ethylphenol, 2,2'-methylene-bis(4-methyl-6-t-butylphenol), 4,4'-thiobis-(3-methyl-6-t-butylphenol), 4,4'-butylidene bis(3-methyl-6-t-butylphenol), 1,1,3-tris(2-methyl-4-hydroxy-5-t-butylphenyl)butane, 1,3,5-trimethyl-2,4,6-tris(3,5-di-t-butyl-4-hydroxybenzyl)benzene, tetrakis [methylene-3-(3',5'-di-t-butyl-4'-hydroxyphenyl)propionate]methane, triphenyl phosphite, diphenyl isodecyl phosphite, phenyl diisodecyl phosphite, 4,4'-butylidene-bis(3-methyl-6-t-butylphenyl ditridecyl)phosphite, cyclicneopentane tetrayl bis(nonylphenyl)phosphite, cyclicneopentane tetrayl bis(dinonylphenyl)phosphite, cyclicneopentane tetrayl tris(nonylphenyl)phosphite, cyclicneopentane tetrayl tris(dinonylphenyl)phosphite, 10-(2,5-dihydroxyphenyl)-10H-9-oxa-10-phosphaphcnanthrene-10-oxide, diisodecyl pentaerythritol diphosphite, and tris(2,4-di-t-butylphenyl) phosphite, dilauryl 3,3'-thiodipropionate, distearyl 3,3'-thiodipropionate, N-cyclohexylthio phthalimide, N-n-butylbenzene sulfonamide.

As used herein, the term "remainder," when used to refer to a solution or mixture, refers to whatever is left of the solution or mixture after any prior steps involving the solution or mixture have been carried out. As a non-limiting example, a process may involve the addition of a solution by portions, with a first amount of the solution being administered first, and the remainder of the solution being administered later. The remainder of a solution or mixture may comprise from between 0% to 100% of the original volume or the solution or mixture. If a step in a process refers to the remainder of a solution or mixture, and previous steps have consumed the entirety of the solution or mixture, the "remainder" is 0%, and none of the solution or mixture is used in that step.

As used herein, the term "oxygen scavenger" refers to a material which can combine with oxygen to reduce or completely remove oxygen content in a reaction mixture or fluid. By limiting the amount of oxygen present, the oxygen scavenger can reduce the number of deteriorative reactions that can lead to reduced yield, reduced conversion %, and/or reduced purity of a particular reaction.

As used herein, the term "metal chelator" refers to compounds that are capable of binding to metal ions. Usually, the metal chelation involves the formation or presence of two or more separate coordinate bonds between a polydentate (multiple bonded) ligand and a single central atom. Metal chelators include cyclic or acyclic polyaminocarboxylic acids such as DOTA (1,4,7,10-tetraazacyclododecane-1,4,7,10-tetraacetic acid), DTPA (diethylenetriaminepentaacetic acid), DTPA-bismethylamide, DTPA-bismorpholineamide, DO3A N-[[4,7,10-Tris(carboxymethyl)-1,4,7,10-tetraazacyclododec-1-yl]acetyl], HP-DO3A, DO3A-monoamide and derivatives thereof. Other chelators known in the art include, but are not limited to, HYNIC, DTPA, EDTA, TETA, and bisamino bisthiol (BAT) chelators (see also U.S. Pat. No. 5,720,934). For example, macrocyclic chelators, and in particular $N_4$ chelators are described in U.S. Pat. Nos. 4,885,363; 5,846,519; 5,474,756; 6,143,274; 6,093,382; 5,608,110; 5,665,329; 5,656,254; and 5,688,487, the disclosures of which are incorporated by reference herein in their entirety. Certain $N_3S$ chelators are described in PCT/CA94/00395, PCT/CA94/00479, PCT/CA95/00249 and in U.S. Pat. Nos. 5,662,885; 5,976,495; and 5,780,006, the disclosures of which are incorporated by reference herein in their entirety. The chelator may also include derivatives of the chelating ligand mercapto-acetyl-glycyl-glycyl-glycine (MAG3), which contains an $N_3S$, and $N_2S_2$ systems such as MAMA (monoamidemonoaminedithiols), DADS ($N_2S$ diaminedithiols).

As used herein, the term "protic solvent" refers to solvents comprising hydrogen atoms bonded to electronegative elements. Examples of these are, in addition to water, alcohols, amines (amines are to be understood as meaning aliphatic and cycloaliphatic amines), acid amides and carboxylic acids. They can be, in particular, lower alcohols, such as, in particular, methanol, ethanol, 1-propanol, 2-propanol, 1-butanol, 2-butanol, 2-methyl-1-propanol and/or 2-methyl-2-propanol. Protic solvents also include glycols, amines, acid amides and carboxylic acids, preferably glycols, such as monoethylene glycol, diethylene glycol, mono-1,2-propylene glycol, di-1,2-propylene glycol, 1,2-butylene glycol, 2,3-butylene glycol and/or glycerol, and amines, such as methylamine, ethylamine, n-propylamine, i-propylamine, n-butylamine, dimethylamine, diethylamine, di-n-propylamine, di-n-butylamine, pyrrolidine, piperidine, piperazine, N-methyl-piperazine, N-ethylpiperazine, morpholine, ethylenediamine, 1,2-propylenediamine, 1,3-propylenediamine, di-(2-cyanoethyl)amine, di-(2-amino-ethyl)amine, tri-(2-aminoethyl)amine, ethanolamine, diethanolamine, triethanolamine, propanolamine, dipropanolamine and/or tripropanolamine. The protic solvents can be employed as a mixture or individually. This specifically applies to the admixing of water in the case of alcohols.

As used herein, the term "azeotropic removal" or "azeotropic distillation" refers to techniques that harness interactions between the components of the solution to create properties unique to the solution, as most processes entail non-ideal mixtures, where Raoult's law does not hold. Such interactions can result in a constant-boiling azeotrope which behaves as if it were a pure compound (i.e., boils at a single temperature instead of a range). As an azeotrope, the solution contains the given component in the same proportion as the vapor, so that evaporation does not change the purity, and distillation does not effect separation. For example, ethyl alcohol and water form an azeotrope of 95.6% at 78.1° C. If the azeotrope is not considered sufficiently pure for use, there exist some techniques to break the azeotrope to give a pure distillate. This set of techniques is known as azeotropic distillation. Some techniques achieve this by "jumping" over the azeotropic composition (by adding another component to create a new azeotrope, or by varying the pressure). Others work by chemically or physically removing or sequestering the impurity. For example, to purify ethanol beyond 95%, a drying agent (or desiccant, such as potassium carbonate) can be added to convert the soluble water into insoluble water of crystallization. Molecular sieves are often used for this purpose. Immiscible liquids, such as water and toluene, easily form azeotropes. Commonly, these azeotropes are referred to as a low boiling azeotrope because the boiling point of the azeotrope is lower than the boiling point of either pure component. The temperature and composition of the azeotrope is easily predicted from the vapor pressure of the pure components, without use of Raoult's law. The azeotrope is easily broken in a distillation set-up by using a liquid-liquid separator (a decanter) to separate the two liquid layers that are condensed overhead. Only one of the two liquid layers is refluxed to the distillation set-up. High boiling azeotropes, such as a 20 percent by weight mixture of hydrochloric acid in water, also exist. As implied by the name, the boiling point of the azeotrope is greater than the boiling point of either pure component.

As used herein, the term "supercritical fluid chromatography" or "SFC" means a form of normal phase chromatography that uses a supercritical fluid such as carbon dioxide as the mobile phase. It is used for the analysis and purification of low to moderate molecular weight, thermally labile molecules and can also be used for the separation of chiral compounds. Principles are similar to those of high-performance liquid chromatography (HPLC); however, SFC typically utilizes carbon dioxide as the mobile phase; therefore, the entire chromatographic flow path must be pressurized. Since the supercritical phase represents a state in which liquid and gas properties converge, supercritical fluid chromatography is sometimes called convergence chromatography. SFC with $CO_2$ utilizes carbon dioxide pumps that require that the incoming $CO_2$ and pump heads be kept cold to maintain the carbon dioxide at a temperature and pressure that keeps it in a liquid state where it can be effectively metered at some specified flow rate. The $CO_2$ subsequently becomes supercritical post the injector and in the column oven when the temperature and pressure it is subjected to are raised above the critical point of the liquid and the supercritical state is achieved. SFC as a chromatographic process has been compared to processes having the combined properties of the power of a liquid to dissolve a matrix, with the chromatographic interactions and kinetics of a gas. The result is a large mass per injection while maintaining high chromatographic efficiency. Typically, gradient elution is employed in analytical SFC using a polar co-solvent such as methanol, possibly with a weak acid or base at low concentrations ~1%. The effective plate counts per analysis can be observed to exceed 500K plates per meter routinely with 5 µm material. The operator uses software to set mobile phase flow rate, co-solvent composition, system back pressure and column oven temperature which must exceed 40° C. for supercritical conditions to be achieved with $CO_2$. In addition, SFC provides an additional control parameter—pressure—by using an automated back pressure regulator. From an operational standpoint, SFC is as simple and robust as HPLC but fraction collection is more convenient because the primary mobile phase evaporates leaving only the analyte and a small volume of polar co-solvent. If the outlet $CO_2$ is captured, it can be recompressed and recycled, allowing for >90% reuse of $CO_2$. Similar to HPLC, SFC uses a variety of detection methods including UV/VIS, mass spectrometry, FID (unlike HPLC) and evaporative light scattering.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

All publications and patent documents cited herein are incorporated herein by reference as if each such publication or document were specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The processes of the present invention will be better understood by reference to the following Examples, which are intended as an illustration of and not a limitation upon the scope of the application.

Example 1. Synthesis of Intermediate I-4

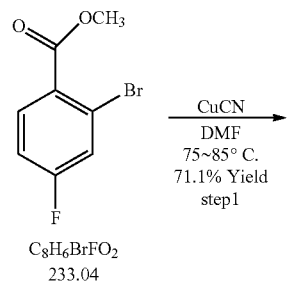

-continued

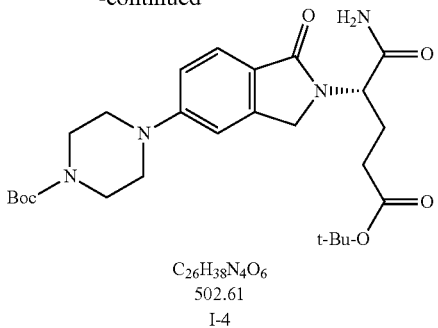

C$_{26}$H$_{38}$N$_4$O$_6$
502.61
I-4

Scheme for the Preparation in Intermediate I-4.

Step 1. Preparation of Intermediate I-1

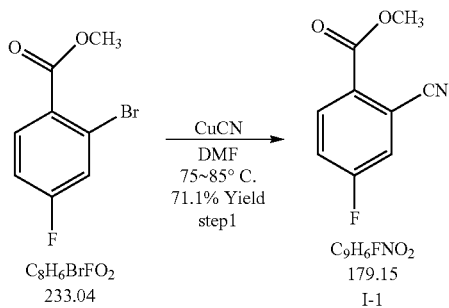

Copper(I) cyanide (55.0 kg) was charged into a 3000 L glass-lined reactor and then N, N-Dimethylformamide (456.0 kg) was added into the mixture at 15-30° C. Nitrogen was bubbled from lower port every 5-10 min, stirred for 30 min. The mixture was heated to 70-80° C.

Methyl 2-bromo-4-fluorobenzoate (120.0 kg) was added into the mixture at a rate of 70-120 kg/h at 70-80° C., and nitrogen was bubbled from lower port every 1-2 h.

The mixture was reacted at 75-85° C., and sampled for HPLC analysis every 2-6 h until the methyl 2-bromo-4-fluorobenzoate was ≤2% or the difference between two consecutive samples was ≤1%.

Sampling method: Take approximately 5 ml mixture, add 3 drops to 20 mL acetonitrile.

While the mixture was cooled to 15-25° C., nitrogen was bubbled from lower port every 1-2 h.

Purified water (1440.0 kg) was added into the mixture at a rate of 100-400 kg/h at 15-25° C., and nitrogen was bubbled from lower port every 1-2 h. After adding, the mixture was stirred for 4 h and then sampled for HPLC analysis every 1-3 h until Intermediate I-1 wt % is ≤0.5% or the difference between two consecutive samples is ≤0.5% wt.

Sampling method: Take approximately 5 ml mixture, add 3 drops to 20 mL acetonitrile.

The mixture was filtered with a stainless steel Nutsche filter in two portions. The filter cake was rinsed with purified water (240.0 kg×2) for each portion. Then the filter cake was rinsed with acetonitrile (663.8 kg) until the filter cake dissolved basically. Then the filtrate was transferred into a 5000 L glass-lined reactor.

The mixture was concentrated at T$_{internal}$=≤40° C. (T$_{jacket}$=≤50° C.) under reduced pressure (P≤−0.08 MPa) until 180 L-300 L (1.5-2.5V) left.

Ethyl acetate (2160.0 kg) was added into the mixture at 15-30° C., and then the mixture was stirred for more than 3 h.

The organic phase was washed with ammonium chloride solution (825.0 kg+825.0 kg+825.6 kg) at 15-30° C. and stirred for 1-2 h and settled until the mixture layered before separation. Note: The ammonium chloride solution was prepared with ammonium chloride (675.6 kg) and purified water (1800.0 kg).

The organic phase was washed with sodium carbonate solution (930.0 kg+930.0 kg) at 15-30° C. and stirred for 2-3 h and then settled until the mixture layered before separation. Note: The sodium carbonate solution was prepared with sodium carbonate (60.0 kg) and purified water (1800.0 kg). The organic phase was washed with sodium chloride solution (816.0 kg) at 15-30° C. and stirred for 1-2 h and then settled until the mixture layered before separation. Note: The sodium chloride solution was prepared with sodium chloride (216.0 kg) and purified water (600.0 kg).

The mixture was concentrated at T$_{internal}$=≤40° C. (T$_{jacket}$=≤50° C.) under reduced pressure (P≤−0.08 MPa) until 180 L-300 L (1.5-2.5V) was left. Heptane (160.0 kg) was added into the mixture at 15-45° C. The mixture was concentrated at T$_{internal}$=≤40° C. (T$_{jacket}$=≤50° C.) under reduced pressure (P≤−0.08 MPa) until there was 100-150 L left. Heptane (163.0 kg) was added into the mixture at 15-45° C. The mixture was sampled for HPLC analysis until ethyl acetate residual 5%.

Sampling method: Take approximately 5 ml supernatant liquid for ethyl acetate residual analysis. While the mixture was heated to 60-70° C., nitrogen was bubbled from lower port every 1-2 h. and maintain for more than 4 h.

While the mixture was cooled to 15-25° C. at the rate of 10-15° C./h, nitrogen was bubbled from lower port every 1-2 h, and maintain for 2 h.

The mixture was filtered with a stainless steel Nutsche filter in portions. The filter cake was sampled for Intermediate I-1 purity analysis until Intermediate I-1 purity ≥98%$_0$ Weight: 65.6 kg, 63.5 kg corrected. Wt %: 96.82%. Yield: 71.1%. Purity: 100%. Physical state: Off-white solid Step 2. Preparation of Intermediate I-2

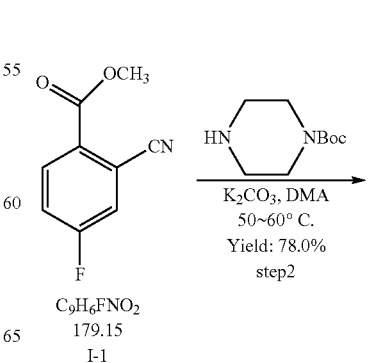

-continued

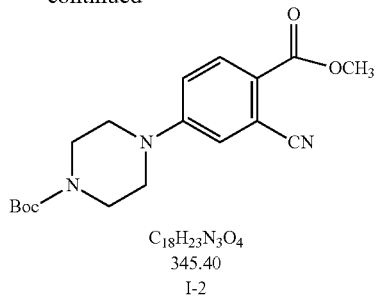

C$_{18}$H$_{23}$N$_3$O$_4$
345.40
I-2

A clean and dry 500 L glass-lined reactor 1 was confirmed oxygen content ≤1.0%.

N,N-Dimethylacetamide (177.4 kg) was charged into the glass-lined reactor 1 at 15-30° C. The mixture for KF analysis until KF≤0.05%.

Intermediate I-1 (65.0 kg) and tert-butyl 1-piperazinecarboxylate (99.0 kg) were added into the mixture through a solid addition funnel, and then stirred for 0.5 h, potassium carbonate (400 mesh) (75.0 kg) was added into the mixture through a solid addition funnel, the mixture was bubbled nitrogen from the bottom valve every 0.5-1 h.

The mixture was heated to 50-60° C. The mixture was bubbled nitrogen from the bottom valve every 0.5-1 h.

The mixture was allowed to react at 50-60° C. After 6 h, the mixture was sampled every 2-6 h for HPLC analysis until area % of raw material was ≤1 area % or the difference between two consecutive samples was ≤0.5%.

Sampling method: Take approximately 5 ml mixture and submit for analysis testing.

The mixture was cooled to 20-40° C.

The mixture in glass-lined reactor 1 was filtered with a 1000 L stainless steel Nutsche filter. The filtrate was added into receiving tank 1 for temporary storage. N,N-Dimethylacetamide (60.0 kg) was added into glass-lined reactor 1, the filter cake was added into the mixture through a solid addition funnel, and then stirred for 0.5-1 h, the mixture was bubbled nitrogen from the bottom valve every 20-30 min. The mixture was filtered with a stainless steel Nutsche filter. The filtrate was added into receiving tank 1 for temporary storage.

Purified water (754.0 kg) was added into the glass-lined reactor 2 at 20-30° C. The mixture from receiving tank 1 was added into the glass-lined reactor 2 at a reference rate of 40-60 Kg/h at 20-30° C.

The mixture was stirred at 20-30° C. for crystallization. After 2 h, the mixture was sampled every 2-6 h for mother liquor wt % analysis until it was ≤0.2 wt % or the difference between two consecutive samples was ≤0.5%.

The mixture in glass-lined reactor 1 was with filtered with a 1000 L stainless steel centrifuge at 20-30° C. Purified water (283.0 kg) was added into the glass-lined reactor 2. Then the cake was added into reactor 2 though a funnel under stirring. The solid addition funnel was rinsed with purified water (5.0 kg) to remove residual solids. The mixture was stirred for 2-3 h, bubbled N$_2$ every 0.5-1 h. The mixture in glass-lined reactor 2 was filtered with a stainless steel centrifuge. The solid was dried with rotary conical dryer at T≤45° C., P≤0.06 Mpa, the mixture was exchanged with nitrogen every 1-2 h, 8 h later, the solid was sampled for Karl-Fischer ("KF") analysis every 4-8 h until KF≤5%. After drying, the mixture was cooled to 20-30° C.

Weight: 99.6 kg, 94.6 kg corrected. Yield: 78.0%. Purity: 100%. Physical state: White solid.

Step 3. Preparation of Intermediate I-3

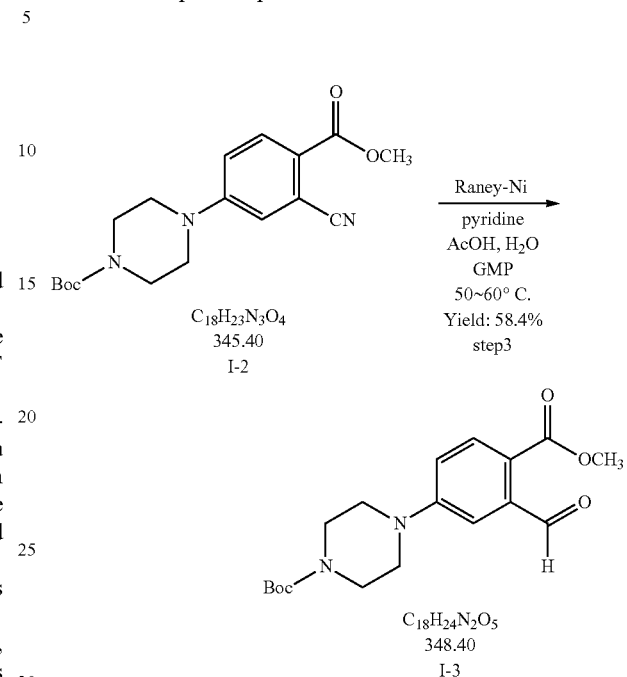

A clean and dry 3000 L glass-lined reactor 1 was confirmed oxygen content ≤1.0%. Purified water (630.8 kg) was charged into the glass-lined reactor 1 at 20-30° C.

Acetic acid (510.6 kg) was added into the mixture, and then pyridine (45.8 kg) was added into the mixture slowly at 20-30° C.

Intermediate I-2 (63.2 kg) was added into the above glass-lined reactor 1 through a solid addition funnel. Nickel TK-630 (35.4 kg) was added into the mixture through a solid addition funnel, the solid addition funnel was rinsed with purified water (16.0 kg), the mixture was bubbled nitrogen from the bottom valve every 0.5 to 1 h. The mixture was heated to 50-60° C.

The mixture was allowed to react at 50-60° C. After 1 h, the mixture was sampled every 1 to 3 h for HPLC analysis, until area % of Intermediate I-2 was ≤20%, area % of Intermediate I-3 was ≥70% or the difference between two consecutive samples was ≤2%.

Sampling method: Take approximately 0.5 ml mixture to 10 ml ACN, filter, collect filtrate and submit for analysis testing.

The mixture was cooled to 20-30° C. rapidly, at the same time, isopropyl acetate (329.4 kg) was added into the mixture during cooling, the mixture was stirred for 0.5 to 1 h.

The mixture was filtered with a 1000 L stainless steel Nutsche filter. Isopropyl acetate (218.0 kg) was added into glass-lined reactor 1, then the rinsing liquor was transferred into stainless steel Nutsche filter to rinse the filter cake. The filtrate was transferred into 3000 L glass-lined reactor 2 for temporary storage.

The mixture was stirred for 0.5 h at 20-30° C. and then settled until the mixture layered before separation. The lower aqueous phase was transferred into glass-lined reactor 1 for temporary storage. The upper organic phase was left in glass-lined reactor 2 for temporary storage. The lower aqueous phase was transferred into glass-lined reactor 1 for temporary storage.

The aqueous phase in the glass-lined reactor 1 was extracted with IPAC (437.4 kg) at 20-30° C., the mixture was stirred for NLT 0.5 h and settled until the mixture was layered before separation. The upper organic phase was left in glass-lined reactor 2 for temporary storage.

Sodium carbonate solution (900.0 kg) was added into the glass-lined reactor 2 at a reference rate of 100-150 Kg/h, the mixture was stirred for NLT 0.5 h and settled until the mixture layered before separation. The upper organic phase was left in glass-lined reactor 2 for temporary storage. Note: Sodium carbonate solution was prepared with sodium carbonate (300.0 kg) and purified water (1500.0 kg).

Sodium carbonate solution (579.8 kg) was added into the glass-lined reactor 2 at 10-20° C., the mixture pH was adjusted to 8-9 (text aqueous phase) at a reference rate of 100 to 150 Kg/h, the mixture was stirred for NLT 0.5 h and settled until the mixture layered before separation. The upper organic phase was left in glass-lined reactor 2 for temporary storage.

Citric acid monohydrate solution (900.6 kg) was added into the glass-lined reactor 2 at 10-20° C., the mixture was stirred for NLT 0.5 h and settled until the mixture was layered before separation. The upper organic phase was left in glass-lined reactor 2 for temporary storage. Note: Citric acid monohydrate solution was prepared with citric acid monohydrate (275.0 kg) and purified water (1536.0 kg).

Citric acid monohydrate solution (724.6 kg) was added into the glass-lined reactor 2, the mixture pH was adjusted 1-2 (test aqueous phase), and then stirred for NLT 0.5 h and settled until the mixture was layered before separation. The upper organic phase was left in glass-lined reactor 2 for temporary storage.

Sodium bicarbonate solution (320.0 kg) was added into the glass-lined reactor through liquid material filter at 10-20° C., the mixture was stirred for NLT 0.5 h and settled until the mixture was layered before separation. The aqueous phase for pH analysis until pH ≥7. The upper organic phase was left in glass-lined reactor 2 for temporary storage. Note: Sodium bicarbonate solution was prepared with sodium bicarbonate (21.0 kg) and purified water (300.0 kg).

Sodium chloride solution (750.2 kg) was added into the glass-lined reactor 2, and then stirred for NLT 0.5 h and settled until the mixture was layered before separation at 20-30° C. The upper organic phase was left in glass-lined reactor 2 for temporary storage. The aqueous phase was sampled for pH analysis until pH≥7. Note: Sodium chloride solution was prepared with sodium chloride (150.2 kg) and purified water (605.0 kg).

The mixture was concentrated at T≤40° C. under reduced pressure (P≤−0.08 MPa) until 1 to 1.5 vol left. The mixture was less at the later stage of concentration, transfer into 200 L glass-lined reactor 3 to continue to concentrate. The mixture was adjusted to T≤30° C. DCM (78.0 kg) was added into the mixture at T≤30° C., the mixture was stirred until homogenous.

Silica gel (270.0 kg) (200 to 300 mesh) was added to chromatographic columns, and then sodium chloride (40.0 kg) (5 to 15 cm) was added on the silica gel, and then one layer of filter cloth and a glass pane were loaded on the sodium chloride, vacuum for 4 to 6 h.

Addition of the NaCl press the column with n-heptane (814.8 kg) repeatedly, load one layer of filter cloth on the top of sodium chloride, keep 40-80 Kg n-heptane on the upper layer of the column, and then the after concentration mixture was added into the column.

The silica gel column was eluted with the washing liquor, monitor the eluent by TLC every time when 100-400 L eluent is received, until there was no Intermediate I-3 residual. Note: The washing liquor was prepared with isopropyl acetate (1349.4 kg+361.6 kg) and n-heptane (3727.0 kg+2701.0 kg).

The mixture of was transferred into 2000 L glass-lined reactor 4.

The mixture was concentrated at T≤40° C. under reduced pressure (P≤−0.08 MPa) until 120 L to 180 L (4V to 5V) left. n-heptane (208.0 kg+208.4 kg) was added into the mixture at a reference rate of 40-60 Kg/h at T≤40° C. The mixture was sampled for Isopropyl acetate residual analysis isopropyl acetate residual 1%. The mixture was cooled to 0-10° C.

The mixture was stirred at 0-10° C. for crystallization. After 4 h, the mixture was sampled every 2-6 h for mother liquor wt % analysis until it was ≤0.2 wt % or the difference between two consecutive samples was ≤0.5%.

The mixture was filtered with a 500 L stainless steel Nutsche filter. The filter cake was left in stainless steel Nutsche filter.

The solid was dried at T≤40° C. under reduced pressure (P≤−0.06 MPa), 10 h later, the solid was sampled for analysis every 4-8 h until n-heptane residual ≤0.5% and isopropyl acetate residual ≤0.5%, KF≤0.5%. After drying, the mixture was cooled to 20-30° C.

Weight: 36.0 kg, 35.5 kg corrected. Yield: 58.4%. Purity: 99%. Assay: 98.61%. Physical state: Yellow solid.

The methods for preparing Intermediate I-3 was also accomplished according to the same process as above, but using 2,6-lutidine and propionic acid as described below:

| | Conditions |
|---|---|
| 1 | Nickel TK-63D, 0.77 g/g, 50~60° C., 0.73 V 2,6-lutidine; 9 V propionic acid; 10.5 V water |
| 2 | Nickel TK-63D, 0.77 g/g, 50~60° C., 0.73 V 2,6-lutidine; 9 V propionic acid; 5.5 V water |
| 3 | Nickel TK-63D, 0.77 g/g, 50~60° C., 0.73 V 2,6-lutidine; 9 V propionic acid; 15.5 V water |

Step 4A: Preparation of Intermediate I-2A

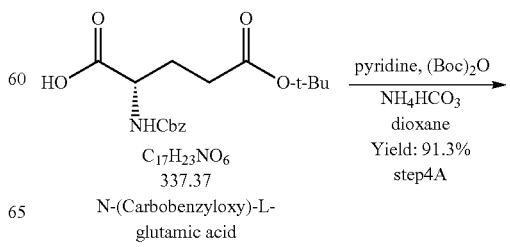

$C_{17}H_{23}NO_6$
337.37
N-(Carbobenzyloxy)-L-glutamic acid pyridine, (Boc)$_2$O
NH$_4$HCO$_3$
dioxane
Yield: 91.3%
step4A -continued

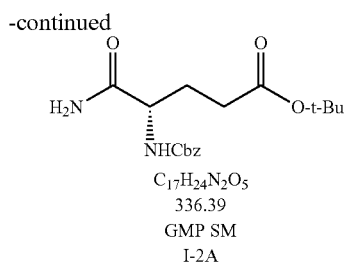

C17H24N2O5
336.39
GMP SM
I-2A

A clean and dry 3000 L glass-lined reactor 1 was confirmed oxygen content ≤1.0%. 1,4-dioxane (679.8 kg) was charged into the glass-lined reactor 1 at 15-25° C. The mixture was sampled for KF, purity analysis until KF≤0.1%. KF was 0.36%, additional 1,4-dioxane (679.8 kg) was added into the mixture and then sampled until KF≤0.1%.

N-(Carbobenzyloxy)-L-glutamic acid (110.1 kg) was added into the mixture portion-wise at the interval of 5-10 min at 15-25° C. through a solid addition funnel, after adding, bubbled nitrogen to the mixture from the bottom valve 2-3 min, and then stirred for 20-30 min until the mixture was basically clear.

Pyridine (6.6 kg) was added into the mixture at 15-25° C. by pump. Ammonium bicarbonate (34.0 kg) was added into the mixture through a solid addition funnel, the mixture bubbled nitrogen from the bottom valve every 0.5-1 h.

Di-tert-butyl dicarbonate (92.4 kg) was added into the mixture slowly at 15-25° C. at a reference rate of 15-25 Kg/h, the mixture bubbled nitrogen from the bottom valve every 0.5-1 h.

The mixture was allowed to react at 15-25° C. After 10 h, the mixture was sampled every 2-6 h for HPLC analysis, until area % of N-(Carbobenzyloxy)-L-glutamic acid was ≤1 area %.

Sampling method: Take approximately 5 ml mixture and submit for analysis testing.

Purified water (440.0 kg) and ethyl acetate (581.2 kg) were added into the mixture at 15-25° C.

The mixture was stirred for NLT 0.5 h at 15-25° C. and then settled until the mixture layered before separation. The aqueous phase was transferred into glass-lined reactor 2

The aqueous phase in the glass-lined reactor 2 was extracted with ethyl acetate (297.2 kg) at 15-25° C., and then stirred for NLT 0.5H and settled until the mixture layered before separation. The organic phase was transferred into glass-lined reactor 2 combined with organic phase for temporary storage.

The mixture was stirred for NLT 0.5 h and settled until the mixture layered before separation. The upper organic phase was left in glass-lined reactor for temporary storage.

Potassium bicarbonate solution was added into the glass-lined reactor to wash at 15-25° C., stirred for 1-1.5 h and settled until the mixture layered before separation. The upper organic phase was left in glass-lined reactor 2 for temporary storage. Note: Potassium bicarbonate solution was prepared with potassium bicarbonate (11.0 kg) and purified water (100.0 kg).

Citric acid monohydrate solution was added into the glass-lined reactor 2 at 15-25° C., and stirred for NLT 1H and settled until the mixture layered before separation. The upper organic phase was left in glass-lined reactor 2 for temporary storage. Note: Citric acid monohydrate solution was prepared with citric acid monohydrate (27.5 kg) and purified water (275.0 kg).

Sodium chloride solution was added into the glass-lined reactor 2 at 15-25° C., and then stirred for NLT 0.5H and settled until the mixture layered before separation. The aqueous phase was sampled for pH analysis until pH=6-8. pH=5, organic phase was washed with sodium chloride solution until pH of aqueous phase was 6-8. Note: Sodium chloride solution was prepared with sodium chloride (83.0 kg×3+84.0 kg) and purified water (250.0 kg×3+252.0 kg).

The mixture was concentrated at T≤30° C. under reduced pressure (P≤−0.08 MPa) until 495.5-605.6 L (4.5V-5.5V) left. n-heptane (752.4 kg+546.4 kg) was added into the mixture at a reference rate of 150-200 Kg/h, the mixture was stirred until clear. The mixture was sampled for ethyl acetate residual analysis until ethyl acetate residual 1%.

The mixture was adjusted to 40-45° C., maintained for 0.5-1 h, the mixture was cooled to 0-10° C. slowly, at a reference rate of 5-15° C./h, maintained for 2 h, the mixture was sampled every 2-6 h for mother liquor wt % analysis until it was ≤0.3 wt % or the difference between two consecutive samples was ≤0.3%.

The mixture was filtered with a (D1250 stainless steel centrifuge. After filter, if there are many solids residue in the reactor, the reactor rinsed with mother liquid firstly.

The solid was dried with a rotary conical dryer at T≤40° C., P≤0.06 MPa, 10 h later, the solid was sampled for KF and solvent residual analysis every 4-8 h until n-heptane residual ≤0.5%, ethyl acetate residual ≤0.5%, KF≤0.5%. After drying, the solid was cooled to 20-30° C.

Weight: 100.1 kg. Yield: 91.3%. Purity: 100.0%. Physical state: White solid.

Step 4B: Preparation of Intermediate I-3A

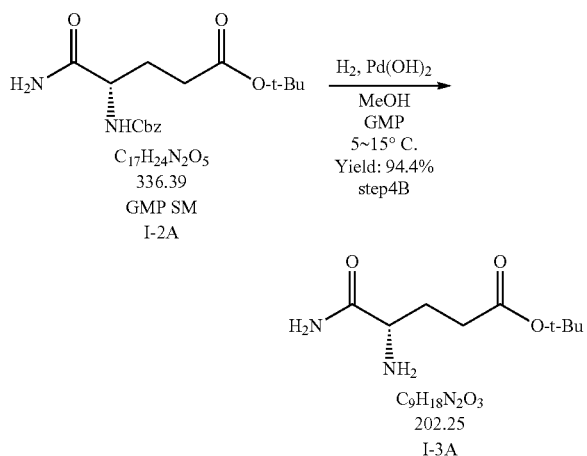

A clean and dry 300 L autoclave reactor 1 was confirmed oxygen content ≤1.0%.

Methanol (118.6 kg) was added into the autoclave reactor 1. The mixture was sampled for KF analysis until KF≤0.1%.

Intermediate I-2A (50.2 kg) was added into the autoclave reactor 1 through a solid addition funnel at 10-30° C., and then stirred for at least 0.5 h.

The autoclave reactor 1 was purged with nitrogen via subsurface pipe to 0.10-0.20 MPa, then vent to 0.02-0.05 MPa. This was repeated 3 times. Oxygen content was detected until it was ≤1.0% after exchanging. 10% Pd(OH)2 (2.56 kg) was added into the autoclave reactor 1 at 10-30° C.

The autoclave reactor 1 was purged with nitrogen via subsurface pipe to 0.10-0.20 MPa, then vent to 0.02-0.05 MPa. This was repeated 3 times. Oxygen content was detected until it was ≤1.0% after exchanging.

The mixture was adjusted to 5-15° C.

The autoclave reactor 1 was purged with hydrogen via subsurface pipe to 0.15-0.30 MPa, then vent to 0.03-0.04 MPa. This was repeated 5 times. At the last time exchange, the pressure was increased to 0.9-1.1 Mpa with hydrogen.

The mixture was allowed to react at 5-15° C. The pressure was maintained with hydrogen at 0.9-1.1 MPa (target: 1.0 MPa). (Every 6-10 h, vent the mixture to 0.03-0.04 MPa, purge the mixture with hydrogen via subsurface pipe to 0.9 to 1.1 MPa, then vent to 0.03-0.04 MPa). After 6 h, the mixture was sampled every 2-6 h for Intermediate I-2A assay analysis, until assay of Intermediate I-2A was ≤1.0%.

Sampling method: Take 5 ml mixture filter the mixture and submit the filtrate for analysis testing. The autoclave reactor 1 was vent with nitrogen via subsurface pipe to 0.02-0.05 MPa, then purged to 0.2-0.3 MPa. This was repeated 8 times. The mixture was monitored until oxygen content ≤1.0% and hydrogen content ≤1.0% after exchanging.

The mixture was filtered with a DN500 stainless steel Nutsche filter. Methanol (3.96 kg) was added into autoclave reactor 1, and then pre-cooled to T≤15° C., then soak the filter cake.

The intermediate was transferred into a 1000 L glass-lined reactor 2, the mixture was cooled to −10-10° C. for temporary storage.

Weight: 160.0 kg, 28.5 kg corrected. Yield: 94.4%. Assay: 17.81%. Purity: 99.2%. Physical state: Colorless liquid.

Step 4: Preparation of Intermediate I-4

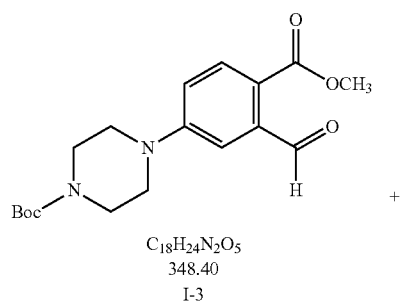

$C_{18}H_{24}N_2O_5$
348.40
I-3

+

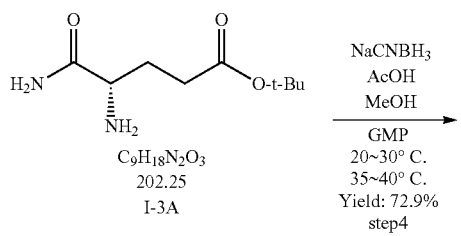

$C_9H_{18}N_2O_3$
202.25
I-3A

NaCNBH$_3$
AcOH
MeOH
GMP
20~30° C.
35~40° C.
Yield: 72.9%
step4

-continued

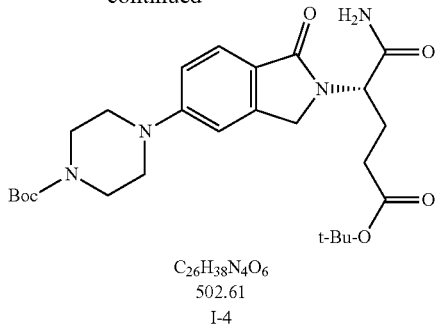

$C_{26}H_{38}N_4O_6$
502.61
I-4

Intermediate I-3A solution in methanol (79.2 kg, 76.8 kg corrected) was charged a 1000 L glass-lined reactor 1, The mixture was adjusted to 0-10° C.

Intermediate I-3 (79.2 kg) was added into the mixture through solid addition funnel at 0-10° C. Acetic acid (15.2 kg) was added into the mixture through pump at 0-10° C.

The mixture was heated to 20-30° C. The mixture was allowed to react at 20-30° C. The mixture was stirred for 8 h.

Methanol (63.0 kg) was added to a 200 L glass reactor 2. The mixture was sampled for KF analysis until KF≤0.1%.

Sodium cyanoborohydride (10.4 kg) was added into the glass-lined reactor 2 through a solid addition funnel. The mixture was stirred until clear and store for later use.

The mixture was cooled to 5-10° C. Sodium cyanoborohydride solution in methanol was added into the glass-lined reactor 1 at a reference rate of 5-25 Kg/h, and then stirred for NLT 1 h.

The mixture in glass-lined reactor 1 was heated to 20-30° C. The mixture was allowed to react at 20-30° C. After 3 h, the mixture was sampled every 1-3 h for HPLC analysis until area % of Intermediate I-3 was ≤2%.

Sampling method: Take approximately 5 ml mixture, dilute with 20 ml acetonitrile to filter and submit filtrate for analysis testing.

The mixture was heated to 35-40° C. The mixture was allowed to react at 35-40° C. After 10 h, the mixture was sampled every 2-6 h for HPLC analysis until area % of the second stage intermediate1 was ≤3% or the difference between two consecutive samples was ≤0.5%.

Sampling method: Take approximately 5 ml mixture, dilute with 20 ml acetonitrile to filter and submit filtrate for analysis testing.

Purified water (160.0 kg) was added into the glass-lined reactor 1, the mixture was stirred for 30 min, the mixture was bubbled nitrogen from the bottom valve to degas for 2-4 h, the hydrogen content was detected until ≤1000 ppm.

The mixture was concentrated at $T_{internal}$≤40° C. ($T_{jacket}$≤50° C.) under reduced pressure (P≤−0.08 MPa) until 2-3V left. Ethyl acetate (286.2 kg+285.2 kg+427.4 kg) into the mixture at T≤40° C. The mixture was transferred into a 5000 L glass-lined reactor 2 at T≤40° C. Ethyl acetate (751.6 kg) was added into the glass-lined reactor 1 at T≤40° C., the mixture was stirred for 10 min, the mixture was transferred into the glass-lined reactor 2.

The mixture was stirred for NLT 1 h at 15 to 30° C.

The mixture was filtered with a 1000 L plastic-lined Nutsche filter connect plastic-lined liquid material filter at the back. Ethyl acetate (142.6 kg) was added into glass-lined reactor 2, then the rinsing liquor was transferred into plastic-lined Nutsche filter, rinse the filter cake.

The mixture of filtered was transferred into 5000 L glass-lined reactor 3 at 20-30° C. The mixture was settled until layered before separation. The upper organic phase was left in glass-lined reactor 3 for temporary storage.

Sodium chloride solution (618.0 kg×2) was added into the glass-lined reactor 3 at 15-30° C., and then stirred for NLT 0.5 h and settled until the mixture layered before separation. The upper organic phase was left in glass-lined reactor 3 for temporary storage. Purified water (396.0 kg) was added into the reactor 3, and then stirred for NLT 0.5 h and settled until the mixture layered before separation.

The upper organic phase was left in reactor 3. Note: Sodium chloride solution was prepared with sodium chloride (474.2 kg) and purified water (1582.0 kg).

Sulfhydryl silica gel (16.0 kg) was added into the mixture. The mixture was stirred for 2 h at least. Celite (10.0 kg) was added into a 1000 L plastic-lined Nutsche filter (2 cm). Ethyl acetate (144.0 kg) was added into glass-lined reactor 3, then the rinsing liquor was transferred into plastic-lined Nutsche filter, rinse the filter cake. The filtrate was transferred into a 3000 L glass-lined reactor 4. The mixture at $T_{internal} \leq 40°$ C. ($T_{jacket} \leq 50°$ C.) under reduced pressure ($P \leq -0.08$ MPa) until (4V to 6V) left. The mixture was adjusted to 40-50° C., toluene (688.8 kg+689.2 kg+689.8 kg) was added into the mixture through liquid material filter at a reference rate of 50 to 100 Kg/h. The mixture was sampled for ethyl acetate residual analysis.

The mixture was adjusted to 20-30° C. n-heptane (542.0 kg) was added into the mixture at 20-30° C. through liquid material filter.

The mixture was adjusted to 20-30° C. The mixture was stirred at 20-30° C. for crystallization. After 6 h, the mixture was sampled every 1-3 h for Intermediate I-4 mother liquor wt % analysis until it was ≤1 wt % or the difference between two consecutive samples was ≤0.5%.

The mixture was filtered with a 1000 L stainless steel Nutsche filter. Toluene (52.0 kg+135.0 kg) and n-heptane (122.0 kg+135.0 kg) were added into 3000 L glass-lined reactor 4 through liquid material filter (1V:3V), then transfer the rinsing liquor into stainless steel Nutsche filter through liquid material filter, rinse the filter cake.

n-heptane (134.6 kg) were added into 3000 L glass-lined reactor 4 through liquid material filter, then transfer the rinsing liquor into stainless steel Nutsche filter through liquid material filter, rinse the filter cake for two times.

Ethyl acetate (640.6 kg) was added into glass-lined reactor 4 through liquid material filter. Then filter cake was added into mixture, the mixture was bubbled nitrogen from the bottom valve every 0.5 to 2 h, and stir for 4 h to 8 h at 30 to 40° C.

The mixture at $T_{internal} \leq 40°$ C. ($T_{jacket} \leq 50°$ C.) under reduced pressure ($P \leq -0.08$ MPa) until 158.4-316.8 L (2V to 4V) left. Ethyl acetate (640.8 kg) was added into the mixture at 30-40° C. The mixture at $T_{internal} \leq 40°$ C. ($T_{jacket} \leq 50°$ C.) under reduced pressure ($P \leq -0.08$ MPa) until 237.6-396 L (3V to 5V) left.

At 20-30° C. n-heptane (484.8 kg) was added into the mixture through liquid material filter at a reference rate of 50 to 100 Kg/h.

The mixture was stirred at 20-30° C. for crystallization. After 4 h, the mixture was sampled every 1-3 h for Intermediate I-4 mother liquor wt % analysis until it was ≤1 wt % or the difference between two consecutive samples was ≤0.5%.

The mixture was filtered with a 1000 L stainless steel Nutsche filter. The filter cake was rinsed with n-heptane (79.2 kg). The filter cake was sampled for purity and toluene residual.

The solid was dried at $T_{jacket} \leq 40°$ C., 10 h later, the solid was sampled for analysis every 4-8 h until methanol residual ≤0.4%, ethyl acetate residual ≤0.4%, toluene residual ≤0.4% and n-heptane residual ≤0.4%. After drying, the mixture was cooled to 20-30° C.

Weight: 83.3 kg. Yield: 72.9%. Purity: 99.8%. Physical state: Off-white solid.

Example 2. Synthesis of Intermediate I-6

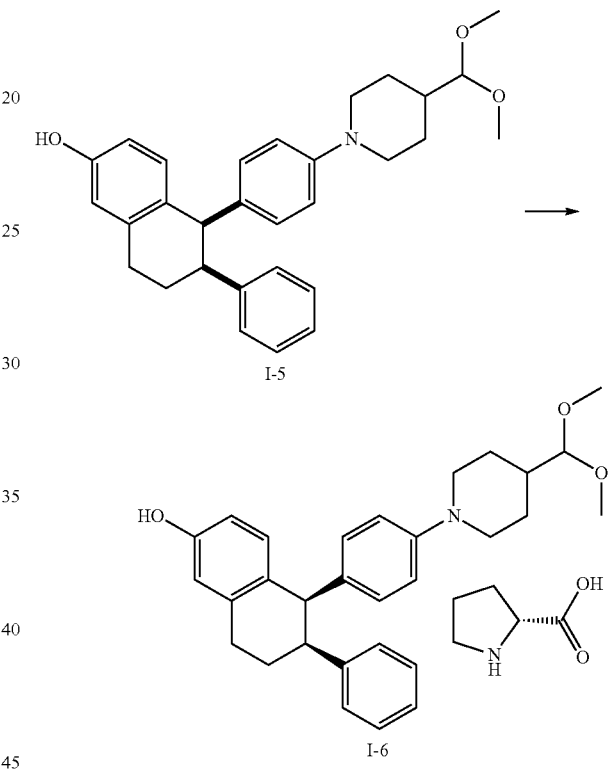

The vessel was charged with 2-propanol (74 L) at 25° C. and Intermediate I-5 (4.903 kg) and 2,6-di-tert-butyl-4-methylphenol (BHT) (23.9 g) were added while stirring and 2-Methyl-THF (37 L) was added.

The suspension was heated to reflux (IT=80° C.) within 74 min setting a jacket temperature of 105° C.

After 6 min at reflux a clear solution was obtained and the internal temperature was lowered to 77° C. within 32 min (min. jacket temperature 65° C.). Note: It is important that no solids are present anymore, as they can function as seed crystals for the racemate.

A solution of D-Proline (706 g) in water (1.4 L) was prepared and 10% of this proline solution was added into the Intermediate I-5-solution over 1 min.

Subsequently the seeding crystals (Intermediate I-6, 9.21 g) were added to the solution. The seeds dissolved within about 1 to 2 minutes. A second portion of 10% of the proline solution was added into the Intermediate I-5-solution over 2 min. Subsequently a second portion of seeding crystals (Intermediate I-6, 9.30 g) was added to the brown solution giving instantly a slightly turbid suspension.

After 7 minutes the remaining amount of D-proline solution was added over 7 min.

The flask of the proline solution was flushed with 2-propanol (0.8 L), which was added into the vessel. The brown suspension was aged for 25 min at an internal temperature 75° C. The suspension was cooled to 27° C. over 75 min. As soon as an internal temperature of 27° C. was reached, the suspension was filtered. Filtration time (without washing) was 45 min (filter diameter 30 cm). The filter cake was washed three times with 2-PrOH (each time 5.0 L) and pre-dried for around 32 min on the filter.

The crude was successively dried under vacuum (≤10 mbar) at 45° C. 2.564 kg (42%) of an off-white solid was obtained.

Example 3. Synthesis of Intermediate I-8

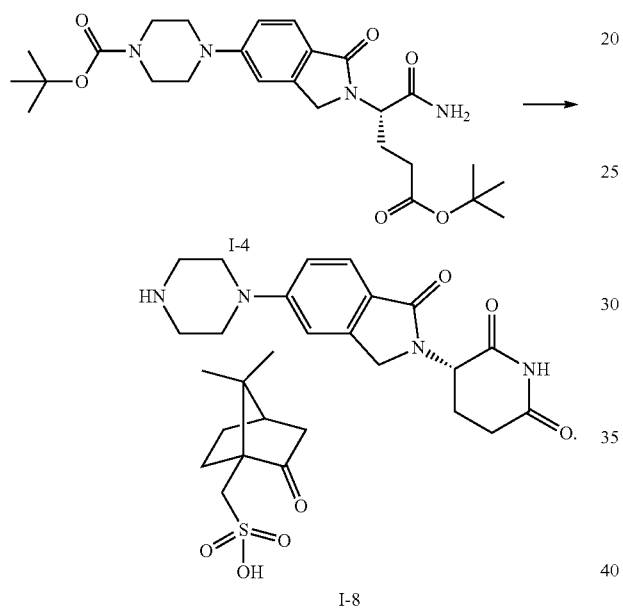

The vessel was charged with acetonitrile (50.0 L) at 25° C. and Intermediate I-4 (7.053 kg) was added while stirring. DMF (14.0 L) was added, followed by CSA (7.350 kg). Acetonitrile (7.0 L) was added once more.

The clear solution was heated to reflux over 68 min setting a jacket temperature of 100° C. Slight foaming was observed during heating.

Over 4 h 53 min 37.5 L of solvent were distilled off (IT: 85 to 86° C.). During this time, acetonitrile (5×7.5 L) was added in 5 portions to keep the reaction concentration approximately constant. IPC 1 indicated 69% conversion.

The jacket temperature was lowered to 78° C. over 40 min to ensure a safe stirring overnight (12 h). IPC 2 indicated a conversion of 96.9%. Conversion criterion was already fulfilled (≥93%).

Over 75 min the internal temperature was lowered from 77° C. to 26° C. The white suspension was stirred for another hour at 26° to 25° C.

The product was filtered off within 43 min using a 30 cm filter. No lumps or crust on the walls of the vessel were observed. The product was dried in two portions on the rotary evaporator at 50° C. and <10 mbar. 7.259 kg of a white product (92% yield) was obtained with a HPLC-purity of 98.6% a/a and a chiral purity of 98.4% a/a.

Example 4. Synthesis of Compound 1—First Synthesis

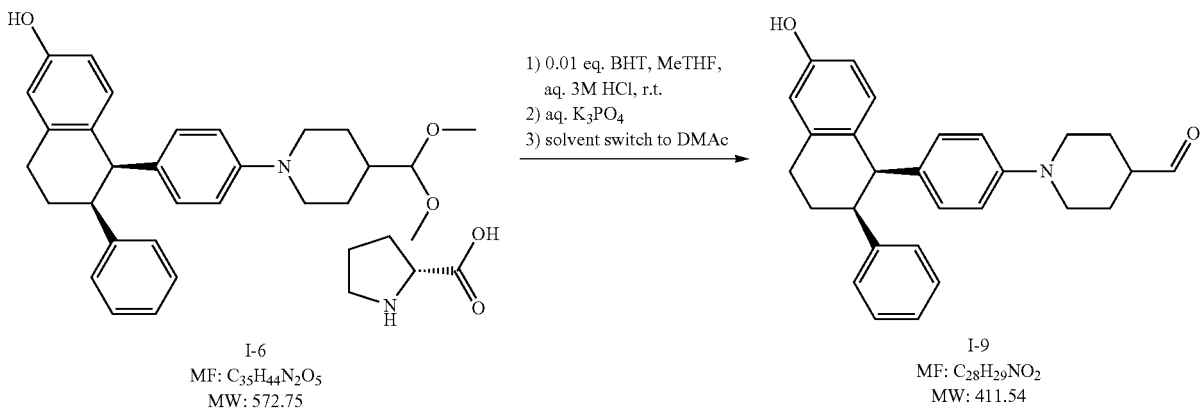

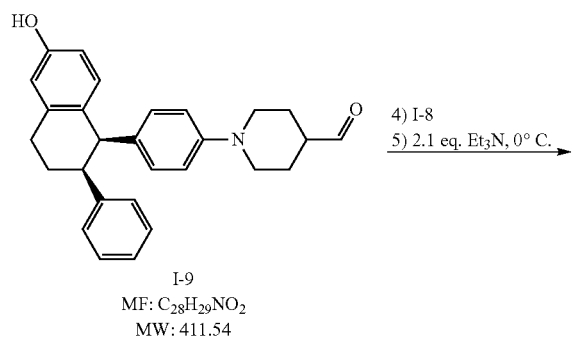

I-9
MF: C₂₈H₂₉NO₂
MW: 411.54

4) I-8
5) 2.1 eq. Et₃N, 0° C.

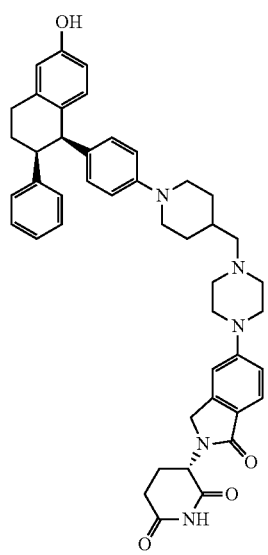

Compound 1
MF: C₄₅H₄₉N₅O₄
MW: 723.92

6) 1.8 eq. Na[BH(OAc)₃], 0° C.
7) prequench with 10 eq H₂O
8) inverse quench with H₂O and EtOH, 70° C.
9) dissolution in 9:1 DCM/MeOH
10) 0.01 eq. BHT
11) inline filtration
12) recrystallization n-BuOH The vessel was charged with water (18.5 L) at 25° C. 32% HCl (5.55 L) was added portion-wise while stirring. Addition tank was rinsed with water (0.6 L).

2-Methyltetrahydrofuran (12 L) was added into the vessel.

Intermediate I-6 (6.104 kg) was added at 25° C., followed by BHT (14 g) into the vessel. 2-Methyltetrahydrofuran (0.60 L) was added.

The reaction mixture was stirred for 2.5 h at 25° C.

IPC 1 indicated a conversion of 98.7%.

A solution of K₃PO₄ (14.712 kg) in water (16.0 L) was prepared, resulting in a total volume of 19 L.

9.0 L of the K₃PO₄-solution was added to the reaction mixture to reach pH 7.

The brown emulsion was stirred for 5 min, afterwards the layers were separated (fast phase separation).

The aqueous layer was extracted once more with 2-Methyl-tetrahydrofuran (12.0 L).

The combined organic layers were concentrated at 45° C. to an oil over 230 min. DMAc (6.0 L) was added and the brown solution was stirred at 45° C. on the rotary evaporator at maximum vacuum capacity (start: 40 mbar, end: 17 mbar) for 80 min. IPC 2 by NMR indicated a residual content of 0.14 eq 2-methyltetrahydrofuran relative to Intermediate I-9.

The aldehyde solution in DMAc was transferred into the vessel. DMAc (25.5 L) was added and the brown solution was cooled to an internal temperature of 0° C. while stirring and stored like that overnight.

The next morning, Intermediate I-8 (5.796 kg) was added in one portion (not exothermic), followed by N-methylmorpholine (2.265 kg) addition over 3 min (slightly exothermic).

The addition tank was rinsed with DMAc (3.0 L) and the reaction mixture was stirred for 37 min at an internal temperature of +1 to +2° C.

NaBH(OAc)₃ (1.357 kg, 1.348 kg and 1.351 kg) was added in three portions at an internal temperature of −1 C to +1° C., waiting 21 min and 20 min between additions.

23 min after the last addition, IPC 3 was sampled and HPLC indicated a ratio of 97:3 Compound 1 to Intermediate I-9.

Over 14 min, water (4.0 L) was added at −1 to 8° C. to the reaction mixture as a pre-quench (exothermic reaction).

The reaction mixture was warmed to 10° C. over 22 min and transferred into a mixing vessel. The reaction mixture was stirred at room temperature for 101 min to gas out.

In the meantime, the vessel was charged with water (40 L) and ethanol (40 L). The solvent mixture was heated to an inner temperature of 73° C.

Temperature control was switched to external temperature control and a jacket temperature of 80° C. was set.

To precipitate the crude, 4.5 L of the DMAc-solution out of the mixing vessel was added to the water/EtOH-mixture over 21 min at 73 to 75° C. Seeds (5.3 g) were added and a fine white suspension was formed within 10 minutes.

Over 32 min, the remaining DMAc-solution was added at 76 to 71° C.

The resulting suspension was stirred for further 11 min at elevated temperature and then cooled to 25° C. over 84 min. The suspension was stirred at an internal temperature of 25° C. overnight.

The crude product was filtered (32 min) and washed with water (2×6.0 L) and ethanol (2×6.0 L).

After drying at 70° C. over 23 h in two portions in a 20 L rotary evaporator, 5.858 kg (78.3%) white crude product was obtained with a HPLC-purity of 98.6% area (achiral) and chiral purity of 97.6/97.5% area.

The stirring tank was charged with DCM (33.0 L).

The crude product (5.850 kg) was added, followed by BHT (17.7 g).

Methanol (3.5 L) was added and the mixture was stirred until all solid dissolved.

Hyflo (0.57 kg) was added and the suspension was stirred for 24 min.

The dark brown suspension was filtered via a deep filter plate (fast filtration) followed by a 3 m inline filter. The stirring tank and filter were rinsed with a mixture of dichloromethane (5.5 L) and methanol (0.6 L).

The filtered, crude product solution (45 L) was transferred into the vessel. The jacket temperature was increased to 55° C. and 19 L of solvent was distilled off at normal pressure within 50 min.

The vessel was switched to reflux. Over 10 min inline filtered n-butanol (6.0 L) was added, the internal temperature rose from 38° C. to 40° C.

Seed crystals (5.7 g) were added to the brown solution. 5 min after addition, the brown solution was still clear.

The vessel was switched to distillation. Over 16 min 5.8 L solvent mixture was distilled off at a jacket temperature of 55 to 80° C. The internal temperature rose to 42° C.

The vessel was switched to reflux. Over 8 min inline filtered n-butanol (6.0 L) was added, the internal temperature rose from 43° C. to 45° C.

Seed crystals (5.7 g) were added again to the brown solution. 5 min after addition, small particles were observed, forming a thin brown suspension.

The vessel was switched to distillation. Over 10 min 6.0 L solvent mixture were distilled off.

The internal temperature rose to 50° C.

The vessel was switched to reflux. Over inline filtered n-butanol (6.0 L) was added, the internal temperature rose to 51° C.

The vessel was switched again to distillation. After distilling off 5.0 L an internal temperature of 60° C. was reached and the system was switched to reflux.

Inline filtered n-butanol (6.0 L) was added and the brown suspension was stirred for 2 h at a jacket temperature of 80° C. (IT: 61-69° C.).

Over 60 min, the jacket temperature was lowered to 25° C. and the brown suspension was stirred at 25° C. overnight.

The next morning, the crude was filtered off (filtration time: 55 min incl. rinsing the vessel with mother liquor). The filter cake was washed with inline filtered n-BuOH (2×6.0 L) and inline filtered TBME (2×6.0 L).

After drying at 70° C. for 22 h, 5.556 kg (74% yield, 95% recovery) of a white solid with an achiral purity of 99.2% and a chiral purity of 98.1% was obtained. NMR indicated a residual n-BuOH content of 0.058 equivalents.

Example 5. Synthesis of Compound 1—Second Synthesis

The reaction up to isolation of the crude Compound 1 was performed in two separate batches analogous to the previous described reaction above. The only difference was implementation of a Hyflo treatment of the 2-Methyltetrahydrofuran solution of Intermediate I-9, due to foreign particles in the starting Intermediate I-6.

Both crude products were collected on the same 50 L glass nutsch. Up to isolation of the crude product, all three reactions can be summarized as followed:

|  | reaction 1 | reaction 2 | reaction 3 |
| --- | --- | --- | --- |
| Amount Intermediate I-6 | 6.104 kg | 6.102 kg | 6.108 kg |
| IPC 1: conversion to Intermediate I-9 | 98.7% | 99.5% | 99.1% |
| IPC 2: eq. Residual Me—THF | 0.14 eq | 0.10 eq | 0.10 eq |
| Amount Intermediate I-8 | 5.794 kg | 5.787 kg | 5.783 kg |
| Amount Na[BH(OAc)₃] | 4.056 kg | 4.069 kg | 4.068 kg |
| IPC 3: conversion to Compound 1 | 96.6% | 99.9% | 99.1% |
| filtration crude Compound 1 | 32 min | 37 min | 78 min |
| amount crude Compound 1 | 5.858 kg | ~12.5 kg | |
| chiral purity crude Compound 1 | 97.6%/97.5% | 97.4% | |
| achiral purity crude Compound 1 | 98.6% | 98.7% | |

The wet cake of the crude product of both reactions was dissolved on the nutsch in a mixture of dichloromethane (65 L) and methanol (7.5 L) (1.5 hours).

The obtained solution was transferred into a stirring tank loaded with Hyflo (1.13 kg) and BHT (35 g).

The obtained suspension was stirred for 9 minutes before it was filtered through a Celite deep filter plate followed by a 3 m inline filter into the vessel. The stirring tank and filter cake was rinsed with a mixture of dichloromethane (10.0 L) and methanol (1.0 L).

The volume of the product solution was determined to be approximately 94 L. By LOD a product content of 12.5 kg was estimated with a HPLC achiral purity of 98.7% and a chiral purity of 97.4%.

The jacket temperature of the vessel containing the inline-filtered product solution was increased to 57° C. and 43 L of solvent were distilled off at normal pressure within 103 min.

The vessel was switched to reflux. Over 16 min inline filtered n-butanol (11.5 L) was added, the internal temperature rose from 38° C. to 39° C. Seed crystals (11.0 g) were added as slurry in n-butanol (35 ml). 5 min after addition, the brown solution was still clear.

The vessel was switched to distillation. Over 43 min 12 L solvent mixture was distilled off at a jacket temperature of 57° C. The internal temperature rose to 44° C.

The vessel was switched to reflux. Over 13 min inline filtered n-butanol (11.5 L) was added, the internal temperature rose from 44° C. to 45° C. Seed crystals (11.0 g) were added again as slurry in n-butanol (35 ml). 5 min after addition, small particles were observed, forming a thin brown suspension.

The vessel was switched to distillation. Over 43 min 12 L solvent mixture was distilled off. The internal temperature rose to 53° C.

The vessel was switched to reflux. Inline filtered n-butanol (11.6 L) was added, the internal temperature rose to 54° C.

The vessel was switched again to distillation. After distilling off 4.0 L an internal temperature of 60° C. was reached and the system was switched to reflux.

Inline filtered n-butanol (11.4 L) was added and the brown suspension was stirred for 2 h at a jacket temperature of 80° C. (IT: 61-67° C.).

Over 60 min, the jacket temperature was lowered to 25° C. and the brown suspension was stirred at 25° C. overnight.

The next morning, the crude was filtered off (filtration time: 21 min). The filter cake was washed with inline filtered n-BuOH (11.3 L & 11.5 L) and inline filtered TBME (2×11.5 L).

The obtained product was dried in two portions at 70° C. for 24 h. In total 10.187 kg (68% yield) of a white solid with an achiral purity of 99.3% and a chiral purity of 97.9% was obtained. NMR indicated a residual n-BuOH content of 0.055/0.053 equivalents.

EQUIVALENTS

It is to be understood that the invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

We claim:

1. A method, comprising
(a) combining racemic Intermediate I-5:

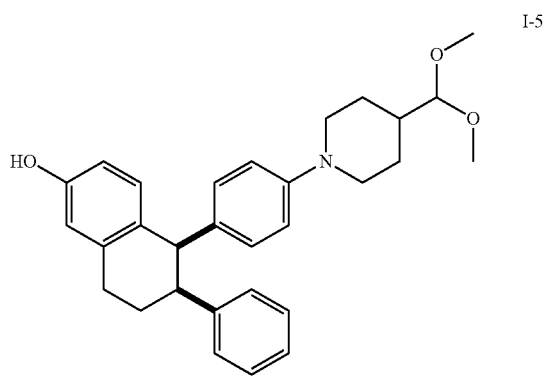 [SMILES: COC(OC)C1CCN(c2ccc([C@@H]3c4ccc(O)cc4CC[C@@H]3c3ccccc3)cc2)CC1]

with an additive in a solvent to prepare a reaction mixture ("step (a) reaction mixture");

(b) heating the step (a) reaction mixture at reflux to prepare a solution ("step (b) solution"), followed by cooling the step (b) solution to a temperature of about 50° C. to about 100° C.;

(c) combining (R)-proline and water to prepare a solution ("step (c) solution"), wherein the molar ratio of (R)-proline to the total amount of Intermediate I-5 is about 0.40:1 to about 1.00:1;

(d) adding about 1% to less than about 50% by volume of the step (c) solution to the step (b) solution to prepare a reaction mixture ("step (d) reaction mixture");

(e) adding an amount of an agent that induces nucleation to the step (d) reaction mixture to prepare a reaction mixture ("step (e) reaction mixture");

(f) adding about 1% to less than about 50% by volume of the step (c) solution to the step (e) reaction mixture to prepare a reaction mixture ("step (f) reaction mixture");

(g) adding an amount of the agent that induces nucleation to the step (f) reaction mixture to prepare a reaction mixture ("step (g) reaction mixture"); and (h) adding the remainder of the step (c) solution to the step (g) reaction mixture to prepare a reaction mixture ("step (h) reaction mixture") to provide Intermediate I-6:

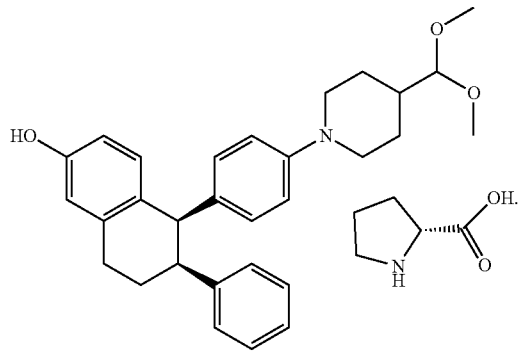

2. The method of claim 1, wherein the agent that induces nucleation is a crystallization promoter.

3. The method of claim 2, wherein the crystallization promoter is a seed crystal comprising Intermediate I-6.

4. The method of claim 1, wherein the additive is an antioxidant, a radical scavenger, an oxygen scavenger, or a metal chelator.

5. The method of claim 1, wherein the additive is dibutylhydroxytoluene, ascorbic acid, alpha-tocopherol, or ethylenediaminetetraacetic acid.

6. A method comprising reductively aminating Intermediate I-9:

with salt Intermediate I-8:

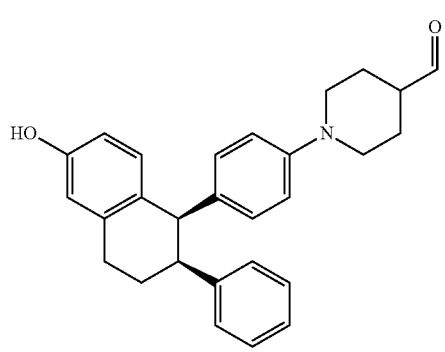

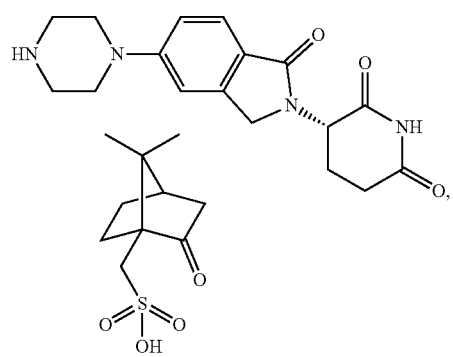

a base, and a reducing agent in a solvent to provide Compound 1:

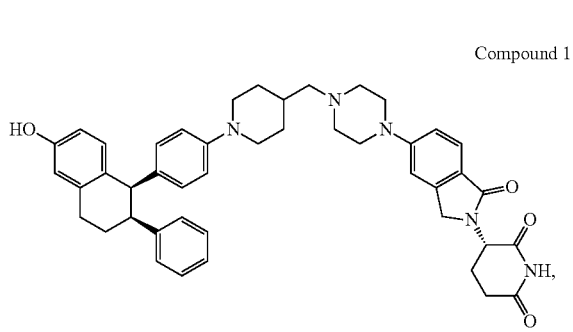

wherein Intermediate I-9 is prepared by a method comprising mixing Intermediate I-6:

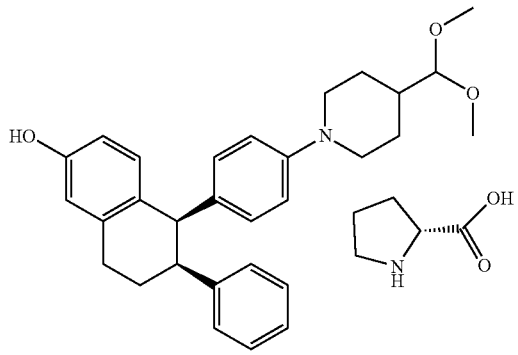

and an acid in a solvent to provide Intermediate I-9:

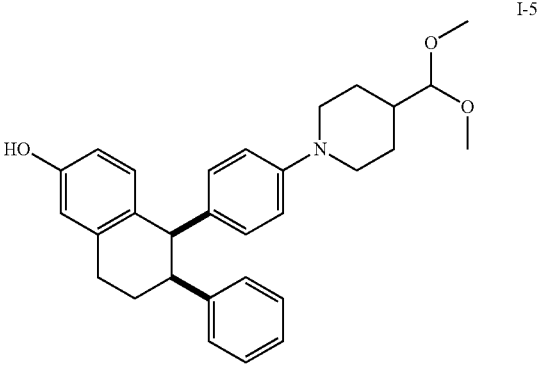 [SMILES: COC(OC)C1CCN(c2ccc([C@@H]3c4ccc(O)cc4CC[C@@H]3c3ccccc3)cc2)CC1]

wherein Intermediate I-6 is prepared by a method comprising (a) combining racemic Intermediate I-5:

with an additive in a solvent to prepare a reaction mixture ("step (a) reaction mixture");

(b) heating the step (a) reaction mixture at reflux to prepare a solution ("step (b) solution"), followed by cooling the step (b) solution to a temperature of about 50° C. to about 100° C.;

(c) combining (R)-proline and water to prepare a solution ("step (c) solution"), wherein the molar ratio of (R)-proline to the total amount of Intermediate I-5 is about 0.40:1 to about 1.00:1;

(d) adding about 1% to less than about 50% by volume of the step (c) solution to the step (b) solution to prepare a reaction mixture ("step (d) reaction mixture");

(e) adding an amount of an agent that induces nucleation to the step (d) reaction mixture to prepare a reaction mixture ("step (e) reaction mixture");

(f) adding about 1% to less than about 50% by volume of the step (c) solution to the step (e) reaction mixture to prepare a reaction mixture ("step (f) reaction mixture");

(g) adding an amount of the agent that induces nucleation to the step (f) reaction mixture to prepare a reaction mixture ("step (g) reaction mixture"); and (h) adding the remainder of the step (c) solution to the step (g) reaction mixture to prepare a reaction mixture ("step (h) reaction mixture") to provide Intermediate I-6:

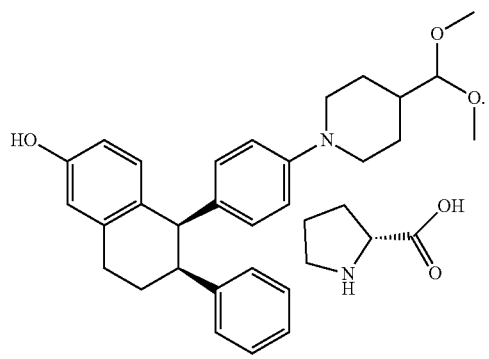

I-6

7. A method, comprising:
(a) reacting Intermediate I-2A:

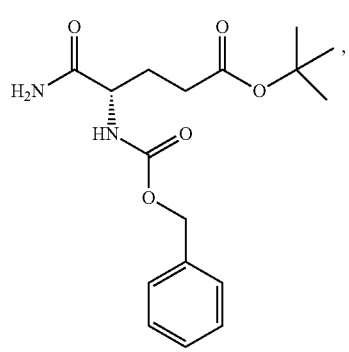

I-2A a hydrogen source, and, optionally, a catalyst, in a solvent to provide Intermediate I-3A:

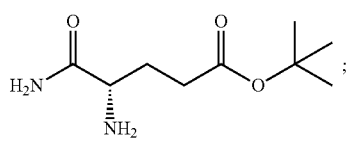

I-3A (b) reducing Intermediate I-2:

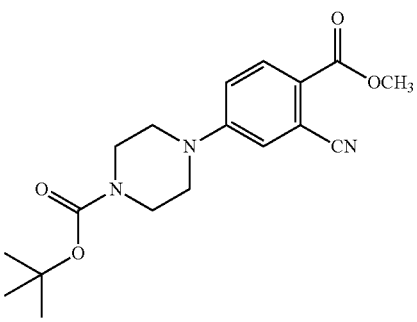

I-2 in a solvent in the presence of a reducing agent to provide Intermediate I-3:

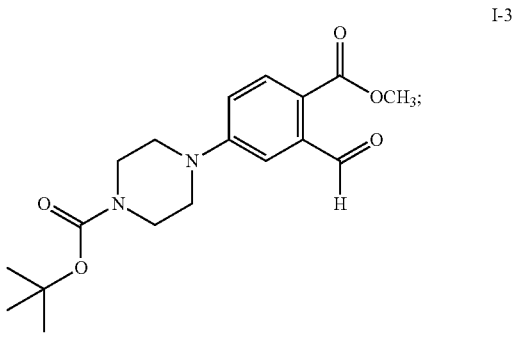 [SMILES: COC(=O)c1ccc(N2CCN(C(=O)OC(C)(C)C)CC2)cc1C=O]

I-3

(c) reacting Intermediate I-3:

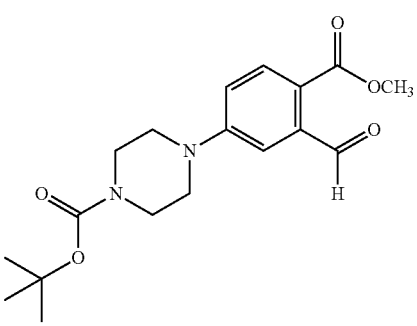

I-3 with Intermediate I-3A:

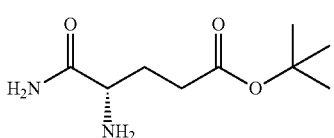

I-3A in a solvent in the presence of a reducing agent to provide Intermediate I-4:

(d) reacting Intermediate I-4:

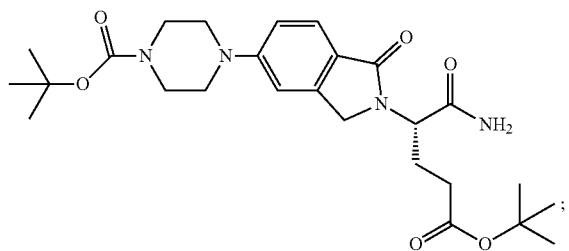

and camphorsulfonic acid in a solvent to provide salt Intermediate I-8:

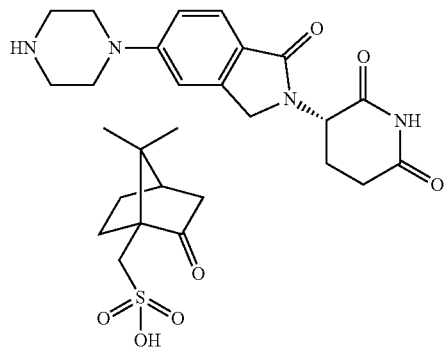

and one or more byproducts;

(e1) combining racemic Intermediate I-5:

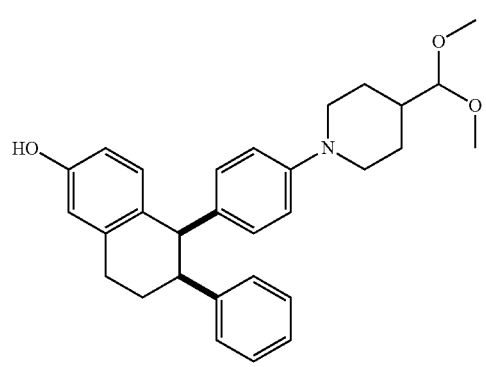

with an additive in a solvent to prepare a reaction mixture ("step (e1) reaction mixture");

(e2) heating the step (e1) reaction mixture at reflux to prepare a solution ("step (e2) solution"), followed by cooling the step (e2) solution to a temperature of about 50° C. to about 100° C.;

(e3) combining (R)-proline and water to prepare a solution ("step (e3) solution"), wherein the molar ratio of (R)-proline to the total amount of Intermediate I-5 is about 0.40:1 to about 1.00:1;

(e4) adding about 1% to less than about 50% by volume of the step (e3) solution to the step (e2) solution to prepare a reaction mixture ("step (e4) reaction mixture");

(e5) adding an amount of an agent that induces nucleation to the step (e4) reaction mixture to prepare a reaction mixture ("step (e5) reaction mixture");

(e6) adding about 1% to less than about 50% by volume of the step (e5) solution to the step (e5) reaction mixture to prepare a reaction mixture ("step (e6) reaction mixture");

(e7) adding an amount of the agent that induces nucleation to the step (e6) reaction mixture to prepare a reaction mixture ("step (e7) reaction mixture"); and (e8) adding the remainder of the step (e3) solution to the step (e7) reaction mixture to prepare a reaction mixture ("step (e8) reaction mixture") to provide Intermediate I-6:

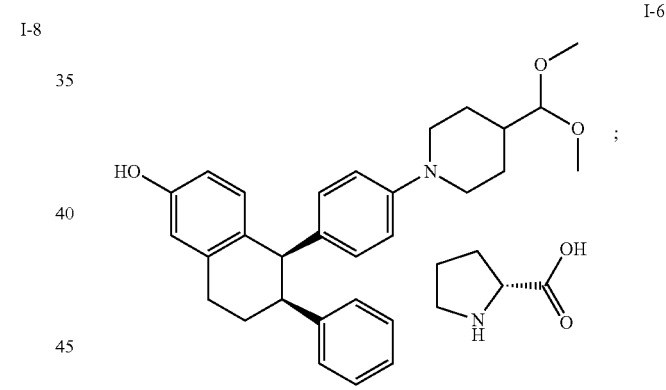

(h) reacting Intermediate I-6:

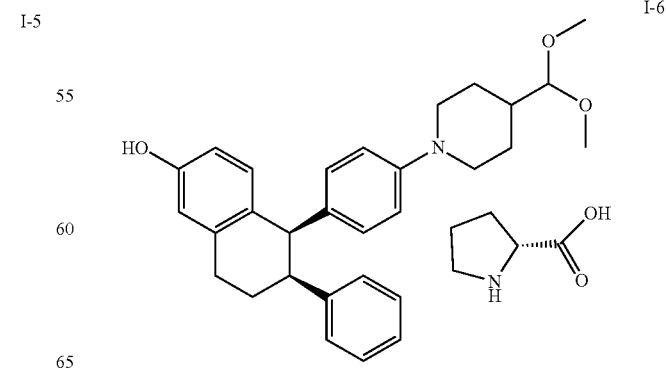

with an acid to provide Intermediate I-9:
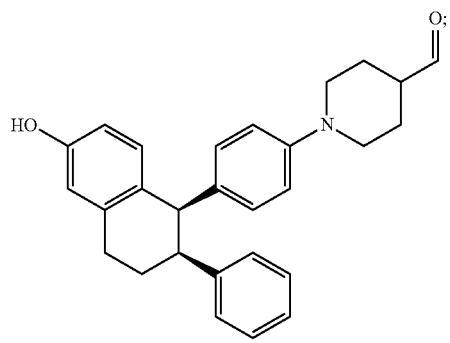
(i) reductively aminating Intermediate I-9:
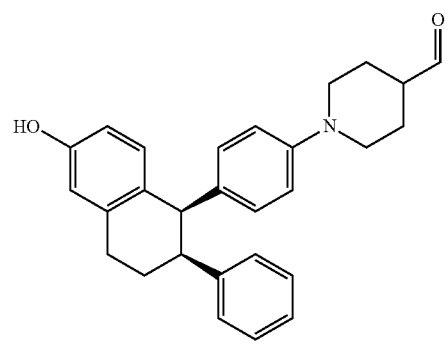
with salt Intermediate I-8:
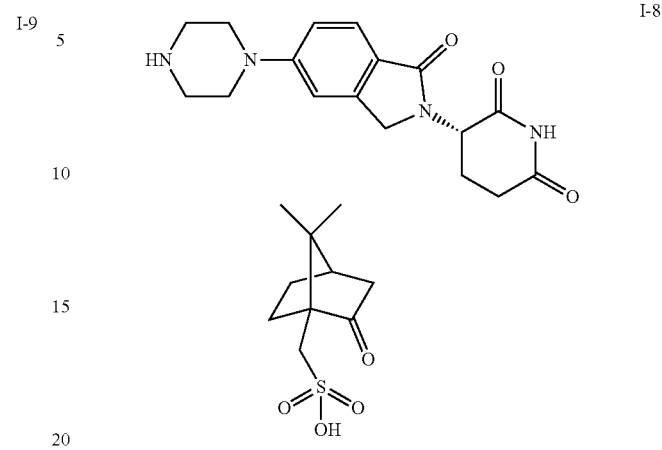
in the presence of a base and a reducing agent to provide Compound 1:
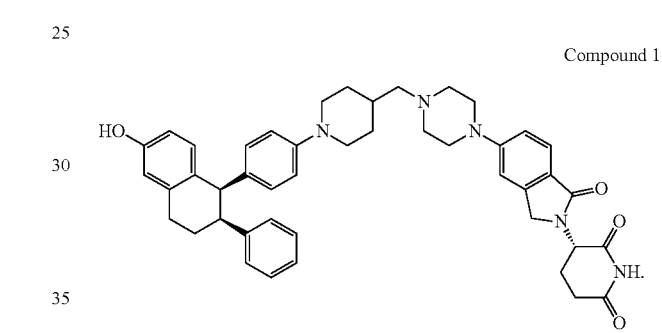
* * * * *

UNITED STATES PATENT AND TRADEMARK OFFICE
CERTIFICATE OF CORRECTION

| | | |
|---|---|---|
| PATENT NO. | : 12,286,419 B2 | Page 1 of 1 |
| APPLICATION NO. | : 17/873748 | |
| DATED | : April 29, 2025 | |
| INVENTOR(S) | : Chungpin Herman Chen et al. | |

It is certified that error appears in the above-identified patent and that said Letters Patent is hereby corrected as shown below:

In the Claims

In Claim 7, Column 78, Lines 19-20, please replace "(e6) adding about 1% to less than about 50% by volume of the step (e5) solution" with --(e6) adding about 1% to less than 50% by volume of the step (e3) solution--.

Signed and Sealed this
Seventh Day of October, 2025

John A. Squires
*Director of the United States Patent and Trademark Office*